US012263270B2

(12) United States Patent
Badylak et al.

(10) Patent No.: US 12,263,270 B2
(45) Date of Patent: Apr. 1, 2025

(54) ACOUSTIC EXTRACELLULAR MATRIX HYDROGELS AND THEIR USE

(71) Applicant: University of Pittsburgh—Of the Commonwealth System of Higher Education, Pittsburgh, PA (US)

(72) Inventors: Stephen Francis Badylak, West Lafayette, IN (US); George S. Hussey, Cranberry Township, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 474 days.

(21) Appl. No.: 17/434,925

(22) PCT Filed: Mar. 12, 2020

(86) PCT No.: PCT/US2020/022433
§ 371 (c)(1),
(2) Date: Aug. 30, 2021

(87) PCT Pub. No.: WO2020/186082
PCT Pub. Date: Sep. 17, 2020

(65) Prior Publication Data
US 2022/0143265 A1 May 12, 2022

Related U.S. Application Data

(60) Provisional application No. 62/950,565, filed on Dec. 19, 2019, provisional application No. 62/817,787, filed on Mar. 13, 2019.

(51) Int. Cl.
*A61K 31/00* (2006.01)
*A61L 26/00* (2006.01)
(Continued)

(52) U.S. Cl.
CPC ......... *A61L 26/0057* (2013.01); *A61L 26/008* (2013.01); *A61L 27/3633* (2013.01); *A61L 27/52* (2013.01); *A61L 2400/04* (2013.01)

(58) Field of Classification Search
CPC ...................................................... A61K 31/00
See application file for complete search history.

(56) References Cited

U.S. PATENT DOCUMENTS

| 4,902,508 A | 2/1990 | Badylak et al. |
| 4,956,178 A | 9/1990 | Badylak et al. |

(Continued)

FOREIGN PATENT DOCUMENTS

| CN | 106456837 A | 2/2017 |
| CN | 108295311 A | 7/2018 |

(Continued)

OTHER PUBLICATIONS

Becton Dickinson, BD Biosciences, BD Extracelular Matrix Proteins, BD ECM Product Reference Guide, https://www.bd.com/resource.aspx?idx=17649, 2011.*

(Continued)

*Primary Examiner* — Rosanne Kosson
(74) *Attorney, Agent, or Firm* — Klarquist Sparkman, LLP

(57) ABSTRACT

Methods are disclosed herein for producing a mammalian acoustic extracellular matrix (ECM) hydrogel. In further embodiments, mammalian acoustic ECM hydrogels are disclosed that are produced using the disclosed methods. Also disclosed is a mammalian acoustic ECM hydrogel, wherein the hydrogel is thermoreversible. Methods of using these acoustic ECM hydrogels are also disclosed.

24 Claims, 32 Drawing Sheets

(51) Int. Cl.
    A61L 27/36    (2006.01)
    A61L 27/52    (2006.01)

(56)                References Cited

U.S. PATENT DOCUMENTS 5,281,422  A    1/1994   Badylak et al.
     5,352,463  A   10/1994   Badylak et al.
     5,372,821  A   12/1994   Badylak et al.
     5,554,389  A    9/1996   Badylak et al.
     5,573,784  A   11/1996   Badylak et al.
     5,645,860  A    7/1997   Knapp, Jr. et al.
     5,753,267  A    5/1998   Badylak et al.
     5,762,966  A    6/1998   Knapp, Jr. et al.
     5,771,969  A    6/1998   Garay
     5,866,414  A    2/1999   Badylak et al.
     6,099,567  A    8/2000   Badylak et al.
     6,485,723  B1  11/2002   Badylak et al.
     6,576,265  B1   6/2003   Spievack
     6,579,538  B1   6/2003   Spievack
     6,696,270  B2   2/2004   Badylak et al.
     6,783,776  B2   8/2004   Spievack
     6,793,939  B2   9/2004   Badylak
     6,849,273  B2   2/2005   Spievack
     6,852,339  B2   2/2005   Spievack
     6,861,074  B2   3/2005   Spievack
     6,887,495  B2   5/2005   Spievack
     6,890,562  B2   5/2005   Spievack
     6,890,563  B2   5/2005   Spievack
     6,890,564  B2   5/2005   Spievack
     6,893,666  B2   5/2005   Spievack
     8,361,503  B2   1/2013   Badylak et al.
     8,394,419  B2   3/2013   Borden
     8,691,276  B2   4/2014   Badylak et al.
     9,226,996  B2   1/2016   Moro et al.
     9,364,580  B2   6/2016   Moro et al.
     9,861,662  B2   1/2018   Badylak et al.
    10,004,827  B2   6/2018   Badylak et al.
    10,213,526  B2   2/2019   Badylak et al.
    10,729,813  B2   8/2020   Badylak et al.
    10,736,991  B2   8/2020   Badylak et al.
    11,213,545  B2   1/2022   Badylak et al.
    11,291,688  B2   4/2022   Badylak et al.
    11,389,566  B2   7/2022   Ramer et al.
    11,389,569  B2   7/2022   Badylak et al.
    11,406,736  B2   8/2022   Badylak et al.
 2006/0070631  A1   4/2006   Scopton et al.
 2007/0190165  A1   8/2007   Brey et al.
 2008/0260831  A1  10/2008   Badylak et al.
 2012/0020932  A1   1/2012   Yao et al.
 2013/0060008  A1   3/2013   Wang et al.
 2014/0105856  A1   4/2014   Schendel
 2015/0165091  A1   6/2015   Dalecki et al.
 2016/0166735  A1   6/2016   Chang et al.
 2017/0173217  A1   6/2017   Badylak et al.
 2018/0200405  A1   7/2018   Badylak et al.
 2019/0314552  A1  10/2019   Wadsworth et al.

FOREIGN PATENT DOCUMENTS

EP            0061549  A1    3/1985
   JP          S48006021  A     1/1973
   JP          S57159485  A    10/1982
   JP        2009 528090  A     8/2009
   WO      WO 2015/143310 A1    9/2015
   WO       WO-2015/164728     10/2015
   WO      WO 2018/035491 A1    2/2018
   WO       WO-2019/246442     12/2019
   WO       WO-2019/246444     12/2019
   WO       WO-2019/246447     12/2019

OTHER PUBLICATIONS

Hussey et al, "Ultrasonic cavitation to prepare ECM hydrogels," *Acta Biomaterialia* 108: 77-86 (e-PUB Apr. 5, 2020).

Zoulim, "Inhibition of hepatitis B virus gene expression: A step towards functional cure," *J. Hepatol.* 68: 386-388 (2018).
Ventura et al., "In-vitro and in-vivo evaluation of hemostatic potential of decellularized ECM hydrogels," *Materials Letters* 232: 130-133 (available on-line Aug. 6, 2018).
Garvin and VanderBurgh, "Controlling collagen fiber microstructure in three-dimensional hydrogels using ultrasound," *The Journal of the Acoustical Society of America* 134(2):1491-1502 (Aug. 2013).
Hussey et al, "Ultrasonic cavitation to prepare ECM hydrogels," *Acta Biomaterialia* 108: 77-86 (Abstract, e-PUB Apr. 5, 2020).
Li et al., "Ultrasonic irradiation in the enzymatic extraction of collagen," *Ultrasonics Sonochemistry* 16(5): 605-609 (Dec. 31, 2009).
Luan, "Separation and Characterization of Protein Components in Bovine Tendon Acellular Matrix Materials," *Chinese Master's Theses Full-Text Database, Engineering Technology I*, issue 1 (Jan. 15, 2021), in Chinese with English Abstract.
Shen et al., "Preparation and characterization of a gene-activated matrix mimicking extracellular matrix," *Acta Pharmaceutica Sinica*, 52(11): 1748-1755 (Nov. 12, 2017), in Chinese with English Abstract.
Freytes et al., "Preparation and rheological characterization of a gel form of the porcine urinary bladder matrix," *Biomaterials* 229(11): 1630-1637 (Apr. 2008).
International Search Report and Written Opinion from parent PCT Application No. PCT/US2020/022433 13 pages (mailed May 29, 2020).
Kornmuller et al., "Fabrication of extracellular matrix-derived foams and microcarriers as tissue-specific cell culture and delivery platforms," *Journal of Visualized Experiments* 122:55436 (Apr. 2017).
Uriel et al., "Extraction and assembly of tissue-derived gels for cell culture and tissue engineering," *Tissue Engineering: Part C* 15(3): 309-321 (2009).
Ventura et al., "In-vitro and in-vivo evaluation of hemostatic potential of decellularized ECM hydrogels," *Materials Letters* 232: 130-133 (Dec. 1, 2018)(Abstract).
Wang et al., "Sonication-induced gelation of silk fibroin for cell encapsulation," *Biomaterials* 29(8): 1054-1064 (Mar. 2008).
Adams et al., "Equine bone marrow-derived mesenchymal stromal cells (BMDMSCs) from the ilium and sternum: Are there differences?" *Equine Veterinary Journal* 45(3)372-375, E-pub Sep. 26, 2012.
Badylak et al., "Resorbable bioscaffold for esophageal repair in a dog model," *Journal of Pediatric Surgery* 35(7):1097-1103, Jul. 2000.
Badylak et al., "Esophageal reconstruction with ECM and muscle tissue in a dog model," *The Journal of Surgical Research* 128(1):87-97, Sep. 2005.
Badylak et al., "Small intestinal submucosa as a large diameter vascular graft in the dog," *The Journal of Surgical Research* 47(1):74-80, Jul. 1989.
Brown et al., "Macrophage phenotype as a predictor of constructive remodeling following the implantation of biologically derived surgical mesh materials," *Acta Biomaterialia* 8(3):978-87, E-pub Dec. 2, 2011.
Dziki et al., "Solubilized Extracellular Matrix Bioscaffolds Derived from Diverse Source Tissues Differentially Influence Macrophage Phenotype," *Journal of Biomedical Materials Research—Part A* 105(1):138-147, E-pub Sep. 21, 2016.
El-Fiqi et al. "Collagen hydrogels incorporated with surface-aminated mesoporous nanobioactive glass: improvement of physicochemical stability and mechanical properties is effective for hard tissue engineering," *Acta Biomaterialia* 9(12):9508-9521, E-pub Aug. 6, 2013.
Frenguelli et al, "Hepatic differentiation of human induced pluripotent stem cells (iPSC) using 3D human liver extracellular matrix hydrogel," *Journal of Hepatology*, 68(Suppl):S56, Apr. 13, 2018.
Huleihel et al., "Macrophage phenotype in response to ECM bioscaffolds," *Seminars in Immunology* 29:2-13, Feb. 2017.
Hussey et al., "Extracellular matrix-based materials for regenerative medicine," *Nature Reviews Materials* 3:159-173, May 29, 2018.
Kakushima et al., "Endoscopic submucosal dissection for gastrointestinal neoplasms," *World Journal of Gastroenterology* 14(19):2962-2967, May 21, 2008.

(56) References Cited

OTHER PUBLICATIONS

Keane et al., "Tissue-specific effects of esophageal extracellular matrix," *Tissue Engineering Part A* 21(17-18):2293-2300, E-pub Aug. 12, 2015.

Kim et al., "Application of ultrasonic treatment to extraction of collagen from the skins of sea bass Lateolabrax japonicus," *Fisheries Science* 79(5):849-856, Jul. 6, 2013.

Lange et al., "Pilot study of a novel vacuum-assisted method for decellularization of tracheae for clinical tissue engineering applications," *Journal of Tissue Engineering and Regenerative Medicine* 11(3):800-811, E-pub Feb. 17, 2015.

Loneker et al., "Solubilized liver extracellular matrix maintains primary rat hepatocyte phenotype in-vitro," *Journal of Biomedical Materials Research Part A* 104(4):957-965, E-pub Jan. 13, 2016.

Mase et al., "Clinical application of an acellular biologic scaffold for surgical repair of a large, traumatic quadriceps femoris muscle defect," *Orthopedics* 33(7):511, Jul. 13, 2010.

Medberry et al., "Hydrogels derived from central nervous system extracellular matrix," *Biomaterials* 34(4):1033-1040, E-pub Nov. 16, 2012.

Reing et al., "The effects of processing methods upon mechanical and biologic properties of porcine dermal extracellular matrix scaffolds," *Biomaterials* 31(33):8626-8633, E-pub Aug. 21, 2010.

Saldin et al., "Extracellular matrix hydrogels from decellularized tissues: Structure and function," *Acta Biomaterialia* 49:1-15, E-pub Dec. 1, 2016.

Sicari et al., "The promotion of a constructive macrophage phenotype by solubilized extracellular matrix," *Biomaterials* 35(30):8605-8612, E-pub Jul. 16, 2014.

Spang et al., "Extracellular matrix hydrogel therapies: In vivo applications and development," *Acta Biomaterialia* 68:1-14, E-pub Dec. 20, 2017.

Thornton et al., "Healing in the gastrointestinal tract," *The Surgical Clinics of North America* 77(3):549-573, Jun. 1997.

Tosh et al., "Determination of the maximum gelation temperature in gelatin gels," *Applied Physics Letters* 84(21):4242-4244, May 24, 2004.

Uraoka et al., "Submucosal injection solution for gastrointestinal tract endoscopic mucosal resection and endoscopic submucosal dissection," *Drug Design, Development and Therapy* 2:131-138, Feb. 6, 2009.

Uriel et al., "The role of adipose protein derived hydrogels in adipogenesis," *Biomaterials* 29(27):3712-3719, E-pub Jun. 24, 2008.

Voytik-Harbin et al., "Small intestinal submucosa: A tissue-derived extracellular matrix that promotes tissue-specific growth and differentiation of cells in vitro," *Tissue Engineering* 4(2):157-174, Jun. 1, 1998.

Wolf., "Polypropylene surgical mesh coated with extracellular matrix mitigates the host foreign body response," *Journal of Biomedical Materials Research Part A* 102(1):234-246, E-pub Jul. 19, 2013.

Wu et al., "Experimental Study on Lung Extracellular Matrix Hydrogel for Treating Radiation-Induced Lung Injury in Rats," *China Journal of Modern Medicine* 29: 12 (Jun. 27, 2019)(with machine English language translation).

* cited by examiner

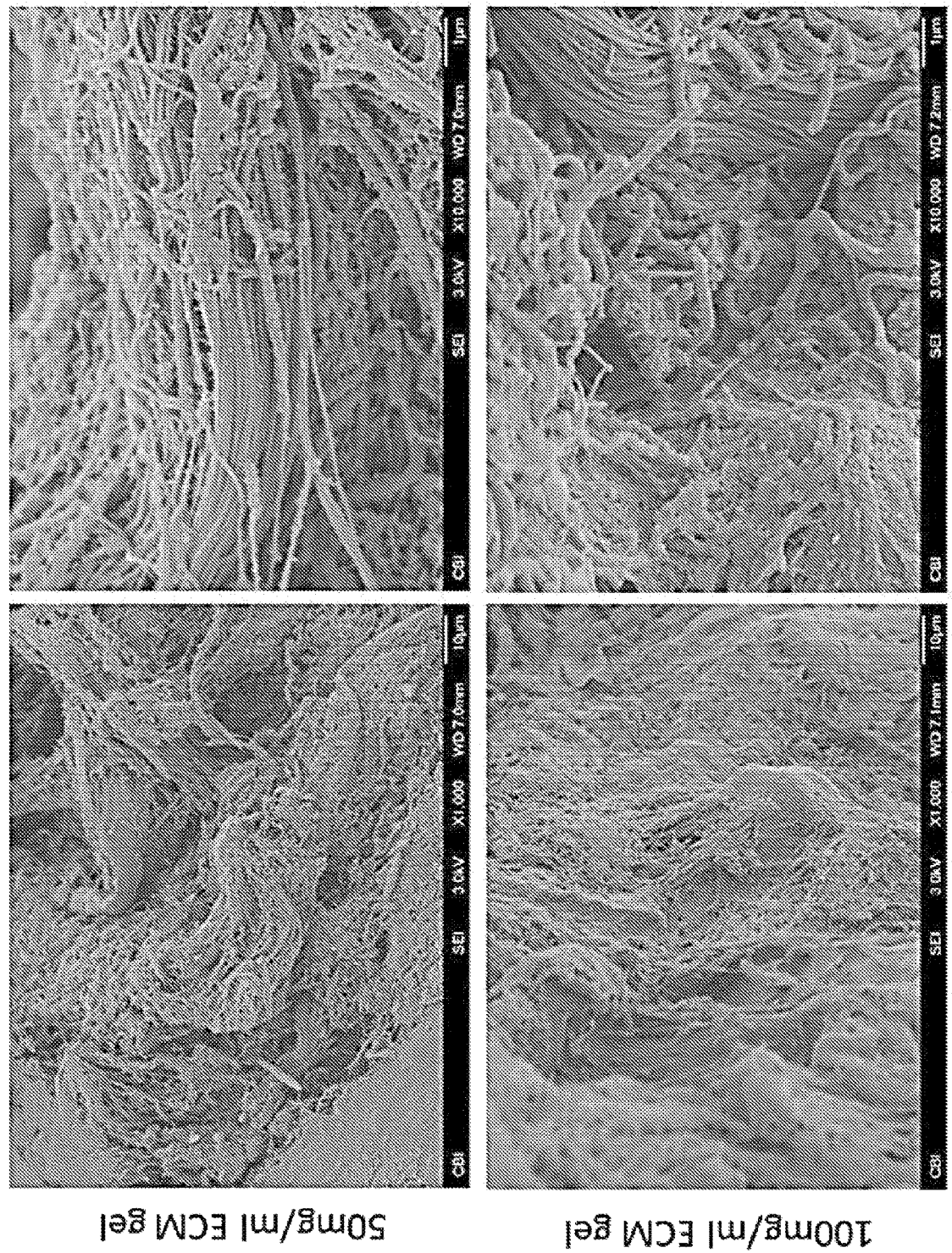

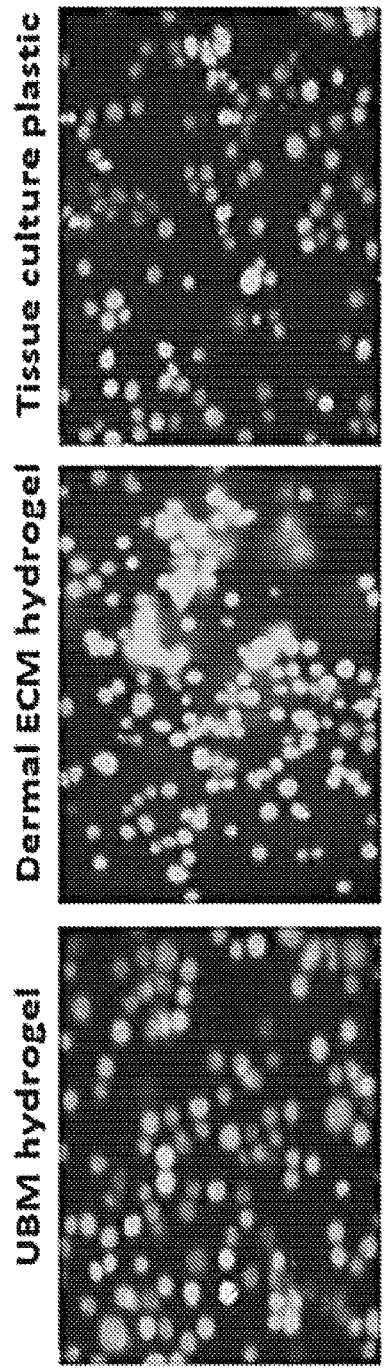
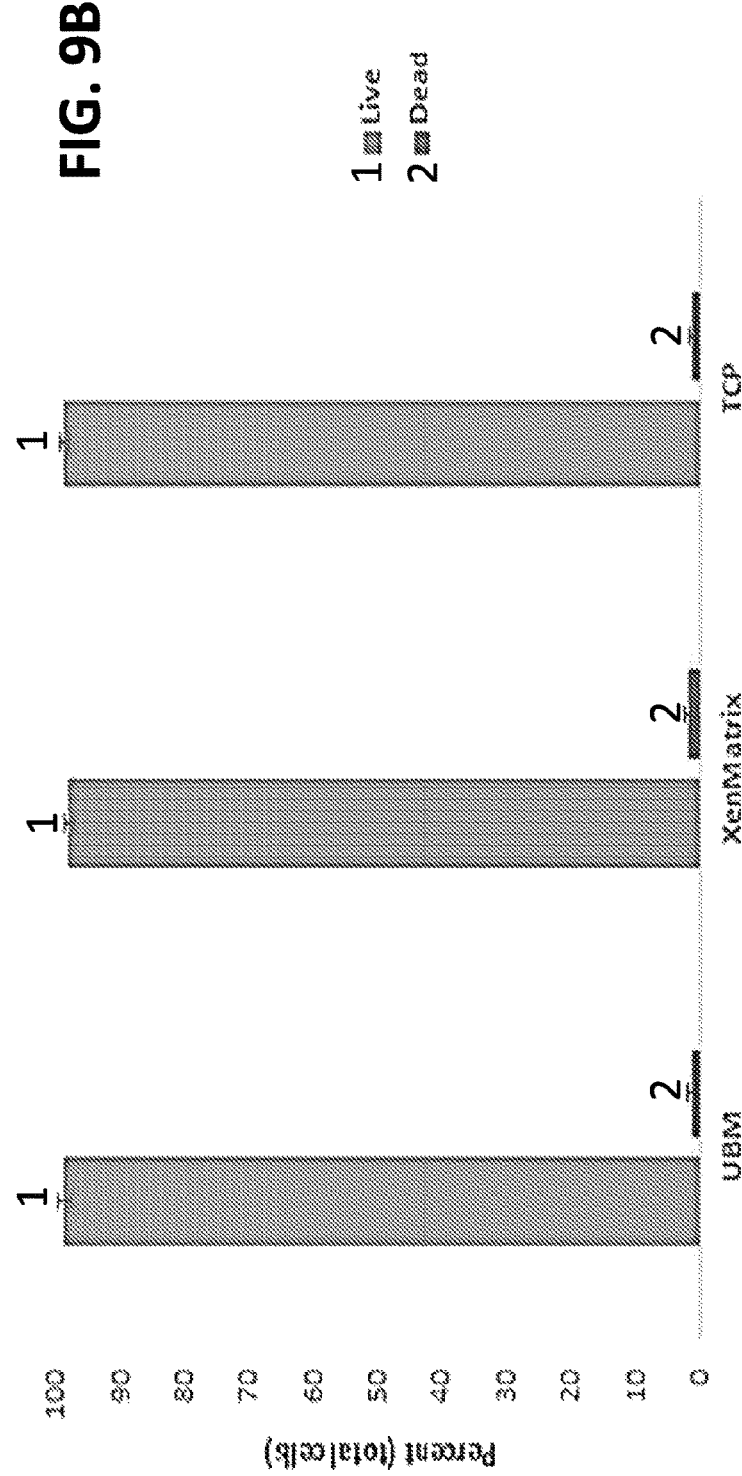
FIG. 9B

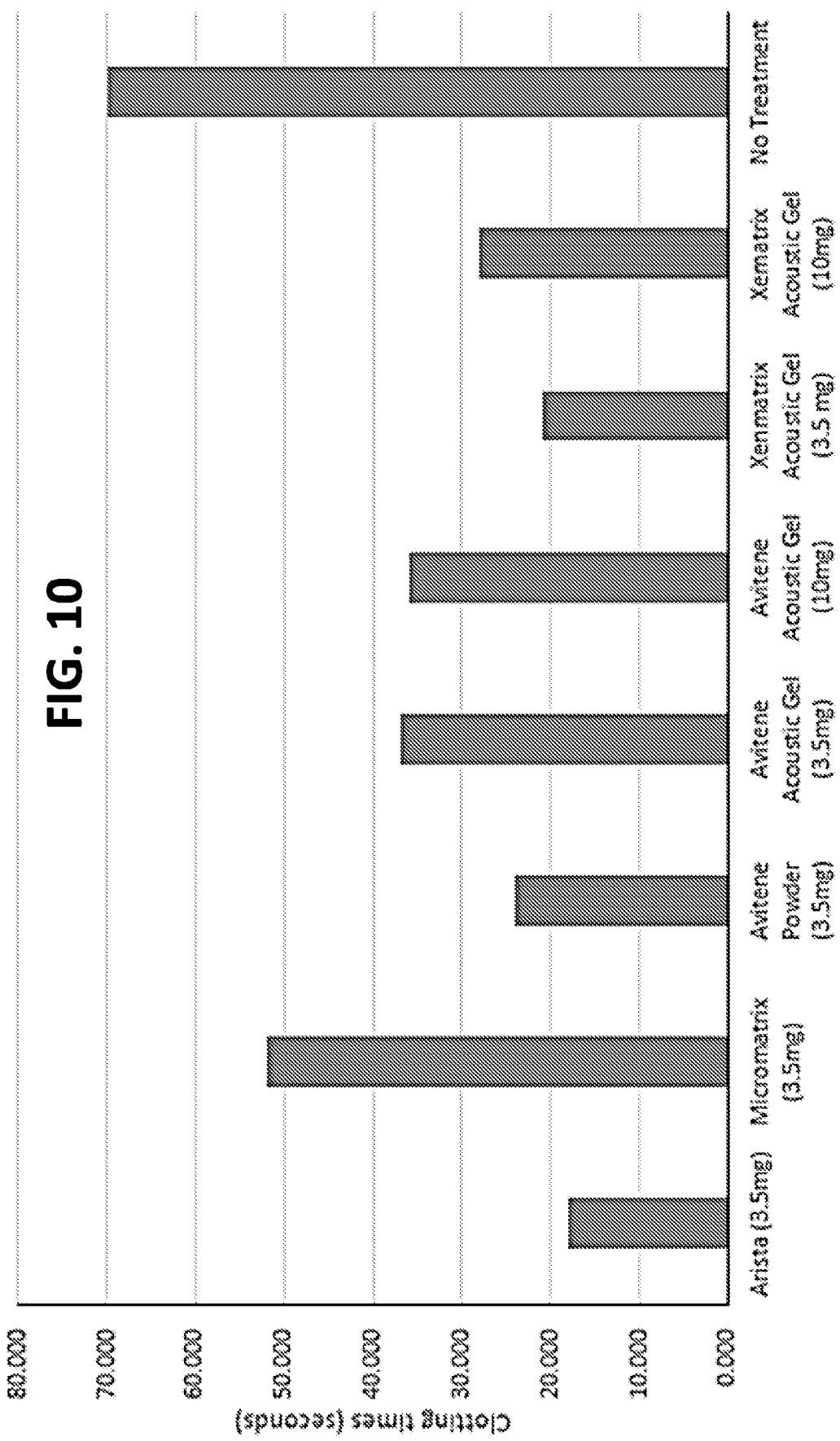

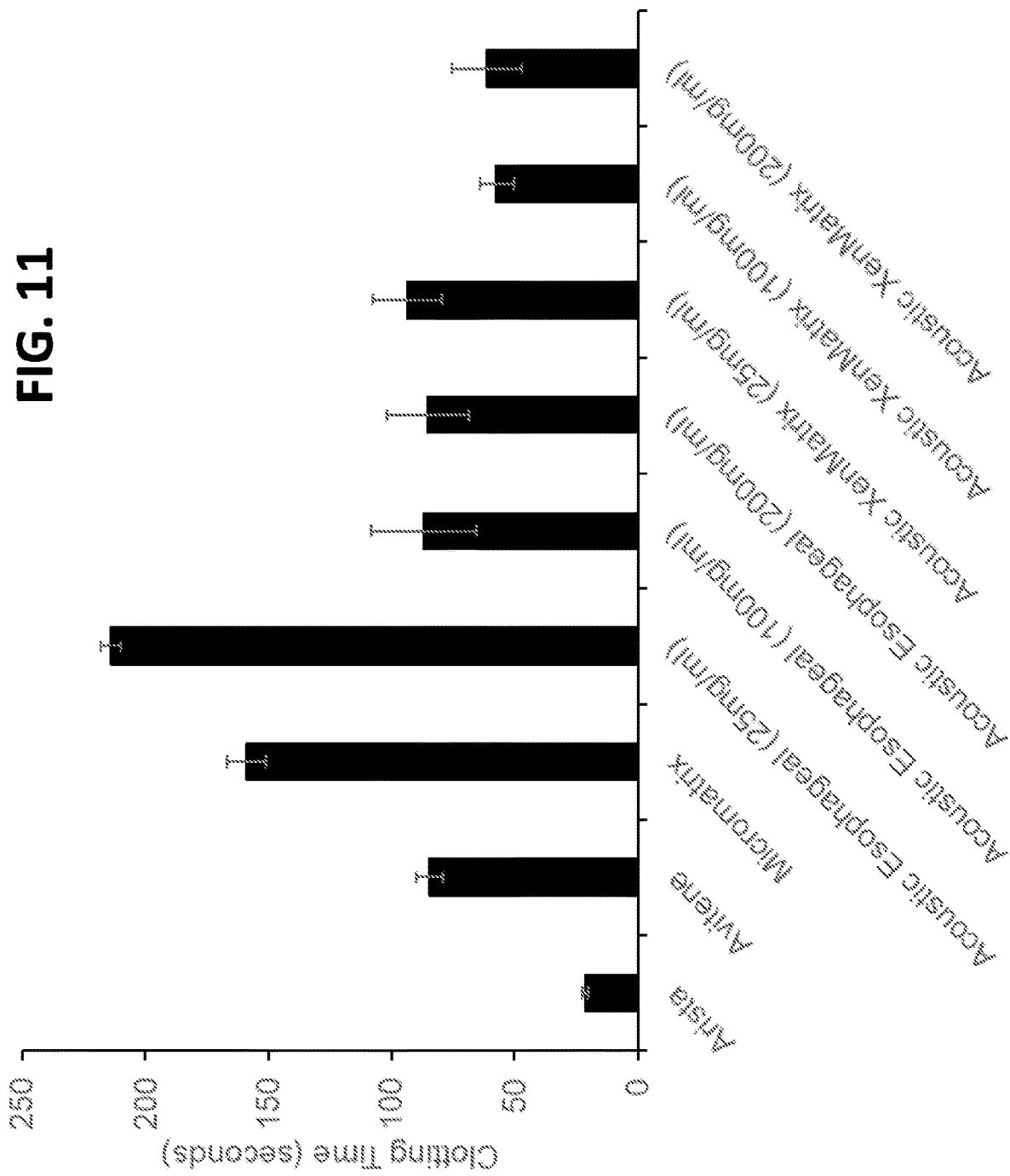

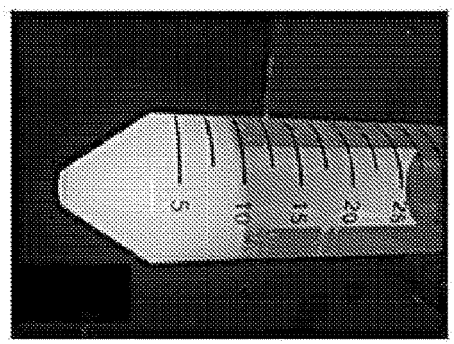
FIG. 14D  FIG. 14C  FIG. 14B
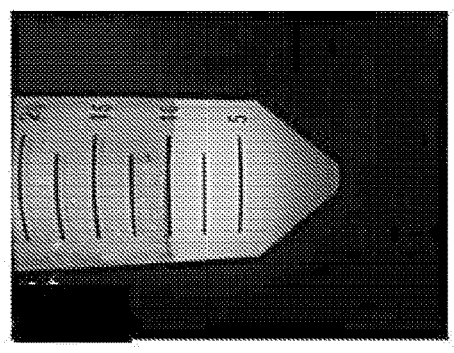
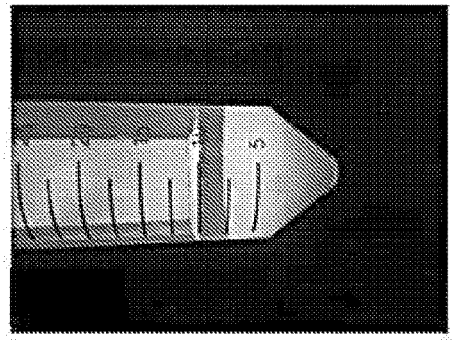
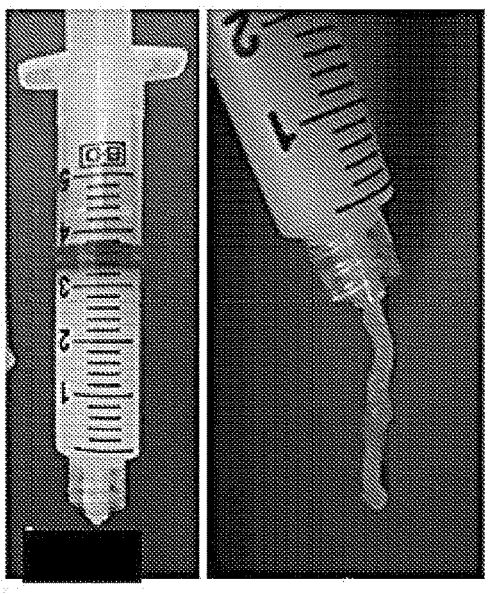
FIG. 14F
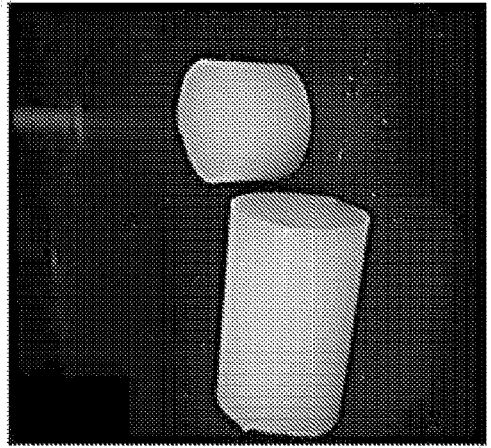
FIG. 14E
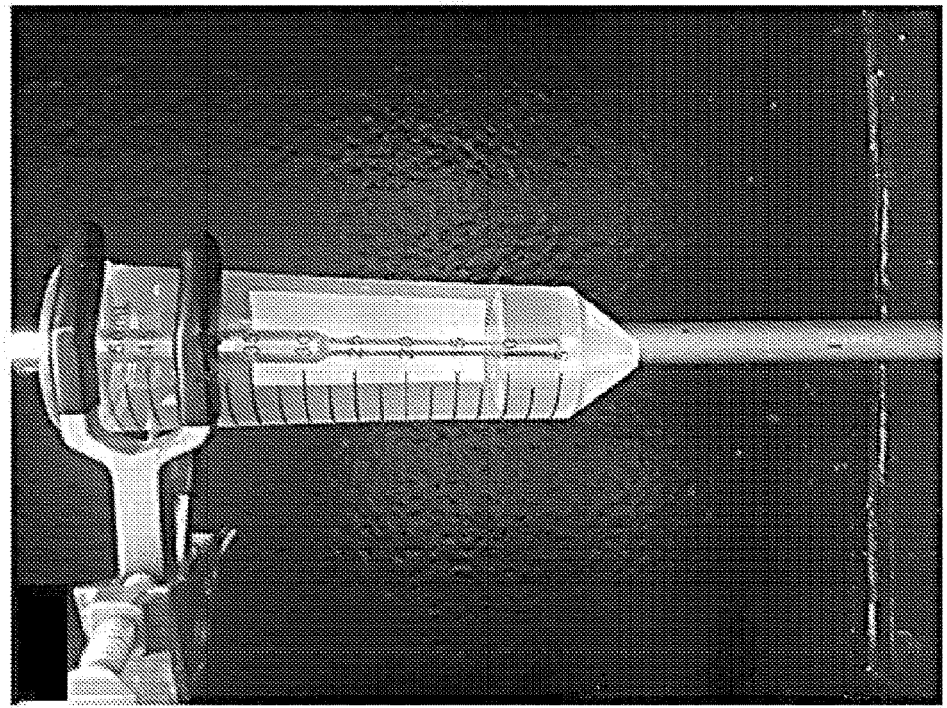
FIG. 14A

FIG. 19A
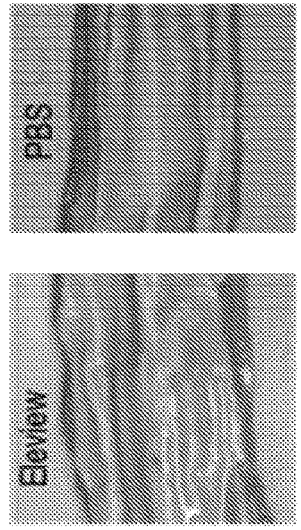
FIG. 19C
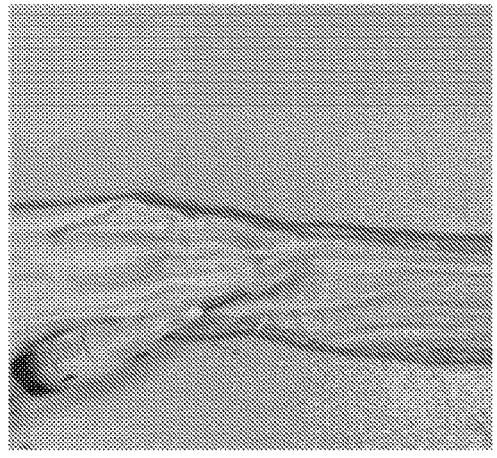
FIG. 19B
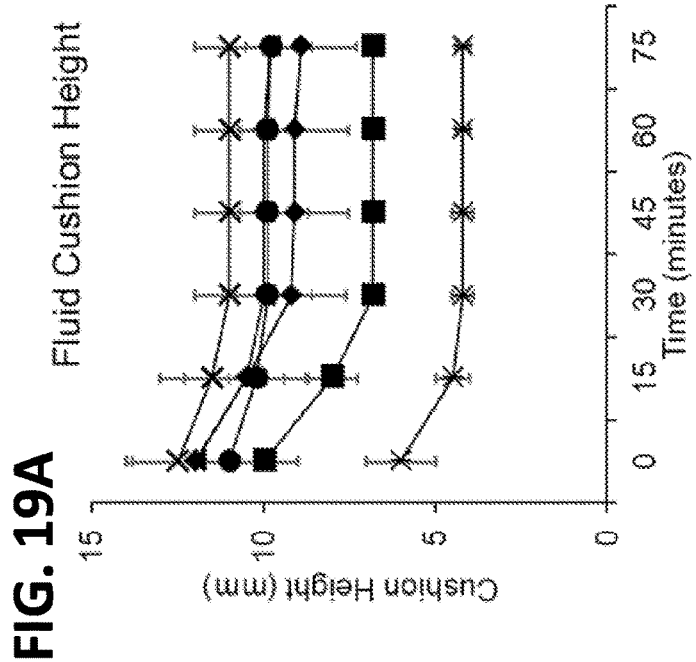

FIG. 20B
Average Modulus
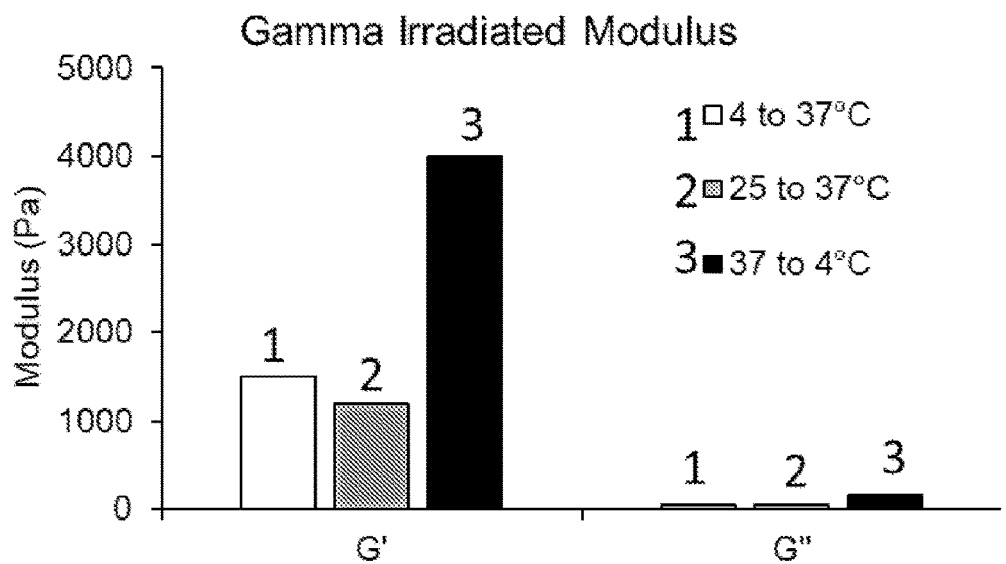
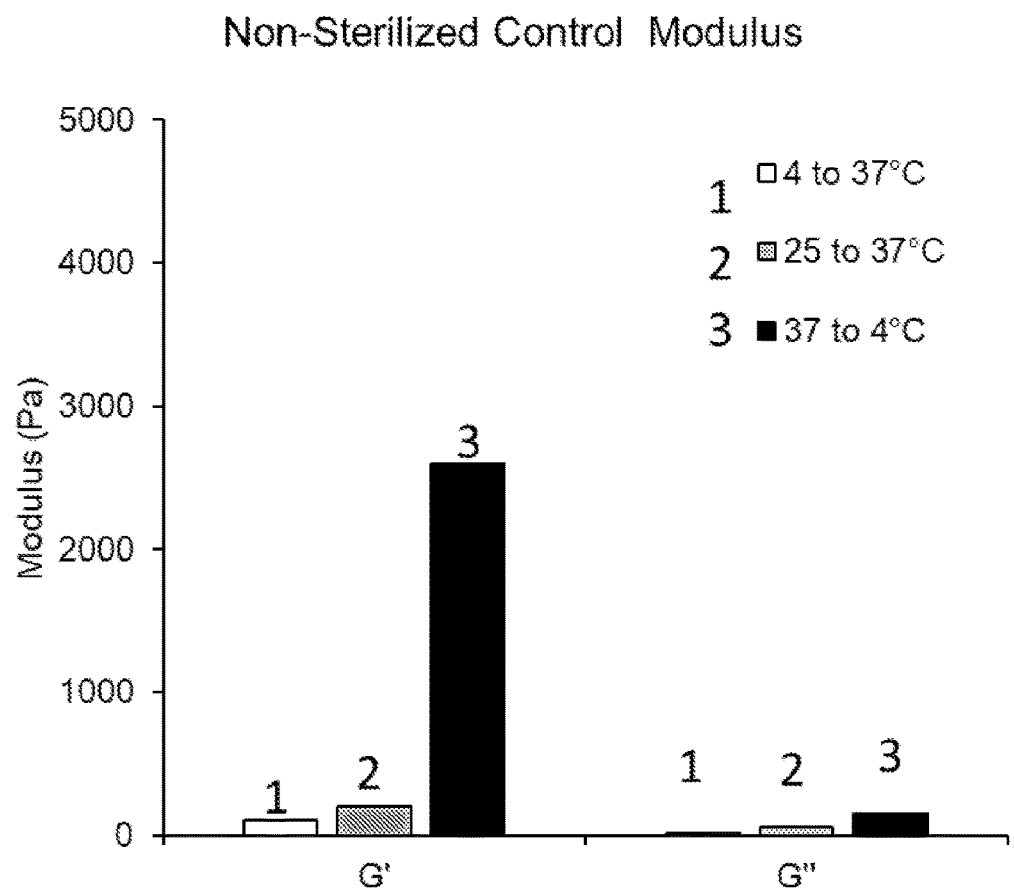

ACOUSTIC EXTRACELLULAR MATRIX HYDROGELS AND THEIR USE

CROSS REFERENCE TO RELATED APPLICATIONS

This is a § 371 U.S. national stage of International Application No. PCT/US2020/022433, filed Mar. 12, 2020, which claims the benefit of U.S. Provisional Application No. 62/817,787, filed Mar. 13, 2019, and U.S. Provisional Application No. 62/950,565, filed Dec. 19, 2019, which are incorporated by reference herein in their entirety.

FIELD OF THE DISCLOSURE

This relates to the field of hydrogels, specifically to acoustic extracellular matrix (ECM) hydrogels that are produced from mammalian ECM using ultrasound and their use.

BACKGROUND

Hydrogels composed of purified ECM components such as collagen, hyaluronic acid, silk fibroin, laminin, and fibronectin, have been widely used in tissue engineering applications. However, these purified, single component ECM biomaterials lack the complex biochemistry of native tissue ECM. Decellularization of whole tissues or organs provides for an alternative method for harvesting ECM that preserves the biochemistry of native tissue ECM. A major advancement in the use of ECM is the ability to form hydrogels, thereby expanding the clinical applicability of an ECM. The known art for producing hydrogels from ECM has largely focused on digestion of the ECM material with an acid protease in an acidic solution; the use of $\alpha$-amylase digestion to produce ECM foams; or the use of chaotropic extraction buffers and lengthy dialysis procedures. ECM hydrogels made according to such art are inevitably subjected to protein degradation and denaturation thereby attenuating the bioactivity of the full complement of ECM molecules and tissue specific ECM components. Moreover, enzyme-based methods for producing ECM hydrogels require lengthy incubation times ranging from 24-72 hours to achieve adequate solubilization of ECM components. Methods are needed to form an ECM hydrogel without the use of acidic or alkaline solutions and protease digestion.

SUMMARY OF THE DISCLOSURE

Methods are disclosed herein for producing a mammalian acoustic extracellular matrix (ECM) hydrogel that is biocompatible. These methods include solubilizing mammalian ECM in a liquid at a concentration of 25 mg/ml to 600 mg/ml in a liquid, such as a buffered saline solution, with ultrasound at a frequency of about 20 kHz to about 100 kHz at for a sufficient period of time at a temperature from 30 to 43° C. to produce an acoustic ECM hydrogel in a liquid phase. In some embodiments, the method includes cooling the acoustic ECM hydrogel in the liquid phase to a temperature of 37° C. or less to produce the acoustic ECM hydrogel in the gel phase. In further embodiments, acoustic ECM hydrogels are disclosed that are produced using the disclosed methods.

Also disclosed is an acoustic ECM hydrogel that is thermoreversible. In some non-limiting examples, the acoustic ECM hydrogel is in the solid phase at temperatures below about 37° C. and is in the liquid phase at temperatures above about 37° C. These hydrogels are produced from mammalian ECM.

Methods of using these acoustic ECM hydrogels are also disclosed.

The foregoing and other features and advantages of the invention will become more apparent from the following detailed description of several embodiments which proceeds with reference to the accompanying figures.

BRIEF DESCRIPTION OF THE FIGURES

FIG. 3: Scanning electron micrographs (SEM). ECM hydrogels prepared by sonication showed a textured and fibrous surface.

FIGS. 9A-9B: Cytocompatibility assay. (A) 3T3 Fibroblasts were seeded on control (uncoated), or on dishes coated with acoustic ECM hydrogel prepared from UBM, SIS or Dermis, and cultured for 24 h. The VYBRANT® MTT Cell Proliferation Assay Kit (Thermo Fisher) used to evaluate the viability of cells. The results show that all ECMs were non-cytotoxic for 3T3 fibroblasts (n=3). (B) Live/Dead assay. Hydrogel coated plates were seeded with equine mesenchymal stem cells and were compared to cells growing on tissue culture plastic. Viability was evaluated with the Live/Dead assay kit (Invitrogen). Images were taken for 5, 200× fields across 3 technical replicates. Percent live dead cells were quantified using Cell Profiler. Error bars represent standard deviation.

FIG. 10: The Lee White clotting method was used to determine clotting times (hemostasis) of hemostatic powders, AVITENE™ and XENMATRIX™ ECM prepared as a hydrogel by the acoustic method. XENMATRIX™ is an ECM product harvested from porcine dermis. The data show that compared to no treatment, the AVITENE™ and XENMATRIX™ gels achieved rapid hemostasis.

FIG. 11: In-vivo evaluation of clotting times using a rat liver laceration model. Rats were subjected to liver laceration and treated with hemostatic agents. Sprague-Dawley Rats were randomly assigned into 5 experimental groups (n=5 per group): Arista powder (BD/CR Bard) AVITENE™ powder (BD/CR Bard), Micromatrix powder (ACell); indicated concentrations of Esophageal ECM prepared as a hydrogel using the acoustic method, indicated concentrations of XenMatrix (BD/CR Bard) prepared as a hydrogel using the acoustic method. The data show that mammalian ECM prepared as a hydrogel using the acoustic methods can induce hemostasis in vivo.

FIGS. 14A-14F. Sonication of comminuted ECM and temperature-induced gelation. (A) Demonstration of the sonicator tip immersion depth in a 50 ml conical tube. (B, C) Comminuted dermal ECM powder in 1×PBS before (B) and after (C) sonication. (D) After incubation at temperatures below 25° C., inversion of the tube showed that the solubilized ECM polymerized into a rigid gel. (E) Polymerized gels can conform to 3D geometries. (F) Solubilized ECM can be transferred to a syringe (top panel), then chilled to temperatures below 25° C. to yield an injectable form of the gel (bottom panel).

FIGS. 19A-19C. Acoustic Hydrogel as a Submucosal Fluid Cushion. (A) Acoustic extracellular matrix (ECM) hydrogel (100 mg/mL), was prepared from dermal ECM (dECM) and esophageal mucosa ECM (eECM) and used as a submucosal fluid cushion ex vivo. The effect of 20 kGy gamma irradiation (γ) upon the acoustic ECM hydrogel fluid cushion height was evaluated. Clinical standard Eleview and PBS were used for controls. Fluid cushion heights were measured after injection of 2 mL of test article in a porcine esophagus over time. Values are expressed as mean+/−SD (n=3). (B) The acoustic hydrogel samples are injectable through a 16G syringe. (C) Representative pictures of the test article fluid cushion heights after 75 min.

FIGS. 20A-20B. Acoustic hydrogel gelation. Hydrogel "stiffness" over time was measured for gamma irradiated (20 kGy) and non-sterilized control acoustic hydrogel (dermal ECM 100 mg/mL). The storage modulus ("stiffness") (G') and loss modulus (G") were measured by applying a small, 0.5% oscillatory strain to the sample. Three temperature profiles were tested: temperature was rapidly raised from the initial storage temperature to final temperature: 4 to 37° C., 25 to 37° C., or 37 to 4° C. (A) Representative graphs of the time sweep are shown (B). The average storage and loss modulus, averaged over the final 5 minutes of the test, are shown.

DETAILED DESCRIPTION OF SEVERAL EMBODIMENTS

Figure 1A:
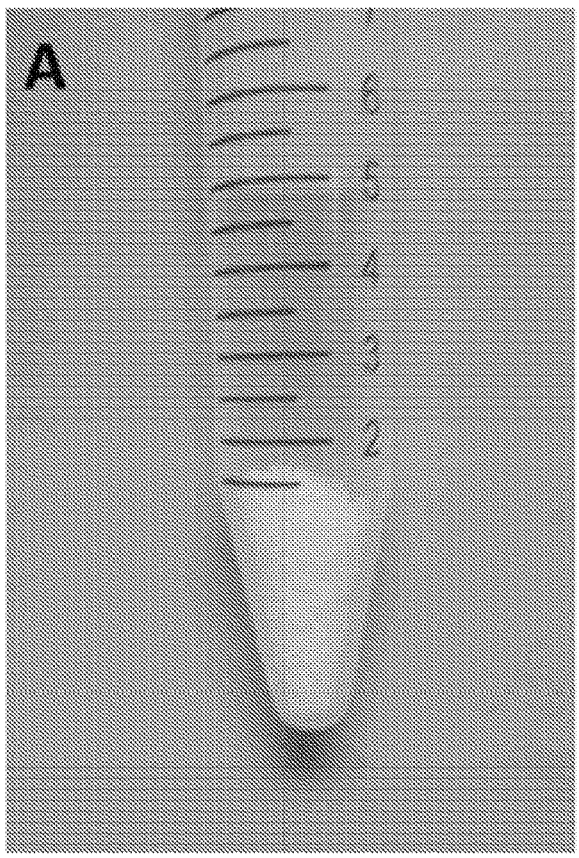
FIGS. 1A-1D: Preparation of an acoustic ECM hydrogel using sonication. (A) Comminuted dermis ECM in a 15 ml conical tube. (B) After resuspension of the ECM powder in PBS, the conical tube is placed in an ice water bath, and the sonicator probe is inserted into the tube. (C, D) Following solubilization of the ECM by sonication pulses, the pre-gel solution is pipetted into 3D molds or thinly spread over Teflon sheets, and incubated at a temperature ≤37 C to induce gelation.
Figure 1B:
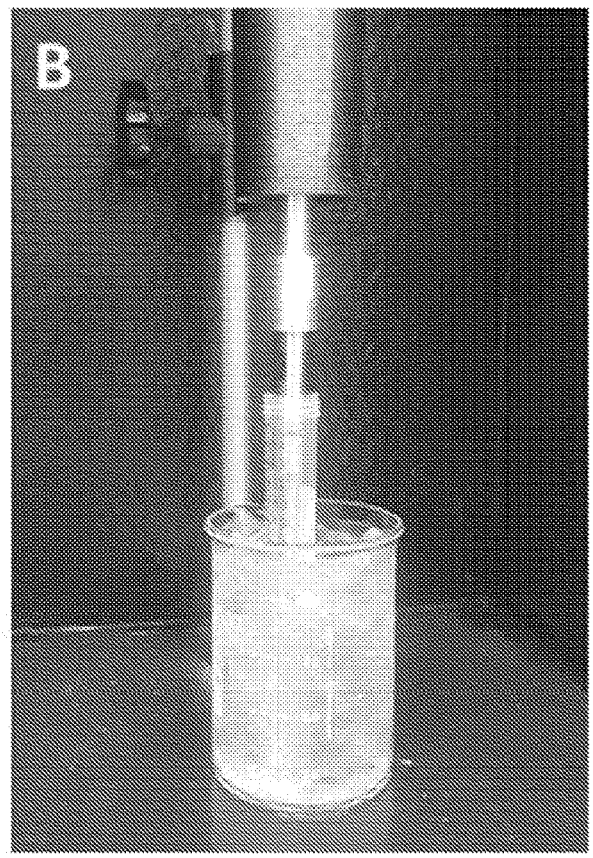

ECM hydrogels have been used as a substrate for 3D organoid culture, and in numerous preclinical and clinical applications to facilitate repair and reconstruction of a variety of tissues. Previously ECM hydrogel materials were fabricated using lengthy methods that have focused on enzymatic digestion of the ECM with an acid protease in an acidic solution; or the use of chaotropic extraction buffers and dialysis procedures which can affect native protein structure and function. Disclosed herein is a method to prepare hydrogels from ECM bioscaffolds using ultrasonic cavitation. The solubilized ECM can be induced to rapidly self-assemble into a gel by adjusting temperature, and the material properties of the gel can be tailored by adjusting ECM concentration and sonication parameters. ECM bioscaffolds can be successfully solubilized using ultrasound, without enzymatic digestion, and induced to repolymerize into a gel form capable of supporting cell growth. These hydrogels can be used in numerous applications and can be terminally sterilized with gamma irradiation.

To produce the disclosed ECM hydrogels, sonication techniques can be applied to a broad array of tissue specific ECM including, but not limited to, dermis, urinary bladder matrix (UBM), and small intestinal submucosa (SIS). It can also be used with commercially available ECM preparations. In some embodiments, the approach involves resuspension of comminuted ECM in a liquid, such as a buffer, for example, neutral buffered saline solution, followed by ECM solubilization using ultrasound. In some embodiments, the buffered saline solution has an osmolarity of about 290 mOsm/L. A variety of concentrations can be used, and the ECM can be sonicated for at least 60 seconds. Rapid gelation of the ECM solution can be induced by decreasing the temperature of the ECM solution. Gelation time and ECM gel properties can be tuned by adjusting ECM concentration, sonication amplitude and time. In some embodiments, the acoustic ECM hydrogel does not contain an exogenous protease or an inactivated exogenous protease, such as exogenous pepsin, trypsin or hyaluronidase or an inactivated form of exogenous pepsin, trypsin, or hyaluronidase.

Once polymerized, these ECM hydrogels are stable at room temperature and can conform to customizable 3D geometries. ECM hydrogels produced by sonication ("acoustic ECM hydrogels") can be processed into solid scaffolds by freezing and lyophilization procedures which maintain the overall 3D geometry and increase porosity. This technology can support the incorporation of cells or compounds for in-vitro and in-vivo applications. Methods of using the disclosed acoustic ECM hydrogels are also disclosed, such as, but not limited to, to increase hemostasis.

There has been relatively little advancement in large scale manufacturing of ECM hydrogels (Brown et al., supra, 2012). The disclosed methods are of use for large scale manufacturing in several aspects. In some embodiments, ECM hydrogel concentration range can be expanded from 2-20 mg/ml (the limit of enzymatic methods) to 25-100 mg/ml using the ultrasonic cavitation method, which allows for fine tuning of the ECM hydrogel viscoelastic properties for specific clinical applications. In other embodiments, processing time is dramatically reduced from 48-72 hr, to the order of minutes. In further embodiments, the ECM hydrogels can conform to customizable 3D geometries, and can support the incorporation of cells or therapeutic drugs for in vitro and in vivo applications.

Terms

Unless otherwise noted, technical terms are used according to conventional usage. Definitions of common terms in molecular biology can be found in Krebs et al (Eds.), *Lewin's Genes XII*, published by Jones & Bartlett Publishers, 2017; and Meyers et al. (eds.), *The Encyclopedia of Cell Biology and Molecular Medicine*, published by Wiley-VCH in 16 volumes, 2008; and other similar references.

In order to facilitate review of the various embodiments of this disclosure, the following explanations of specific terms are provided:

Acid Protease: An enzyme that cleaves peptide bonds, wherein the enzyme has increased activity of cleaving peptide bonds in an acidic pH. For example and without limitation, acid proteases can include pepsin and trypsin.

Antibiotic: A compound or substance that kills or substantially slows down the growth of bacteria, fungus or any other microbe. An "antibacterial" is a compound or substance that kills or substantially slows the growth of bacteria.

Antibacterial antibiotics are commonly classified based on their mechanism of action, chemical structure, or spectrum of activity. Most target bacterial functions or growth processes. Those that target the bacterial cell wall (for example, penicillins and cephalosporins) or the cell membrane (for example, polymixins), or interfere with essential bacterial enzymes (for example, quinolones and sulfonamides) are bactericidal. Those that target protein synthesis (for example, aminoglycosides, macrolides, and tetracyclines) are generally bacteriostatic. Further categorization is based on their target specificity.

"Narrow-spectrum" antibacterial antibiotics target specific types of bacteria, such as Gram-negative or Gram-positive bacteria. "Broad-spectrum antibiotics" affect a number of different types of bacteria. Antibacterial agents also include cyclic lipopeptides (such as daptomycin), glycylcyclines (such as tigecycline), and oxazolidinones (such as linezolid).

Topical antibiotics are antibiotics that are applied to a body surface, such as the skin or eye. Topical antibiotics are often formulated in an ointment or a cream, and contain active agents such as macrolide antibiotic (such as erythromycin), a sulfa antibiotic (such as sulfacetamide), a cyclic peptide (such as bacitracin a polymyxin) a psuedomonic acid (such as mupirocin), an aminoglycoside (such as neomycin), or a quinolone (such as ciprofloxacin or ofloxacin), a nitroimidazole (such as metronidazloe), or a combination of drugs (such as bacitracine/polymyxin or neomycin/polymyxin B/bacitracin).

Biocompatible: Any material, that, when implanted in a mammalian subject, does not provoke an adverse response in the subject. A biocompatible material, when introduced into an individual, is able to perform its intended function, and is not toxic or injurious to that individual, nor does it induce immunological rejection of the material in the subject.

Bioscaffold: A scaffold, usually a solid support or a gel, that is biocompatible. A bioscaffold is composed of naturally occurring materials. A "bio-synthetic scaffold" is composed of non-naturally occurring and naturally occurring materials.

Centrifugation: The process whereby a centrifugal force is applied to a mixture, whereby more-dense components of the mixture migrate away from the axis of the centrifuge relative to other less-dense components in the mixture. The force that is applied to the mixture is a function of the speed of the centrifuge rotor, and the radius of the spin. In most applications, the force of the spin will result in a precipitate (a pellet) to gather at the bottom of the centrifuge tube, where the remaining solution is properly called a "supernate" or "supernatant." In other similar applications, a density-based separation or "gradient centrifugation" technique is used to isolate a particular species from a mixture that contains components that are both more dense and less dense than the desired component.

During the circular motion of a centrifuge rotor, the force that is applied is the product of the radius and the angular velocity of the spin, where the force is traditionally expressed as an acceleration relative to "g," the standard acceleration due to gravity at the Earth's surface. The centrifugal force that is applied is termed the "relative centrifugal force" (RCF), and is expressed in multiples of "g."

Comminute (comminution and comminuting): The process of reducing larger particles into smaller particles, including, without limitation, by grinding, blending, shredding, slicing, milling, cutting, shredding. ECM can be comminuted while in any form, including, but not limited to, hydrated forms, frozen, air-dried, lyophilized, powdered, sheet-form.

Contacting: Placement in direct physical association, which can be in solid or liquid form.

Cytokine: The term "cytokine" is used as a generic name for a diverse group of soluble proteins and peptides that act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to, tumor necrosis factor-α, interleukin (IL)-6, IL-10, IL-12, transforming growth factor, and interferon-γ.

Diagnosis: The process of identifying a disease by its signs, symptoms and results of various tests. The conclusion reached through that process is also called "a diagnosis." Forms of testing commonly performed include blood tests, medical imaging, and biopsy.

Extracellular Matrix (ECM): A natural acellular scaffolding for cell growth. Natural ECMs (ECMs found in multicellular organisms, such as, but not limited to, mammals and humans) are complex mixtures of structural and non-structural biomolecules, including, but not limited to, collagens, elastins, laminins, glycosaminoglycans, proteoglycans, antimicrobials, chemoattractants, cytokines, and growth factors. In mammals, ECM often comprises about 90% collagen, in its various forms. The composition and structure of ECMs vary depending on the source of the tissue. For example, small intestinal submucosa (SIS), urinary bladder matrix (UBM), esophagus (E) and liver stroma ECM each differ in their overall structure and composition due to the unique cellular niche needed for each tissue. An intact "extracellular matrix" and "intact ECM" is an extracellular matrix that retains activity of its structural and non-structural biomolecules, including, but not limited to, collagens, elastins, laminins, glycosaminoglycans, proteoglycans, antimicrobials, chemoattractants, cytokines, and growth factors.

The structure and/or activity of the biomolecules within the ECM can be altered or removed chemically or mechanically, for example, by cross-linking and/or by dialyzing the ECM. Intact ECM essentially has not been enzymatically digested, cross-linked and/or dialyzed, meaning that the ECM has not been subjected to a digestion, dialysis and/or a cross-linking process, or conditions other than processes that occur naturally during storage and handling of ECM prior to solubilization. Thus, ECM that is substantially cross-linked and/or dialyzed (in anything but a trivial manner which does not substantially affect the gelation and functional characteristics of the ECM in its uses described herein) is not considered to be "intact." "Acellular" refers to ECM produced from a source tissue that has been treated to remove the cells such that the ECM remains. Decellularized tissue is used to produce ECM hydrogels.

Gel: A state of matter between liquid and solid, and is generally defined as a cross-linked polymer network swollen in a liquid medium. Typically, a gel is a two-phase colloidal dispersion containing both solid and liquid, wherein the amount of solid is greater than that in the two-phase colloidal dispersion referred to as a "sol." As such, a "gel" has some of the properties of a liquid (i.e., the shape is resilient and deformable) and some of the properties of a solid (for example, the shape is discrete enough to maintain three dimensions on a two dimensional surface). "Gelation time," also referred to as "gel time," refers to the time it takes for a composition to become non-flowable under modest stress.

Gelation: The formation of a gel from a sol.

Hemostasis: The inhibition or halting of hemorrhage.

Hydrogel: A network of polymer chains that are hydrophilic, sometimes found as a colloidal gel in which water is the dispersion medium. Hydrogels are highly absorbent natural or synthetic polymeric networks. Hydrogels also possess a degree of flexibility similar to natural tissue. An "acoustic" hydrogel, such as an acoustic ECM hydrogel, is produced using ultrasound energy. The characteristics of these hydrogels are disclosed herein. For a hydrogel, the G' (storage modulus) is typically about an order of magnitude greater than the G" (loss modulus).

Isolated: An "isolated" biological component (such as extracellular matrix) has been substantially separated, produced apart from, or purified away from other biological components, cells or the organism in which the component naturally occurs, i.e., live cells, other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids. An isolated ECM has been separated from cells that produce the ECM.

Isotonic Buffered Solution: A solution that is buffered to a pH between 7.2 and 7.8 and that has a balanced concentration of salts to promote an isotonic environment.

Macrophage: A type of white blood cell that phagocytoses and degrades cellular debris, foreign substances, microbes, and cancer cells. In addition to their role in phagocytosis, these cells play an important role in development, tissue maintenance and repair, and in both innate and adaptive immunity in that they recruit and influence other cells including immune cells such as lymphocytes. Macrophages can exist in many phenotypes, including phenotypes that have been referred to as M1 and M2, also called "M1-like" and "M2-like." Macrophages that perform primarily pro-inflammatory functions are called M1 macrophages (CD86+/CD68+), whereas macrophages that decrease inflammation and encourage and regulate tissue repair are called M2 macrophages (CD206+/CD68+). The markers that identify the various phenotypes of macrophages vary among species. It should be noted that macrophage phenotype is represented by a spectrum that ranges between the extremes of M1 and M2.

Mammal: This term includes both human and non-human mammals. Similarly, the term "subject" includes both human and veterinary subjects.

Preventing or treating a disease: "Preventing" a disease refers to inhibiting the partial or full development of a disease, for example in a person who is known to have a predisposition to a disease such as a cancer. An example of a person with a known predisposition is someone with a history of breast cancer in the family, or who has been exposed to factors that predispose the subject to a condition, such as melanoma. "Treatment" refers to a therapeutic intervention that ameliorates a sign or symptom of a disease or pathological condition after it has begun to develop. In several embodiments, treatment refers to a reduction in size of a tumor, a decrease in the number and/or size of metastases, or a decrease in a symptom of the tumor.

Therapeutic agent: Used in a generic sense, it includes treating agents, prophylactic agents, and replacement agents. "Treatment" or "treating" means providing a substance, such as an acoustic ECM hydrogel, to a patient in an amount sufficient to measurably affect a biological parameter, such as to increase hemostasis.

Therapeutically effective amount: A "therapeutically effective amount" of a composition, such as an acoustic ECM hydrogel, means an amount effective, when administered to a patient, to provide a therapeutic benefit such as an amelioration of symptoms, reduced decrease progression, or cause disease regression. A quantity of an acoustic ECM hydrogel is sufficient to achieve a desired effect in a subject being treated. A therapeutically effective amount can be administered systemically or locally, such as to a wound. In addition, an effective amount of an acoustic ECM hydrogel can be administered in a single dose, or in several doses over time. However, the effective amount will be dependent on the preparation applied, the subject being treated, the severity and type of the affliction, and the manner of administration of the compound. The acoustic ECM hydrogels of use in the methods disclosed herein have equal applications in medical and veterinary settings. Therefore, the general term "subject" or "patient" is understood to include all animals, including, but not limited to, humans or veterinary subjects, such as other primates, dogs, cats, horses, and cows.

Thermoreversible hydrogel: Hydrogel formed due to entanglement of polymer chains wherein the viscosity changes at a characteristic temperature of gelation. The disclosed acoustic ECM hydrogels are thermoreversible hydrogels that show gelation (sol to gel transition) upon cooling.

Topical application: A topically applied agent is applied only in a specific area, and not throughout the body. In particular examples the composition is applied to the skin or the eye in an area where hemostasis is desired. For example the pharmaceutical composition can be applied in a topical preparation to a wound, such as an epithelial wound or defect, for example a traumatic or surgical wound, such as a skin or corneal abrasion or surgical incision.

Ultrasonication: The process of exposing ultrasonic waves with a frequency higher than 20 kHz.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. "About" indicates within 5% of a listed value. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Extracellular Matrix (ECM)

Any type of extracellular matrix tissue can be used to produce a hydrogel (see U.S. Pat. Nos. 4,902,508; 4,956, 178; 5,281,422; 5,352,463; 5,372,821; 5,554,389; 5,573, 784; 5,645,860; 5,771,969; 5,753,267; 5,762,966; 5,866, 414; 6,099,567; 6,485,723; 6,576,265; 6,579,538; 6,696, 270; 6,783,776; 6,793,939; 6,849,273; 6,852,339; 6,861, 074; 6,887,495; 6,890,562; 6,890,563; 6,890,564; and 6,893,666 related to ECM). In certain embodiments, the ECM is isolated from a vertebrate animal, for example and without limitation, from a warm-blooded mammalian vertebrate animal including, but not limited to, humans, monkeys, horses, pigs, cows and sheep. In specific non-limiting examples, the ECM is porcine or human.

The ECM can be derived from any organ or tissue, including without limitation, urinary bladder, intestine (such as small intestine or large intestine), heart, kidney, uterus, brain, blood vessel, lung, bone muscle, pancreas, stomach, spleen adipose tissue, liver, esophagus and dermis. The ECM can be obtained from a cell culture. In one embodiment, the ECM is isolated from a urinary bladder. In another embodiment, the ECM is from an esophagus. In another embodiment, the ECM is from dermis. The ECM may or may not include the basement membrane portion of the ECM. In certain embodiments, the ECM includes at least a portion of the basement membrane. A tissue can be decellularized to remove cells and cellular material, e.g., from the source tissue or organ, to produce an ECM. It desirable to use a decellularized material prevent an immune response, such as when ECM is implanted in a subject, for example, as a component of a hydrogel disclosed herein. Removal of cellular material, such as when using ECM to form a hydrogel, prevents such an immune response.

U.S. Pat. No. 8,361,503 (incorporated herein by reference) discloses preparation of a urinary bladder ECM, such as porcine bladder ECM is prepared by abrading bladder tissue to remove the outer layers including both the tunica serosa and the tunica muscularis using a longitudinal wiping motion with a scalpel handle and moistened gauze. Following eversion of the tissue segment, the luminal portion of the tunica mucosa is delaminated from the underlying tissue using the same wiping motion. In some embodiments, perforation of the submucosa is prevented. After these tissues are removed, the resulting ECM consists mainly of the tunica submucosa.

The production of hydrogels from dermal ECM is disclosed in Wolf et al., Biomaterials 33: 7028-7038, 2012, incorporated herein by reference. The production of ECM from esophageal tissue is disclosed, for example, in Badylak et al. J Pediatr Surg. 35(7):1097-103, 2000 and Badylak et al., J Surg Res. 2005 September; 128(1):87-97, 2005, both incorporated herein by reference. U.S. Pat. No. 6,893,666, incorporated herein by reference, discloses production of ECM from urinary bladder, skin, esophagus and small intestine. ECM can be produced from any of these tissues.

Commercially available ECM preparations can also be used. In one embodiment, the ECM is derived from small intestinal submucosa or SIS. Commercially available preparations include, but are not limited to, SURGISIS™, SURGISIS-ES™, STRATASIS™, and STRATASIS-ES™ (Cook Urological Inc.; Indianapolis, Ind.) and GRAFTPATCH™ (Organogenesis Inc.; Canton Mass.). In another embodiment, the ECM is derived from dermis. Commercially available preparations include, but are not limited to PELVICOL™ (sold as PERMACOL™ in Europe; Bard, Covington, Ga.), REPLIFORM™ (Microvasive; Boston, Mass.) and ALLODERM™ (LifeCell; Branchburg, N.J.). In another embodiment, the ECM is derived from urinary bladder. Commercially available preparations include, but are not limited to UBM (Acell Corporation; Jessup, Md.).

Tissue for preparation of ECM can be harvested in a large variety of ways and once harvested, a variety of portions of the harvested tissue may be used. ECM has also been prepared from the esophagus and small intestine, see, for example, Keane et al., Tissue Eng. Part A, 21(17-18): 2293-2300, 2015, incorporated herein by reference. Esophageal ECM can be prepared by mechanically separating the mucosa and submucosa from the muscularis externa and digesting the mucosal layers in a buffer including trypsin, followed by exposure to sucrose, TRITON-X100®, deoxycholic acid, peracetic acid and DNAse. Small intestine submucosa (SIS) can be prepared by mechanically removing the superficial layers of the tunica mucosa, tunica serosa, and tunica muscularis externa from the intact small intestine, leaving the submucosa, muscularis mucosa, and basilar stratum compactum intact. The SIS is then treated with peracetic acid. Exemplary protocols are provided in Keane et al. Dermal hydrogels can be produced, for example, as disclosed in Wolf et al, *J Biomed Mater Res* A. 2013. 35(25):6838-49. PMID: 23873846. PMCID: 3808505, incorporated herein by reference.

In one embodiment, the ECM is isolated from harvested porcine urinary bladder to prepare urinary bladder matrix (UBM). Excess connective tissue and residual urine are removed from the urinary bladder. The tunica serosa, tunica muscularis externa, tunica submucosa and most of the muscularis mucosa can be removed by mechanical abrasion or by a combination of enzymatic treatment, hydration, and abrasion. Mechanical removal of these tissues can be accomplished by abrasion using a longitudinal wiping motion to remove the outer layers (particularly the abluminal smooth muscle layers) and even the luminal portions of the tunica mucosa (epithelial layers). Mechanical removal of these tissues is accomplished by removal of mesenteric tissues with, for example, Adson-Brown forceps and Metzenbaum scissors and wiping away the tunica muscularis and tunica submucosa using a longitudinal wiping motion with a scalpel handle or other rigid object wrapped in moistened gauze. The epithelial cells of the tunica mucosa can also be dissociated by soaking the tissue in a de-epithelializing solution, for example and without limitation, hypertonic saline. The resulting UBM comprises basement membrane of the tunica mucosa and the adjacent tunica propria, which is further treated with peracetic acid, lyophilized and powdered, see U.S. Pat. No. 8,361,503, incorporated herein by reference.

Dermis sections can used for the preparation of the ECM hydrogels, see PCT Application No. 2015/15164728, incorporated herein by reference. In a specific non-limiting example, the dermis can be decellularized with 0.25% Trypsin/1% TRITON-X®-100 (i.e. no SDS) on a vortex shaker at 300 RPM at room temperature in the following solutions: 0.25% trypsin for 6 hours, 1×; deionized water, 15 minutes, 3×; 70% ethanol, 10 to 12 hours, 1×; 3% $H_2O_2$, 15 minutes, 1×, deionized water, 15 minutes, 2×; 1% TRITON-X®-100 in 0.26% EDTA/0.69% Tris, 6 hours, 1× and then overnight, 1×; deionized water, 15 minutes, 3×; 0.1% peracetic acid/4% ethanol, 2 hours, 1×; PBS, 15 minutes, 2×; and finally deionized water, 15 minutes, 2×. Dermis sheets are then lyophilized and subsequently reduced to particulate form using a Waring blender and a Wiley Mill with a #20 mesh screen.

In some embodiments, the epithelial cells can be delaminated first by first soaking the tissue in a de-epithelializing solution such as hypertonic saline, for example and without limitation, 1.0 N saline, for periods of time ranging from 10 minutes to 4 hours. Exposure to hypertonic saline solution effectively removes the epithelial cells from the underlying basement membrane. The tissue remaining after the initial delamination procedure includes epithelial basement membrane and the tissue layers abluminal to the epithelial basement membrane. This tissue is next subjected to further treatment to remove the majority of abluminal tissues but not the epithelial basement membrane. The outer serosal, adventitial, smooth muscle tissues, tunica submucosa and most of the muscularis mucosa are removed from the remaining de-epithelialized tissue by mechanical abrasion or by a combination of enzymatic treatment, hydration, and abrasion.

ECM can be sterilized by any number of standard techniques, including, but not limited to, exposure to peracetic acid, low dose gamma radiation, gas plasma sterilization, ethylene oxide treatment or electron beam treatment. More typically, sterilization of ECM is obtained by soaking in 0.1% (v/v) peracetic acid, 4% (v/v) ethanol, and 95.9% (v/v) sterile water for two hours. The peracetic acid residue is removed by washing twice for 15 minutes with PBS (pH=7.4) and twice for 15 minutes with sterile water. ECM material can be sterilized by propylene oxide or ethylene oxide treatment, gamma irradiation treatment (0.05 to 4 mRad), gas plasma sterilization, peracetic acid sterilization, or electron beam treatment. The ECM can also be sterilized by treatment with glutaraldehyde, which causes cross linking of the protein material, but this treatment substantially alters the material such that it is slowly resorbed or not resorbed at all and incites a different type of host remodeling which more closely resembles scar tissue formation or encapsulation rather than constructive remodeling. Cross-linking of the protein material can also be induced with carbodiimide or dehydrothermal or photooxidation methods. As disclosed in U.S. Pat. No. 8,361,503, ECM is disinfected by immersion in 0.1% (v/v) peracetic acid (a), 4% (v/v) ethanol, and 96% (v/v) sterile water for 2 h. The ECM material is then washed twice for 15 min with PBS (pH=7.4) and twice for 15 min with deionized water.

Generally, following isolation of the tissue of interest, decellularization is performed by various methods, for example and without limitation, exposure to hypertonic saline, peracetic acid, TRITON-X® or other detergents. Sterilization and decellularization can be simultaneous. For example and without limitation, sterilization with peracetic acid, described above, also can be used for decellularization. ECM can then be dried, either lyophilized (freeze-dried) or air dried. Dried ECM can be comminuted by methods including, but not limited to, tearing, milling, cutting, grinding, and shearing. The comminuted ECM can also be further processed into a powdered form by methods, for example and without limitation, such as grinding or milling in a frozen or freeze-dried state.

Mammalian ECM is also commercially available. These include AVITENE™ MICROMATRIX® and XENMATRIX™.

Acoustic ECM Hydrogels and their Preparation

In some embodiments, a comminuted ECM, such as a mammalian ECM, is diluted in a liquid. The ECM may or may not be lyophilized prior to comminuting. The ECM can be comminuted, for example, by grinding, chopping or cutting the ECM. Comminuted ECM should have pieces in the range of about 10 µm to about 5000 µm, about 10 µm to about 4000 µm, about 10 µm to about 3000 µm, about 10 µm to about 2000 µm, about 10 µm to about 1000 µm, about 10 µm to about 500 µm, about 30 µm to about 300 µm, about 40 to about 400 µm, about 25 µm to about 500 µm, about 50 µm to about 500 µm, about 100 µm to about 300 µm, about 10 µm to about 50 µm, or about 10 µm to about 100 µm. In one embodiment, the ECM is provided in pieces having a range from about 10 µm to about 1000 µm. In another preferred embodiment, the ECM is provided in pieces having a range from about 10 µm to about 2000 µm. In one non-limiting example, the pieces are in the range of about 30 µm to about 300 µm. The liquid can be a buffer at neutral pH, such as, for example, a pH of about 7.0 to about 7.6, such as about 7.1 to about 7.5, such as about 7.2 to about 7.4, such as about 7.0 to 7.2, such as about 7.0 to 7.4, such as about 7.1, 7.2, 7.3, 7.4, 7.5 or 7.6. The ECM can be diluted in an isotonic buffered saline solution, such as, but not limited to, phosphate buffered saline (PBS) or Tris buffered saline. In some embodiments, the buffered saline solution has an osmolarity of about 290 mOsm/L. The liquid can be water. In some embodiments, the isotonic buffer, including, without limitation, Phosphate Buffered Saline (PBS), can be used to bring the solution to a target pH, or to aid in maintaining the pH and ionic strength of the gel to target levels, such as physiological pH and ionic conditions. This forms a liquid ECM solution.

The disclosed methods generally do not involve the use of an acid protease, including pepsin, trypsin, or hyaluronidase. See PCT Application No. WO 2015/164728, incorporated herein by reference. Generally, in the present methods, the solubilized ECM in the liquid is not contacted with an acid protease.

In some embodiments, the ECM is utilized at a concentration of greater than about 25 mg/ml in the liquid. The ECM can be utilized at a concentration of about 25 mg/ml to about 600 mg/ml in the liquid, such as the buffer. Suitable concentrations also include about 25 mg/ml to about 300 mg/ml, about 25 mg/ml to about 200 mg/ml, and about 25 mg/ml to about 150 mg/ml. The ECM can be utilized at a concentration of about 50 mg/ml to 600 mg/ml in the liquid, such as the buffer. Suitable concentrations also include about 50 mg/ml to about 300 mg/ml, about 50 mg/ml to about 200 mg/ml, and about 50 mg/ml to about 150 mg/ml. Suitable concentrations include about 25, 30, 35, 40, 45, 50, 55, 60, 65, 70, 75, 80, 85, 90, 95, 100, 105, 110, 115, 120, 125, 130, 135, 140, 150, 155, 160, 165, 170, 175, 180, 185, 190, 195, and 200 mg/ml. Exemplary concentrations include about 25 mg/ml, 100 mg/ml, and 150 mg/ml. In one non-limiting example, the ECM in a liquid at a concentration of about 25 mg/ml to about 150 mg/ml. In one non-limiting example, the ECM is in the liquid at a concentration of 100 mg/ml.

The ECM in the liquid, such as the buffered saline solution, is treated with an ultrasound frequency. In one embodiment, the ultrasound is at a frequency of about 20 kHz to about 100 kHz. The ECM in the liquid can be treated with ultrasound at a frequency of about 20 kHz to about 30 kHz, about 20 Hz to about 40 kHz, about 20 kHz to about 50 kHz, about 20 kHz to about 60 kHz, about 20 kHz to about 70 kHz, about 20 kHz to about 80 kHz, or about 20 kHz to about 90 kHz. The ECM in the liquid can be treated with ultrasound at a frequency of about 20 kHz, 30 kHz, 40 kHz, 50 kHz, 60 kHz, 70 kHz, 80 kHz, 90 kHz or 100 kHz. In one non-limiting example, the ECM in the liquid can be treated with ultrasound at a frequency of about 20 kHz.

The ECM in the liquid, such as the buffered saline solution, is treated with ultrasound for at least 20 seconds, such as at least 30 seconds. The ECM in the liquid, such as the buffered saline solution, is treated with ultrasound for at least 60 seconds. In some embodiments, the ECM in the liquid is treated with ultrasound for at least 60 seconds to about one hour. In further embodiments, the ECM in the liquid is treated with ultrasound for at least 60 seconds to about 30 minutes. In further embodiments, the ECM in the liquid is treated with ultrasound for at least 30 seconds to about 30 minutes. In more embodiments, the ECM in the liquid is treated with ultrasound for at least 60 seconds to about 15 minutes. In more embodiments, the ECM in the liquid is treated with ultrasound for at least 30 seconds to about 15 minutes. In some embodiments, the ECM in the liquid is treated with ultrasound for at least 60 seconds to about 10 minutes. In some embodiments, the ECM in the liquid is treated with ultrasound for at least 30 seconds to about 10 minutes. In some embodiments, the ECM in the liquid is treated with ultrasound for at least 60 seconds to about 5 minutes. In some embodiments, the ECM in the liquid is treated with ultrasound for at least 30 seconds to about 5 minutes. The ECM in the liquid can treated with ultrasound for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes. In some embodiments, the ECM in the liquid is treated with the ultrasound in pulses for a total time as listed herein. Thus, in some embodiments, the ECM in the liquid, such as the buffered saline solution, is treated with pulses, such as of at least about 30 seconds in length, such as about 30, about 40 or about 60 seconds in length. The ECM in the liquid such as the buffered saline solution, can be treated 1, 2, 3, 4, 5, 6, 7, 8, 9, 10 times, with the ultrasound, such that the total time of treatment is the 60 seconds to one hour, or any of the total times listed. The ECM in the liquid such as saline solution can be treated for 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 seconds. The ECM in the liquid such as saline solution can be treated for at least 30 seconds. Generally, if multiple treatments are used, they occur in a period of less than 1 hour. An exemplary method is pulses of 30 seconds of ultrasound, followed by no treatment for 30 to 45 seconds, followed by another treatment. This treatment is applied 2, 3, 4, 5, 6, 7, 8, 9 or 10 or more times. One exemplary non-limiting method is six pulses of 30 seconds of ultrasound, such as at about 20 kHz, followed by 45 seconds off, for six repetitions, totaling 3 minutes of treatment with ultrasound.

The ultrasound can have an amplitude of about 20 μm to about 320 μm. Generally, the amplitude is measure from the center of the probe used to produce the ultrasound. The amplitude of the probe's vibrating surface the distance between its position in the probe's fully extended and fully contracted states, measured in microns (μm). In some embodiments, the amplitude is about 30 μm to about 200 μm. In further embodiments, the amplitude is about 36 μm to about 180 μm. The amplitude can be about 30, 40, 50, 60, 70, 80, 90, 100, 110, 120, 130, 140, 150, 150, 160, 70, 180, 190, 200, 210, 220, 230, 240, 250, 260, 270, 280, 290 or 300 μm. In some embodiments, the amplitude can be about 30-40 μm, 40-50 μm, 50-60 μm, 60-70 μm, 70-80 μm, 80-90 μm, 90-100 μm, 100-110, 110-120 μm, 120-130 μm, 130-140 μm, 140-150 μm, 150-160 μm, 160-170 μm, 170-180 μm, 180-190 μm, 190-200 μm, 200-210 μm, 210-220 μm 220-230 μm, 230-240 μm, 240-250 μm, 250-260 μm, 260-270 μm, 270-280 μm, 280-290 μm or 290-300 μm. In one specific, non-limiting example, the ultrasound is at a frequency of about 20 kHz, and the amplitude is about 36 μm to about 180 μm. In a further non-limiting example, the ultrasound is at a frequency of about 20 kHz, and the amplitude is about 36 μm to about 180 μm, and the treatment is for a total of about 1, 2, 3, 4, or 5 minutes, such as about 3 minutes. The sonication can be for about 1, 2, 3, 4, 5, 6, 7, 8, 9, 10, 11, 12, 13, 14, 15, 16, 17, 18, 19 or 20 minutes. The sonication can be from about 30 seconds to about 5 minutes. The sonication can be for example, for between about 1 to about 5 minutes. The sonication can be for about 1 to about 10 minutes. The sonication can be, for example, for between 1 to about 20 minutes. In more embodiments, the sonication can be for less than about one hour, less than about 30 minutes, less than about 20 minutes, or less than about 10 minutes. In some embodiments, the sonication can be for at least 30 seconds. In other embodiments, the sonication can be for about 10 minutes to about 24 hours, for example, about 1, 2, 3, 4, 5, 6, 7, 8, 9, 10, 11, 12, 13, 14, 15, 16, 17, 18, 19, 20, 21, 22, 23, or 24 hours. In some embodiments, sonication can be for up to 48 hours.

In some embodiments, the ECM in the liquid is treated with the ultrasound at a temperature in a range of about 30° C. to about 43° C. In one embodiment, the ECM in the liquid is treated with the ultrasound at a temperature in the range of about 35° C. to about 40° C. In one embodiment, the ECM in the liquid is treated with ultrasound at a temperature in the range of about 36° C. to about 38° C. In another embodiment, the ECM in the liquid is treated with ultrasound at a temperature in the range of about 37° C. or greater, such as a temperature of about 37° C. to about 55° C., such as about 37° C. to about 50° C., such as about 37° C. to about 45° C., such as about 37° C. to about 40° C. The ECM in the liquid is treated with the ultrasound at a temperature of about 37, 38, 39, 40, 41, 42, 43, 44, 45, 46, 47, 48, 49, 50, 51, 52, 53, 54, or 55° C. In further embodiment, the ECM in the liquid is treated with the ultrasound at greater than about 38° C., such as about 38° C. to about 50° C., such as about 38° C. to about 45° C., such as about 38° C. to about 40° C.

Treatment with ultrasound produces an acoustic ECM hydrogel. The acoustic ECM hydrogel generally experiences a phase transition from sol to gel around 37° C. and is therefore transitions to a liquid phase at greater than 37° C., and to a gel phase at below 37° C. At 37° C. the acoustic ECM hydrogel is sufficiently viscous to resemble a gel, however as the temperature is increased above 37° C., the gel transitions to a sol. The acoustic ECM hydrogel forms a gel (sol to gel transition) upon a decrease in temperature below 37° C. Thus, in some embodiments, following sonication, the acoustic ECM hydrogel is cooled to a temperature of less than 37° C., such as about 4° C. to about 36° C. The acoustic ECM hydrogel can be cooled to room temperature, which is generally about 25° C. In some embodiments, the acoustic ECM hydrogel is cooled to about 15° C. to about 25° C. The acoustic ECM hydrogel can be cooled to about 23° C. to about 27° C. The acoustic ECM hydrogel can be cooled to about 4, 5, 6, 7, 8, 9, 10, 11, 12, 13, 14, 15, 16, 17, 18, 19, 20, 21, 22, 23, 24, 25, 26, 27, 28 29 or 30° C. to induce the gel phase.

In some embodiments, disclosed is an acoustic mammalian ECM hydrogel, wherein the hydrogel is thermoreversible, wherein the hydrogel is in a solid (gel) phase at temperatures below about 37° C. and is in a liquid (sol) phase at temperatures of greater than 37° C. The acoustic hydrogel can be produced using any of the methods disclosed herein. In some embodiments, the storage modulus (G') is greater than loss modulus (G") by about an order of magnitude for the acoustic ECM hydrogel. In further embodiments, wherein the viscosity of the acoustic ECM hydrogel decreases with increased stress at a temperature of about 15 to about 37° C., such as at about 15, 15, 16, 17, 18, 20, 21, 22, 23, 24, 25, 26, 27, 28, 29, 30, 31, 32, 33, 34, 35, and/or 36° C. In further embodiments, the viscosity of the acoustic ECM hydrogel decreases with increased stress at room temperature, and/or at about 23° C. to about 27° C. and/or about 15° C. to about 25° C. In one embodiment, the gel to sol transition of the acoustic ECM hydrogel is at about 37° C., such that the hydrogel can be used as a submucosal cushion because it is sufficiently viscous at body temperature.

These acoustic ECM hydrogels can be made from any mammalian ECM disclosed above. In specific, non-limiting example, the ECM is human ECM. In other non-limiting examples, the ECM is urinary bladder ECM, small intestinal submucosal ECM, esophageal EMC, or dermal ECM. In one embodiment, the ECM is urinary bladder ECM. In another embodiment, the ECM is dermal ECM. In yet another embodiment, the ECM is esophageal ECM. The source of ECM may be, for example, porcine, bovine, or ovine.

In some embodiments, the acoustic ECM hydrogel includes ECM at a concentration of about 25 mg/ml to about 600 mg/ml. In further embodiments, the acoustic ECM hydrogel includes ECM at a concentration of about 20 mg/ml to about 600 mg/ml, about 25 mg/ml to about 300 mg/ml, about 25 mg/ml to about 200 mg/ml, and about 25 mg/ml to about 150 mg/ml. In more embodiments, the acoustic ECM hydrogel includes ECM at a concentration of about 50 mg/ml to 600 mg/ml in the liquid, such as in the buffer. The acoustic ECM hydrogel also can have an ECM concentration of about 50 mg/ml to about 300 mg/ml, about 50 mg/ml to about 200 mg/ml, about 50 mg/ml to about 150 mg/ml, about 50-100 mg/ml, or about 100-150 mg/ml. In some non-limiting examples, the acoustic ECM hydrogel includes ECM at a concentration of about 20, 25, 30, 35, 40, 45, 50, 55, 60, 65, 70, 75, 80, 85, 90, 95, 100, 105, 110, 115, 120, 125, 130, 135, 140, 150, 155, 160, 165, 170, 175, 180, 185, 190, 195, and 200 mg/ml. In some non-limiting examples, the acoustic ECM hydrogel includes ECM at a concentration of about 20-25, 25-30, 30-35, 35-40, 40-45, 45-50, 50-55, 55-60, 60-65, 65-70, 70-75, 75-80, 80-85, 85-90, 90-95, 95-100, 100-105, 105-110, 110-115, 115-120, 120-125, 125-130, 130-135, 135-140, 140-145, 145-150, 150-155, 155-160, 160-165, 165-170, 170-175, 175-180, 180-185, 185-190, 190-195, and 195-200 mg/ml. Exemplary non-limiting concentrations of ECM also include about 25 mg/ml, 100 mg/ml, and 150 mg/ml. In one non-limiting example, the acoustic ECM hydrogel includes ECM at a concentration of about 25 mg/ml to about 150 mg/ml. In one embodiment, the ECM concentration is about 100 mg/ml.

In some embodiments, wherein the acoustic ECM hydrogel a viscosity of about 1400 Pa*s at 15° C., and a viscosity of about 400 Pa*s at a temperature of 25° C., when the concentration of ECM is about 150 mg/mL. In other embodiments, the acoustic ECM hydrogel has a storage modulus of approximately 2700 Pa*s at 15° C., approximately 800 Pa*s at 25° C., and 600 Pa*s at 37° C., when the concentration of ECM is about 150 mg/mL.

Figure 1C:
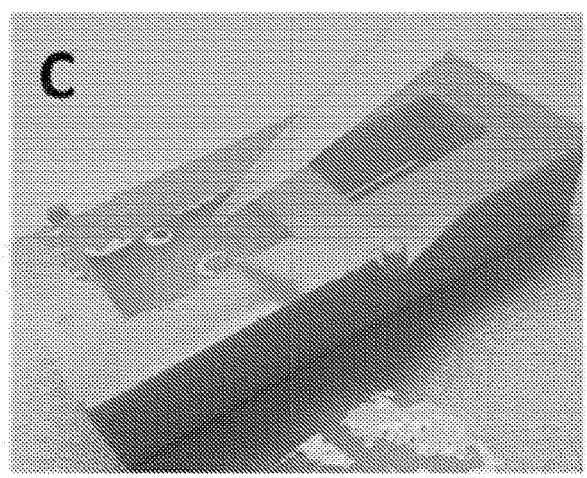
Figure 1D:
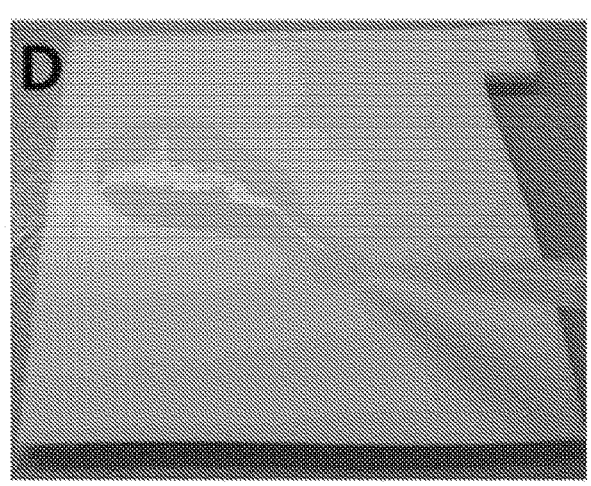
Figure 2A:
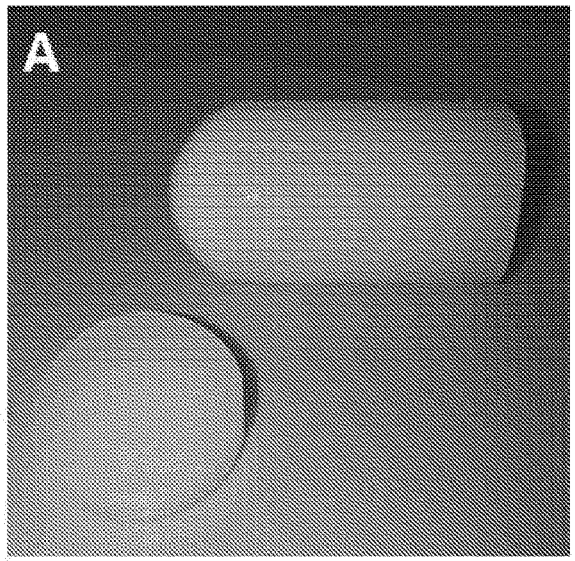
FIGS. 2A-2D: Representative images of acoustic ECM hydrogels, lyophilized gels, ultrathin ECM sheets and ECM putty. (A) Acoustic ECM hydrogel cast as a cylinder. (B) Lyophilized acoustic ECM hydrogels maintain their 3D configuration. (C) Ultrathin acoustic ECM sheet prepared by casting ECM gel on a Teflon sheet. (D) ECM putty prepared by sonication of ECM at concentrations below 25 mg/ml.
Figure 2B:
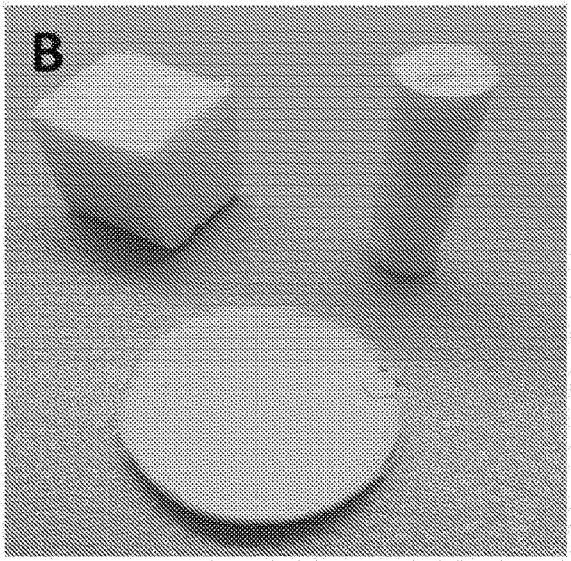
Figure 2C:
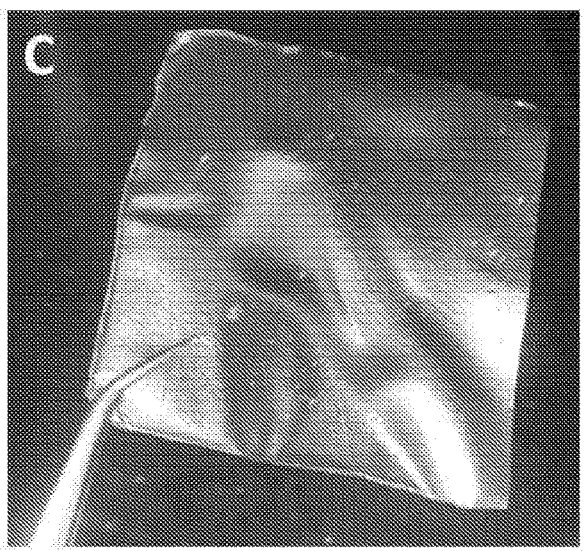
Figure 2D:
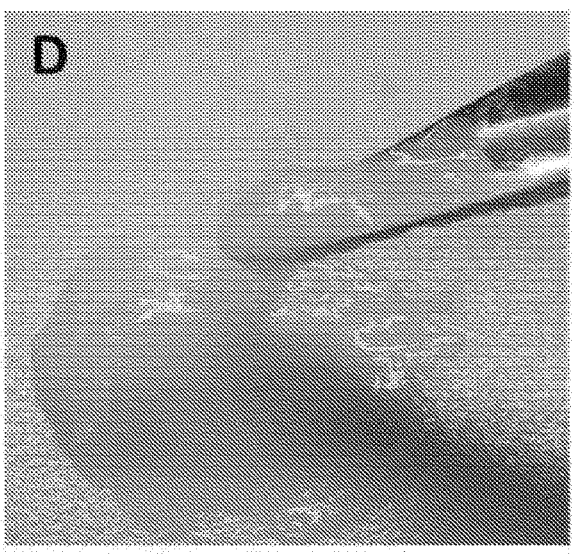

The acoustic ECM hydrogel in the liquid phase, can be placed into a three-dimensional cast prior to cooling, or spread on a TEFLON® sheet to form a film, see, for example, FIGS. 1C and 1D. The high concentration of ECM in (50 to 600 mg/ml) in the acoustic ECM hydrogel allows for the formation of very thin sheets, for example a sheet as thin as 4 microns. The acoustic ECM hydrogel can be configured to any size greater than 4 microns and in any 2-dimensional or 3-dimensional shape. In some embodiments, a sheet is formed that is about 4 to about 10 microns in thickness, such as about 4, 5, 6, 7, 8, 9, or 10 microns in thickness. The acoustic ECM hydrogel can be formed into any three-dimensional shape, which includes, without limitation a cylinder, sphere, ellipsoid, disk, sheet, cube, cuboid, cone, triangular or rectangular prism, as well as hollow spheres, hollow ellipsoids, and open-ended hollow cylinders, etc. Exemplary shapes are shown in FIGS. 2A-2C. The acoustic ECM hydrogel can also be used as an injectable, such as by placing it in a syringe and extruding it from the syringe in either a gel or sol phase.

In some embodiments, the acoustic ECM hydrogel is absorbed into, adsorbed onto, or otherwise dispersed onto or into a biocompatible substrate. Non-limiting examples of a biocompatible substrate include: a mesh, a non-woven, decellularized tissue, a polymer composition, a polymeric structure, a cell growth scaffold, an implant, an orthopedic implant, and intraocular lens, sutures, intravascular implants, stents, and transplants. In some embodiments, the substrate is synthetic. In other embodiments, the substrate is natural. The acoustic ECM hydrogel can be applied to or incorporated into, by any suitable method, a non-woven material, such as a bandage, a suture, an implant, such as a ceramic, metal, or polymeric implant, for example a prosthesis, artificial or otherwise-modified vessel, a valve, an intraocular lens, or a tissue implant. As used herein, the term "coat", and related cognates such as "coated" and "coating," refers to a process comprising of covering, in part or in whole, an inorganic structure with a composition described herein. For example and without limitation, coating of an inorganic structure with an acoustic ECM hydrogel, in the liquid phase, can include methods such as pouring, embedding, layering, dipping, spraying.

In another embodiment, the composition including the acoustic ECM hydrogel is coated, in the liquid phase, onto a biocompatible structural material, such as a metal, an inorganic calcium compound such as calcium hydroxide, calcium phosphate or calcium carbonate, or a ceramic composition. Non-limiting examples of suitable metals are cobalt-chrome alloys, stainless steel alloys, titanium alloys, tantalum alloys, titanium-tantalum alloys, which can include both non-metallic and metallic components, such as molybdenum, tantalum, niobium, zirconium, iron, manganese, chromium, cobalt, nickel aluminum and lanthanum, including without limitation, CP Ti (commercially pure titanium) of various grades or Ti 6Al 4V (90% wt. Ti, 6% wt. Al and 4% wt. V), stainless steel 316, Nitinol (Nickel-titanium alloy), titanium alloys coated with hydroxyapatite. Metals are useful due to high strength, flexibility, and biocompatibility. Metals also can be formed into complex shapes and many can withstand corrosion in the biological environments, reduce wear, and not cause damage to tissues. Other compositions, including ceramics, calcium compounds, such as, without limitation, aragonite. Combinations of metal, ceramics and/or other materials also can be of use.

Any useful agent can be mixed into, co-delivered, co-applied or otherwise combined with any composition as described herein. For example, and without limitation, useful agents include interferons, interleukins, chemokines, monokines, hormones, coagulants, chemotherapeutics and antibiotics.

Methods of Use

Macrophages have been shown to be important regulators of normal healing following injury, and in normal tissue development. The disclosed acoustic ECM hydrogels can recapitulate the effects of whole ECM on macrophage phenotype, leading to an increase in M2-like, regulatory, or pro-remodeling macrophages. Thus, any of the compositions disclosed herein can be used for modifying macrophage phenotype, such as for inducing regulatory M2 macrophages.

In some embodiments, methods are disclosed for inducing M2 macrophages in a subject by administering a therapeutically effective amount of a composition including the acoustic ECM hydrogel, as disclosed herein, thereby inducing M2 macrophages in the subject. In further embodiments, methods are disclosed for decreasing M1 (proinflammatory) macrophages in a subject. The methods include administering a therapeutically effective amount of an acoustic ECM hydrogel, thereby inhibiting the M1 macrophages in the subject. The subject can be any subject of interest, including human and veterinary subjects.

The disclosed acoustic ECM hydrogels increase hemostasis at a lesion in a subject. Thus, methods are also disclosed for accelerating clotting and/or decreasing bleeding time of a wound. In some embodiments, hemostasis is induced within about 10 to about 100 seconds after administering the acoustic ECM hydrogel to the subject, such as about 10, 20, 30, 40, 50, 60, 70, 80, 90 or 100 seconds.

In some embodiments, a therapeutically effective amount of an acoustic ECM hydrogel can be locally administered to a site in a subject to induce hemostasis. The subject can have a wound. The wound can be an external wound, or in internal wound not viable from outside the patient. The disclosed acoustic ECM hydrogels are of use as a hemostatic agent at any type of wound. The method can include selecting any one of the subjects of interest, such as those with any wound.

As shown in FIG. 10, an acoustic ECM hydrogel decreases clotting time. Clotting can be measured by any method known to those of skill in the art. In the Lee and White test tube method, venous blood is placed in three test tubes, kept at 37° C. in a water bath. The clotting time is determined by tilting the first and then the second test tube at one minute intervals and recording the time at which a firm clot has formed in each of them in turn, and then detecting the coagulation of the blood in the third tube to give the coagulation time. In the capillary tube method, a glass capillary is filled with blood from a finger puncture. Short pieces of the capillary are broken off at regular intervals, until a blood clot appears between the broken parts of the capillary. Another method for determining the appearance of the clot is the thromboelastogram method. In this method a fork, moved in the blood or plasma sample is used to sense the viscosity, which increases at the time of coagulation. A further method for recording the occurrence of clotting is by monitoring the translucency of a blood plasma sample after it has been isolated from the blood. With the appearance of the clot the sample becomes opaque.

In some embodiments, methods are disclosed for treating a subject with inflammation or a wound. The method includes locally applying a therapeutically effective amount of an acoustic ECM hydrogel to the inflammation or the wound. In some non-limiting examples, the subject has an inflammatory disorder, such as, but not limited to, ulcerative colitis or rheumatoid arthritis. The method can include applying the ECM hydrogel to a tissue surface. In other non-limiting examples, the subject is an organ transplant recipient, a subject with graft versus host disease, a subject with myocardial infarction, or a subject with a wound, such as, but not limited to, a subject with a surgical wound or a non-surgical traumatic wound. Thus, disclosed in a method for accelerating wound healing and/or increasing hemostasis in an individual in need thereof, comprising administering a therapeutically effective amount of a composition including the acoustic ECM hydrogel, as disclosed herein. The administration can be local, such as to the site of the wound or graft.

The hydrogels can be applied to any wound site to increase hemostasis and/or increase wound healing. The wound can be a wound in the skin, or a wound on any surface, including, but not limited to, the eye. Methods are also provided for wounds that result from ischemia and ischemic injury, such as chronic venous leg ulcers caused by an impairment of venous circulatory system return and/or insufficiency. Thus, the present methods can utilize topical dermal or ocular administration. Generally, in these applications, the composition is formulated for topical administration. The hydrogels can be applied to a tissue surface of any organ.

Topical compositions to heal wounds, such as dermal wounds, are disclosed herein. These wounds amenable to treatment may be of superficial nature or may be deep and involve damage of the dermis and the epidermis of skin. The wound can be a surgical wound. Thus, methods are provided to promote wound healing in a subject, and/or promote clotting (increase hemostasis) in the subject.

The acoustic hydrogel can be applied directly to the target location, for example in a topical preparation such as a sheet, plug, or as a part of a dressing or a bandage. Bandage and wound dressings may contain the acoustic ECM hydrogel. These may be prepared by applying the acoustic ECM hydrogel, in the gel or liquid phase, together with any other additives desired, to a bandage or wound dressing. These, sheets, plugs, bandages or dressings can be used to decrease clotting time and or to increase wound healing. The acoustic hydrogel can be administered by injection to the target location to promote wound healing, for example, as a solid in the gel phase, or the temperature can be raised above 37° C. prior to administration such that the hydrogel is administered in the liquid phase.

For use in wound treatment, and/or for increasing hemostasis, the acoustic ECM hydrogel will usually have a concentration in the range described above. The acoustic ECM hydrogel can be applied a single time. Alternatively, the acoustic ECM hydrogel can be applied to the affected area periodically, typically from about 1 to 10 times each day, such as, for example, over a period of from about 3 to 14 days, depending on the nature of the wound. In some cases, it may be desirable to apply the compositions indefinitely.

The acoustic ECM hydrogel affects hemostasis and the rate of wound healing. In some embodiments, the composition increases hemostasis and/or wound healing at least 20%, at least 30%, at least 40%, at least 50%, at least 60%, at least 70%, at least 80%, at least 90%, at least 95%, at least 100%, or at least 200%, as compared to a control, such as a standard value, the rate of wound healing or hemostasis achieved without treatment, or with treatment of an ECM hydrogel produced by enzymatic methods.

The acoustic ECM hydrogel can also be used in the treatment of a surgical wound and other intentional interventions where the compositions may be applied immediately after completion of the surgery. Methods are provided for stimulating healing of wounds, and increasing hemostasis at a wound site, including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, and burns resulting from heat exposure or chemicals.

The subject can be any mammalian subject of interest, including a human or a veterinary subject. The subject can be a child or an adult subject, such as a young, middle aged, or older adult subject. In humans, an adult subject is greater than 18 years of age, a young adult is about 18 to about 35 years of age, a middle aged adult is generally considered to be about 35 to about 55 years of age, and an elderly (or aged) human subject is more than about 55 years old, such as more than 60 years old, more than 65 years old, more than 70 years old, more than 75 years old or more than 80 years old.

The subject can heal wounds at a normal rate or can be healing impaired. A number of afflictions and conditions can result in healing impairment. These include diabetes (such as Type II diabetes mellitus), treatment with both steroids and other pharmacological agents, and ischemic blockage or injury (as in peripheral vascular disease or traumatic vascular occlusion). Conditions which induce abnormal wound healing, include, but are not limited to uremia, malnutrition, vitamin deficiencies, obesity, infection, immunosuppression and complications associated with systemic treatment with steroids, radiation therapy, and antineoplastic drugs and antimetabolites. Steroids which have been shown to impair wound healing include cortisone, hydrocortisone, dexamethasone, and methylprednisolone. Non-steroid compounds, such as octreotide acetate, have also been shown to impair wound healing (Waddell et al., Am. Surg. 63:446 449, 1997).

The subject can have a clotting disorder, or can be undergoing treatment with anticoagulants, such as, but not limited to warfarin or PLAAVIX®. The subject can have a Factor II, V, VII, X, or XII deficiency. The subject can have hemophilia A, hemophilia B, von Willebrand's disease, a deficiency or structural abnormalities in fibrinogen, or prothrombin. Thus, in some embodiments, these subjects are selected for treatment.

Methods are also provided herein to increase the adherence of skin grafts to a wound bed and to stimulate re-epithelialization from the wound bed. Types of grafts include, but are not limited to: autologous skin graft, artificial skin, allografts, autodermic graft, autoepidermic grafts, avascular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. The methods include administering to the subject with the graft a therapeutically effective amount of the compositions disclosed herein, thereby increasing the adherence and acceptance of the graft and controlling or eliminating bacterial growth. In some embodiments, cells or a tissue treated with the composition are transplanted into a subject. In one specific, non-limiting example, the composition is administered to a graft, such as a skin graft, prior to transplantation.

Methods are also provided to treat blisters and burns due to abrasion or chemical injury. These methods include the treatment of the skin or internal organs. These methods include treatment of ovary injury, for example, due to treatment with chemotherapeutics or treatment with cyclophosphamide; radiation- or chemotherapy-induced cystitis; or high-dose chemotherapy-induced intestinal injury. The methods include administering to the subject a therapeutically effective amount of a composition as disclosed herein to promote healing of the blisters or burns and to reduce or eliminate bacterial growth.

Methods are provided for promoting the healing of anastomotic and other wounds caused by surgical procedures in individuals. These methods include administration of an effective amount of the compositions disclosed herein, after, and/or during anastomotic or other surgery. Anastomosis is the connecting of two tubular structures, for example, when a mid-section of intestine is removed and the remaining portions are linked together to reconstitute the intestinal tract. Unlike cutaneous healing, the healing process of anastomotic wounds is generally obscured from view. Further, wound healing, at least in the gastrointestinal tract, occurs rapidly in the absence of complications; however, complications often require correction by additional surgery (Thornton and Barbul, Surg. Clin. North Am. 77:549 573 (1997)). The method can include selecting a subject in need of anastomotic wound healing. The subject can be a subject with impaired wound healing due to one of the conditions above, or can be a subject that has normal wound healing, such as a subject that does not have any of the conditions listed above.

The disclosed acoustic ECM hydrogels are in a solid phase at room temperature, and transition toward a liquid phase at about 37° C. Thus, in some embodiments, following application to the subject, the acoustic ECM hydrogel will transition from the solid phase to the liquid phase over time as the hydrogel warms from body heat. In some embodiments, the method can include washing the wound, to remove the acoustic ECM hydrogel, which can be rinsed away in the liquid phase.

In some embodiments, the acoustic ECM hydrogels are subject to sterilization. Sterilization is important to ensure acoustic ECM hydrogels of the invention are sufficiently removed of contamination from pathogens and suitable for medical use, such as implantation into a human or animal body. Methods such as gamma irradiation, ethylene oxide, supercritical $CO_2$, hydrogen peroxide gas plasma, or ozone may be suitable for sterilization of acoustic ECM hydrogels of the invention, although other methods of sterilization known in the art may also be suitable. As shown herein, gamma sterilization is an acceptable method of sterilization as acoustic ECM hydrogels of the invention maintain their stiffness when gamma sterilized. In one embodiment, an acoustic ECM hydrogel is subject to gamma sterilization before the ECM solution forms a gel, e.g., the ECM in liquid can be sterilized prior to sonication, or after sonication before forming a gel. In another embodiment, an acoustic ECM hydrogel is subject to gamma sterilization after the gel is formed. In some embodiments, the acoustic ECM hydrogel remains in gel form, or can form a gel, following sterilization by gamma irradiation.

In contrast, for enzymatically produced hydrogels, gamma irradiation destabilizes the composition. Thus, a gel is not formed, or is destabilized, following gamma irradiation.

Acoustic ECM Hydrogels as a Submucosal Cushion

Endoscopy is a procedure that allows examination of the interior of a hollow organ or cavity of the body by means of an instrument called an endoscope, without employing invasive surgery. Endoscopy can be used for surgical procedures such as cauterization of a bleeding vessel, removing polyps, adenomas and small tumors, performing biopsies or removing a foreign object. Endoscopic procedures can be performed in the gastrointestinal tract, the respiratory tract, the ear, the urinary tract, the female reproductive system and, through small incisions, in normally closed body cavities such as the abdominal or pelvic cavity (laparoscopy), the interior of a joint (arthroscopy) and organs of the chest (thoracoscopy and mediastinoscopy). Endoscopy can be performed in the upper gastrointestinal tract or the lower gastrointestinal tract. The endoscope is an illuminated, usually fiber optic, flexible or rigid tubular instrument for visualizing the interior of a hollow organ or part (such as the bladder, esophagus, stomach or intestine) for diagnostic or therapeutic purposes, that typically has one or more working channels to enable passage of instruments (such as forceps, electrosurgical knife, endoscopic injection needles or scissors) or to facilitate the removal of bioptic samples. It includes a suitable lamp and imaging device at its distal portion, and it can be inserted through natural occurring openings of the body, such as the mouth, the anus, the ear, the nose or through small surgical incisions. Given the wide variety of body organs or cavities which can be examined by means of endoscopic procedures, several types of specialized endoscopes exist, such as, for example, laryngoscope, thoracoscope, angioscope, colonoscope, enteroscope, sigmoidoscope, rectoscope, proctoscope, anoscope, arthroscope, rhinoscope, laparoscope, hysteroscope, encephaloscope, nephroscope, esophagoscope, bronchoscope, gastroscope, amnioscope, cystoscope.

Endoscopic procedures are widely applied in the gastrointestinal tract, including the upper and the lower gastrointestinal tract. For example, endoscopic procedures can be used to examine the mucosa that covers the gastrointestinal cavities, and to detect small and large pathological lesions, such as inflammatory tissue, polyps, pseudo-polyps, serrated lesions, adenomas, ulcerations, dysplasias, pre-neoplastic and neoplastic formations, and tumors. Endoscopic procedures can be used for biopsies and removal of pathologic lesions (polyps, adenomas, dysplasias, pre-neoplastic and neoplastic formations, tumors). Surgical interventions include two types of endoscopic resection procedures commonly used in gastrointestinal endoscopy to remove pathological lesions: endoscopic mucosal resection (EMR) and endoscopic submucosal dissection (ESD). These two techniques allow for minimally invasive treatment of gastrointestinal polyps, adenomas, dysplasias, and early-stage cancers that involve a minimum risk of lymph-node metastasis.

Methods are disclosed herein for dissecting a mucosa and a submucosa from a muscularis propria from a region of an organ of a subject. The organ can be in the gastrointestinal tract, for example, the esophagus, the duodenum, stomach, small intestine, large intestine (colon) or rectum. The organ can be the bladder, organs of the oral-respiratory system (lungs, throat (pharynx), tongue, nasal passages, sinuses), the skin, or the uterus and vaginal tract. Examples of specific tissues are respiratory epithelium, nasal epithelium, dermal or epidermal tissue and uterine epithelium. One exemplary organ is the esophagus. Another exemplary organ is the colon. The methods are of use in any organ that has a mucosa and a submucosa, wherein a superficial lesion can be formed, such as a malignant or pre-malignant lesion.

These methods include injecting submucosally into the organ of the subject a pharmaceutical composition comprising an acoustic ECM hydrogel to form a cushion between the submucosa and the underlying muscularis propria at the region of the organ. In one embodiment, the organ is not the esophagus. In another embodiment, the organ is the esophagus. The method can be an endoscopic mucosal resection (EMR) or an endoscopic submucosal dissection (ESD).

EMR is an endoscopic technique developed for removal of sessile or flat neoplasms confined to the superficial layers (mucosa and submucosa) of the gastrointestinal (GI) tract. EMR is typically used for removal of lesions smaller than 2 cm or piecemeal removal of larger lesions. EMR also plays an important role in the assessment of resected specimens for accurate pathological staging. In contrast to polypectomy, EMR involves the lifting up of a lesion from the muscular layer by injecting a fluid agent, commonly normal saline (NS) solution, into the submucosal layer. EMR is also useful for obtaining specimens for accurate histopathological staging to determine the risk of lymph-node metastasis. EMR facilitates the complete removal of the affected mucosa by excising through the middle or deeper portion of the gut wall submucosa. Various EMR techniques have been described and four methods involving snare resection are commonly used: (1) the inject and cut method; (2) the inject, lift, and cut method; (3) cap-assisted EMR (EMRC); and (4) EMR with ligation (EMRL). In the inject and cut technique, the diseased mucosa is lifted up from the muscular layer by creating a submucosal fluid cushion, captured, strangulated using an electrosurgical snare, and then resected. However, injection into the thin submucosal layer is a delicate process, the injected solution tends to dissipate quickly, flat and depressed lesions are hard to capture with the snare compared with protruded lesions, and large or awkwardly located lesions can be difficult to remove (Uraoka et al., Drug Design, Development and Therapy 2008:2 131-138). Injection-assisted EMR is frequently used for large flat colon polyps.

Endoscopic submucosal dissection (ESD) was specifically developed for removing larger lesions. Lesions are dissected directly along the submucosal layer using an electrosurgical knife, resulting in an en-bloc resection of even large lesions. ESD has been predicted to replace conventional surgery in treating certain cancerous stages, but since it has a higher rate of perforation and bleeding complications than conventional EMR, a greater degree of endoscopic skill and experience is required than for EMR. ESD can use numerous electrosurgical knives, such as an insulation-tipped diathermic knife, a needle knife, a hook knife, a flex knife, a triangle tipped knife, a flush knife, splash needle, and a small-caliber tip transparent hood. These knives can be used with a high frequency electrosurgical current (HFEC) generator. ESD is characterized by three steps: (1) injecting a fluid to form a submucosal cushion to elevate the lesion from the muscle layer; (2) circumferential cutting of the surrounding mucosa of the lesion; and (3) dissection of the connective tissue of the submucosa beneath the lesion (see Kakushima et al., Wold J. Gstroenterol. 14(9): 2962-2967, 2008, incorporated herein by reference. Various submucosal injection solutions had previously been developed and shown to be satisfactory for use during EMR, but introduction of the lengthier ESD procedure required a longer-lasting solution to help identifying the cutting line during dissection of the submucosal layer (Uraoka et al., Drug Design, Development and Therapy 2008:2 131-138). The presently disclosed methods meet this need.

A submucosal injection is used in EMR, as injection of fluid into the submucosa cushions facilitates the isolation of the tissue to be removed just before capture of the target lesion, such as with a snare, thereby reducing thermal injury and the risk of perforation and hemorrhage while also facilitating resection. Submucosal injection plays an important role in the EMR procedure, as the solution must be retained in place for sufficient duration and needs to form a hemispheric shape to facilitate snaring. In addition, providing a sufficiently high submucosal elevation results in safe submucosal cutting during the ESD procedure (Uraoka et al., Drug Design, Development and Therapy 2008:2 131-138). Furthermore, as inflammation results from the procedure, any cushion retained at the procedure site should have anti-inflammatory properties. The acoustic ECM hydrogel will mitigate stricture and promote re-epithelialization. The presently disclosed methods also meet this need.

In some embodiments, the disclosed methods utilize an acoustic ECM hydrogel that has anti-inflammatory properties, and is inexpensive, non-toxic, easy to inject and provides a high, long-lasting submucosal cushion. The acoustic ECM hydrogel is administered in its gel state at the site of injection to form a cushion. The cushion can be dissected during the procedure so that some hydrogel remains on the underlying muscularis propria, thereby aiding healing. The disclosed acoustic ECM hydrogel facilitates closure of the wound created by removal of the resected mucosa/submucosa. In some embodiments, the procedure is an ESD. In other embodiments, the procedure is an EMR.

Normal saline solution (NS) and thinner solutions (e.g, ELEVIEW™, see U.S. Pat. No. 9,226,996, incorporated herein by reference) have been used as submucosal cushions for endoscopic resection, but the inherent characteristics of these solutions make it difficult to produce the proper submucosal fluid cushion, maintain the desired height, and retain the cushion at the desired location, because of the rapid dispersion of the solution. Furthermore, in ESD, once the mucosa/submucosa are removed, these agents will not be retained on the underlying muscularis propria. Furthermore, these agents to not aid the healing process, such as by reducing inflammation. The use of an acoustic ECM hydrogel meets these needs.

The acoustic ECM hydrogel disclosed herein can be used as in any ESD or ESR. As disclosed in U.S. Pat. No. 9,364,580, incorporated herein by reference, endoscopic injection needles are devices which can be long (up to about 230) cm and which include a relatively long catheter within which an inner injection tube having a distal injection needle is slideably disposed. A proximal actuating handle is coupled to the catheter and the injection tube for moving one relative to the other when necessary. Fluid access to the injection tube is typically provided via a leer connector on the handle. Endoscopic injection needle devices are typically delivered to the injection site through the working channel of the endoscope. In order to protect the lumen of the endoscope working channel from damage, the handle of the infusion needle device is manipulated to withdraw the distal injection needle into the lumen of the catheter before inserting the device into the endoscope. This prevents exposure of the sharp point of the injection needle as the device is moved through the lumen of the endoscope. When the distal end of the endoscopic injection needle device is located at the injection site, its handle is again manipulated to move the injection needle distally out of the lumen of the catheter. When advanced to the most distal position, the exposed portion of the injection needle is approximately 4-6 mm in length.

After the injection site has been pierced, the acoustic ECM hydrogel, usually contained in a 5 ml to 10 ml syringe provided with a luer-lock fitting connected to the handle of the injection needle, can be delivered through the injection tube and the needle into the injection site, such as between the submucosa and the underlying muscularis propria.

The injection needle and other accessories commonly used during endoscopic procedures, such as snares for polypectomy, clipping devices, biopsy forceps and similar, are passed through one or more specific channels of the endoscope, usually called working channels or operating channels. Depending upon the type of endoscope used in GI endoscopy (e.g. gastroscope, enteroscope, colonoscope, duodenoscope, sigmoidoscope and similar), the inner diameter of the working channels may vary considerably. However, the most common endoscopes used in GI endoscopy have working channels with inner diameter in the range from about 2 mm to about 5 mm. Generally, the manufacturers of endoscopic accessories produce accessories having outer diameters which allow them to fit all the working channels. In some embodiments, the endoscopic injection needles, the outer diameter of catheter ranges from 1.9 mm to 2.3 mm, such as about 1.9, 2.0, 2.1, 2.2 or 2.3 cm. Thus, considering that the inner injection tube is contained in the outer catheter, its internal diameter is usually 1 mm or less. The disclosed acoustic ECM hydrogel in gel or liquid form, can readily pass through these catheters.

The acoustic ECM hydrogel can be used in an endoscopic resection procedure by sucking a volume of the hydrogel from its primary container by means of a syringe, injecting a suitable volume of said hydrogel by means of an endoscopic injection needle inserted in the working channel of the endoscope immediately under the superficial mucosal layer, to depose the hydrogel into the submucosal layer that becomes a cushion when in place: the elevation of the mucosal surface allow the endoscopist to perform an easy resection of the mucosal lesion found during the execution of the endoscopic procedure even if the lesion is flat and thus not protruding into a lumen, such as an intestinal, esophageal, or gastric lumen. At body temperature, the acoustic ECM hydrogel is a viscous yet flowable gel transitioning to the liquid phase and can be easily injected under the superficial mucosal layer to form a cushion for this procedure. Because the gel-sol transition takes time, the cushion remains in place for a sufficient time for the resection to take place.

The presence of at least one dye into the cushion can aid an endoscopist to visualize the structures beneath the mucosa (e.g. the submucosal layer and the external muscular wall), thereby lowering the risk that the endoscopist, performing the resection procedure, may cause damages to said structures. The use of the dye can allow visualization of the cushion cavity and the mucosal basement. The removal of the lesion from the mucosal surface generates a mucosal wound. The persistence of the cushion generated by the injected volume of the pharmaceutical composition allows the endoscopic resection procedure to be performed without the need to re-inject. The acoustic ECM hydrogel is injected submucosally into a region of interest in the organ of the subject, such as at the region of a lesion or tumor, to form a cushion between the submucosa and the underlying muscularis propria at the region of the organ. The cushion can be dissected, such that a portion of the acoustic ECM hydrogel is maintained on the underlying muscularis propria and aid in the healing process.

The disclosed methods are of use in the esophagus. In a non-limiting example, the method comprises a method of dissecting an esophageal carcinoma or adenocarcinoma from the esophagus. In another non-limiting example, the method comprises dissecting the mucosa and the submucosa from the esophagus of a subject who has Barrett's esophagus. In these embodiments, the acoustic ECM hydrogel can be a urinary bladder, a small intestinal submucosal (SIS), an esophageal, a trachea, a liver or a dermal acoustic ECM hydrogel.

The disclosed methods are also of use in other organs. The organ can be any organ of interest, such as an organ of the gastrointestinal tract. The organ may be in the upper gastrointestinal tract such as the pharynx, tongue or mouth. The organ may be the bladder, vaginal tract, or uterus. In some embodiments, the organ is the colon, duodenum, stomach, cecum, colon, sigmoid colon, rectum, small intestine or large intestine. In one non-limiting example, the organ is the stomach, the small intestine or the large intestine, and the method comprises a method of dissecting a carcinoma or adenocarcinoma from the stomach. In a further non-limiting example, the organ is the colon, and wherein the method comprises dissecting a polyp or a carcinoma from the colon. In these embodiments, the acoustic ECM hydrogel can be a urinary bladder, a small intestinal submucosal, an esophageal, a trachea, a liver or a dermal acoustic ECM hydrogel.

An acoustic ECM hydrogel, as disclosed herein, is maintained at a temperature at or below which it gels for application as a submucosal cushion.

The acoustic ECM hydrogel can be maintained, for example, at about 4° C. or at about room temperature prior to administration. In one embodiment, the acoustic ECM hydrogel can be administered at a temperature, for example, from 4° C. to below 37° C., or from 4° C. to 25° C. In one embodiment, the acoustic ECM hydrogel is administered at a temperature below 37° C. An effective amount of the acoustic ECM hydrogel as a gel is then utilized. The acoustic ECM hydrogel remains as a gel in the tissue of the subject, which is at a temperature of approximately 37° C. In one embodiment, the gel to sol transition of the acoustic ECM hydrogel is at about 37° C., such that the hydrogel can be used as a submucosal cushion because it is sufficiently viscous at body temperature.

In some embodiments, the ECM concentration is in the hydrogel is 25 mg/ml to about 200 mg/ml, such about ECM hydrogel is 25 mg/ml to about 100 mg/ml. In other embodiments, the ECM concentration is the hydrogel is about 50 to about 150 mg/ml, such as about 75 to about 125 mg/ml, such as about 75, 80, 85, 90, 95, 100, 105, 110, 115, 120 or 125 mg/ml. In a specific non-limiting example, the ECM concentration in the hydrogel is about 100 mg/ml.

The acoustic ECM hydrogel can be provided in a lyophilized form at either room temperature, a cold temperature (for example about 4° C.) or frozen (for example, at about −20° C.), and reconstituted just prior to administration to the anatomic region of interest in the subject.

The disclosed methods are of use in any subject, including human and veterinary subjects. The subject can be any age. The subject can be an adult or a juvenile. In one embodiment, a composition including an acoustic ECM hydrogel is injected in a target tissue in an organ to form a cushion which is then optionally subjected to an endoscopic surgical procedure, such as a resection procedure. The ECM can be from the same species as the subject being treated, or can be from a different species. In some embodiments, the subject is human, and the acoustic ECM hydrogel is derived from human or porcine ECM. In other embodiments, the ECM hydrogel is derived from a non-human primates, dog, cat, horse, or cow. The acoustic ECM can also be from a commercial source. The acoustic ECM hydrogel can, in some embodiments, be derived from any mammalian tissue, such as but not limited to porcine or human tissue, and be, in some non-limiting examples, urinary bladder, small intestine, or the esophagus. Any of the acoustic ECM hydrogels disclosed above, derived from any source tissue, can be used as a submucosal cushion, and/or in any of the disclosed methods. The acoustic ECM hydrogel can be an esophageal acoustic ECM hydrogel or a urinary bladder acoustic ECM hydrogel.

The disclosed methods are invasive, as they require an injection that dissects a mucosa and a submucosa from a muscularis propria from a region of an organ of an intestinal tract of a subject. In some embodiments, the acoustic ECM hydrogel is not applied to a surface of an organ, such as an organ of the gastrointestinal tract, such as the esophagus. The disclosed methods can be used in the esophagus, but can also be used in other tissues.

Any of the methods disclosed herein can include injecting submucosally into the organ of the subject a pharmaceutical composition including an acoustic ECM hydrogel to form a cushion between the submucosa and the underlying muscularis propria at the region of the organ. Suitable acoustic ECM hydrogels are disclosed above. The acoustic ECM hydrogel gels and dissects the mucosa and the submucosa from the underlying muscularis propria and inhibits inflammation in the region of the organ in the subject. The acoustic ECM hydrogel as a gel can be administered endoscopically or via a catheter. In some embodiments, the organ is the esophagus, colon, stomach, cecum, colon, sigmoid colon, rectum, small intestine or large intestine. The acoustic ECM hydrogel, as a gel or sol, also can be administered endoscopically or via a catheter. In further embodiments, the acoustic ECM hydrogel can be a urinary bladder, a small intestinal submucosal, an esophageal, a trachea, a liver or a dermal acoustic ECM hydrogel. In some embodiments, ECM can be from a human tissue. In other embodiments, ECM can be from porcine tissue.

In some embodiments, the resection procedure is an endoscopic mucosal resection or an esophageal endoscopic submucosal dissection, and the method comprises a method of dissecting an esophageal carcinoma or adenocarcinoma from the esophagus. In more embodiments, the method includes dissecting the mucosa and the submucosa from the esophagus of a patient who has dysplasia. In more embodiments, the method includes dissecting the mucosa and the submucosa from the esophagus of a subject who has Barrett's esophagus.

In some embodiments, the resection procedure is an endoscopic mucosal resection or an endoscopic submucosal dissection. In further embodiments, the organ is the stomach, small intestine or large intestine, and the method comprises a method of dissecting a polyp, a carcinoma or an adenocarcinoma from the colon. In more embodiments, the method includes dissecting the mucosa and the submucosa from an organ of a patient who has dysplasia. In specific non-limiting examples, the method comprises dissecting a polyp or a carcinoma from the colon.

The methods can also include performing an endoscopic resection procedure on the cushion. In some embodiments, the methods include dividing the cushion such that hydrogel is retained on the underlying muscularis propria of the esophagus and the mucosa and the submucosa are removed from the region of the esophagus. In some non-limiting examples, the portion of the hydrogel cushion that is retained on the underlying muscularis propria downregulates pro-inflammatory macrophage activation in the esophagus.

The disclosure is illustrated by the following non-limiting Examples.

EXAMPLES

Currently, methods for producing hydrogels from ECM involve digestion of the ECM material with an acid protease in an acidic solution (Feyetes, Biomaterials 29(11) (2008) 1630-7; Voytik-Harbin, Tissue Engineering 4(2) (1998) 157-174), the use of α-amylase digestion to produce ECM foams (Kommuller et al., JoVE (Journal of Visualized Experiments) (122) (2017) e55436); or the use of chaotropic extraction buffers and lengthy dialysis procedures (Uriel, Tissue Eng Part C Methods 15(3) (2009) 309-21; Uriel, Biomaterials 29(27) (2008) 3712-9). ECM hydrogels made according to such methods are inevitably subjected to protein degradation and denaturation which may attenuate the bioactivity of the full complement of ECM molecules and tissue specific ECM components. Moreover, enzyme-based methods for producing ECM hydrogels require lengthy incubation times ranging from 24-72 hours to achieve adequate solubilization of ECM components, and require the addition of an exogenous enzyme for digestion (Saldin et al., Acta Biomater 49 (2017) 1-15; Spang et al., Acta biomaterialia 68 (2018) 1-14). ECM hydrogels prepared using enzymatic digestion are also hampered by limited concentration-dependent rheological properties (Saldin et al., supra, 2017). To realize the full clinical potential of ECM hydrogels, a fundamentally different approach was developed whereby an ECM hydrogel can be rapidly formed without the use of acidic or alkaline solutions, protease digestion, or chemical extraction and dialysis.

Disclosed are methods for producing acoustic ECM hydrogels using ultrasonic cavitation, and the characterization of the viscoelastic properties, cytocompatibility and bioactivity of these acoustic ECM hydrogels. In some embodiments, using comminuted ECM as a starting material, the method involves resuspension of ECM in a neutral buffered saline solution followed by solubilization using a 20 kHz ultrasonic frequency. Rapid gelation of the ECM solution can be induced by decreasing the temperature of the ECM solution to temperatures below 25° C. Gelation time and ECM gel properties can be easily tuned by adjusting ECM concentration, and sonication amplitude and time. Once polymerized, the ECM gels are stable at temperatures ranging from 4° C. to 37° C. Moreover, ECM hydrogels prepared using this method are biocompatible and capable of promoting an M2-like, pro-remodeling macrophage phenotype that is conducive to downstream constructive tissue remodeling (Hussey et al., Nature Reviews Materials, 3:159-173 (2018)). These methods offer advantages for large-scale manufacturing of acoustic ECM hydrogels over traditional enzymatic methods, which produce hydrogels with different properties. Acoustic ECM hydrogels produced by the presently disclosed methods can be used in tissue engineering and regenerative medicine-based clinical applications.

Example 1

Materials and Methods

Preparation of Dermal ECM: Dermal ECM was prepared as previously described (Reing J E, et al. Biomaterials. 2010; 31(33):8626-33). Briefly, full-thickness skin was harvested from market-weight (~110 kg) pigs (Tissue Source Inc.), and the subcutaneous fat and epidermis were removed by mechanical delamination. This tissue was then treated with 0.25% trypsin (Thermo Fisher Scientific) for 6 hours, 70% ethanol for 10 hours, 3% $H_2O_2$ for 15 min, 1% Triton X-100 (Sigma-Aldrich) in 0.26% EDTA/0.69% tris for 6 hours with a solution change for an additional 16 hours, and 0.1% peracetic acid/4% ethanol (Rochester Midland) for 2 hours. Water washes were performed between each chemical change with alternating water and phosphate-buffered saline (PBS) washes following the final step. All chemical exposures were conducted under agitation on an orbital shaker at 300 rpm. Dermal ECM was then lyophilized and milled into particulate using a Wiley Mill with a #60 mesh screen.

Preparation of urinary bladder matrix (UBM): UBM was prepared as previously described (Mase V J, et al. Orthopedics. 2010; 33(7):511). Porcine urinary bladders from market-weight animals were acquired from Tissue Source, LLC. Briefly, the tunica serosa, tunica muscularis externa, tunica submucosa, and tunica muscularis mucosa were mechanically removed. The luminal urothelial cells of the tunica mucosa were dissociated from the basement membrane by washing with deionized water. The remaining tissue consisted of basement membrane and subjacent lamina propria of the tunica mucosa and was decellularized by agitation in 0.1% peracetic acid with 4% ethanol for 2 hours at 300 rpm. The tissue was then extensively rinsed with PBS and sterile water. The UBM was then lyophilized and milled into particulate using a Wiley Mill with a #60 mesh screen.

Preparation of small intestinal submucosa (SIS): SIS was prepared as previously described (Badylak S F, et al. J Surg Res. 1989; 47(1):74-80). Briefly, jejunum was harvested from 6-month-old market-weight (~110 to ~120 kg) pigs and split longitudinally. The superficial layers of the tunica mucosa were mechanically removed. Likewise, the tunica serosa and tunica muscularis externa were mechanically removed, leaving the tunica submucosa and basilar portions of the tunica mucosa. Decellularization and disinfection of the tissue were completed by agitation in 0.1% peracetic acid with 4% ethanol for 2 hours at 300 rpm. The tissue was then extensively rinsed with PBS and sterile water. The SIS was then lyophilized and milled into particulate using a Wiley Mill with a #60 mesh screen.

Preparation of Esophageal ECM: Esophageal ECM was prepared as previously described (Keane T J, et al. Tissue Eng Part A. 2015; 21(17-18):2293-300). Briefly, esophageal ECM (eECM) was prepared by mechanically separating the mucosa and submucosa from the muscularis externa and subjecting the mucosal layers to 1% trypsin/0.05% EDTA (Invitrogen, Carlsbad, CA) for 1 h at 37° C. on a rocker plate, deionized water for 15 min, 1 M sucrose (Fisher Scientific, Pittsburgh, PA) for 30 min, deionized water for 30 min, 3.0% Triton X-100 (Sigma-Aldrich, St. Louis, MO) for 48 h, deionized water for 15 min, phosphate-buffered saline (PBS; Fisher Scientific) for 15 min, 10% deoxycholate (Sigma-Aldrich) for 4 h, deionized water for 30 min, 0.1% peracetic acid (Rochester Midland Corp., Rochester, NY) in 4.0% ethanol for 4 h, 100 U/mL DNAse (Invitrogen) for 2 h on a rocker plate, followed by 15-min washes with PBS, deionized water, PBS, and deionized water. All washes were agitated at 300 rpm on a shaker plate. Esophageal ECM was then lyophilized and milled into particulate using a Wiley Mill with a #60 mesh screen.

Sonication of ECM: 100 mg of ECM powder was resuspended in phosphate buffered saline (PBS) in a 15 mL conical tube and sonicated with a FISHERBRAND™ Model 120 Sonic Dismembrator equipped with a ⅛" probe. The ECM concentration was varied from 20-200 mg (w/v). The resuspended ECM was sonicated for a cyclic pulse of 30 s on and 45 s off at the 100% amplitude setting. The cycle was repeated six times to generate a soluble ECM solution. This cyclic pulse setting ensured that the gel solution maintained a temperature ranging from 34-40° C.

Gelation of sonicated ECM solutions: ECM solutions were poured into 3D molds and the temperature lowered to 25 C or below to induce gelation. ECM gels were stored at 4 C or freeze dried to generate a lyophilized ECM construct that maintained its 3D geometry. Alternatively, ECM solutions were spread evenly over a Teflon sheet and incubated at 4° C. to induce gelation. The ECM gels were then incubated at room temperature for 24 hrs to evaporate water resulting in an ultrathin ECM sheet.

Preparation of an ECM putty: ECM powder was resuspended in 25 mg/ml (w/v) PBS and sonicated as described above. At concentrations ≤25 mg/ml, and temperatures between 4-30 C, the solubilized ECM forms into a putty.

ECM hydrogel rheology: All rheological data was collected using a rheometer (AR2000, TA instruments, New Castle, DE) fitted with 40 mm parallel plate geometry, as previously described (Medberry C J, et al. Biomaterials.

2013; 34(4):1033-40) and analyzed using the American Society for Testing and Materials (ASTM) standard F2900-11 (Guide for characterization of hydrogels used in regenerative medicine). Temperature was controlled within 0.1° C. using a Peltier plate. At room temperature (25° C.) or 4° C., the gel precursor was loaded onto the parallel plate rheometer. Sample evaporation was minimized using mineral oil to seal the edges of the sample-plate interface.

Scanning electron microscopy: Scanning electron micrographs were taken to examine the surface topology of the ECM hydrogel. Samples were fixed in cold 2.5% (v/v) glutaraldehyde (Electron Microscopy Sciences, Hatfield, PA) in PBS for at least 24 hr, followed by three washes in PBS. Fixed samples were then dehydrated using a graded series of alcohol (30, 50, 70, 90, 100%) for 15 min each, followed by 15 min in hexamethylenediamine (Fisher) and subsequent air-drying. The dried samples were sputter coated with a 3.5 nm layer of gold/palladium alloy using a Sputter Coater 108 Auto (Cressington Scientific Instruments, Watford, UK) and imaged with a JEOL JSM6330f scanning electron microscope (JEOL, Peabody, MA) at 100× and 500× magnifications.

Cytocompatibility assay: 3T3 fibroblasts were seeded on 96-well plates coated with ECM hydrogels prepared from UBM, SIS or dermis. Uncoated wells were used as a control. The cells were cultured in Dulbecco's modified minimal essential medium that was supplied with 10% fetal bovine serum, and 1% penicillin-streptomycin. Twenty-four hours after seeding cells, the VYBRANT® MTT Cell Proliferation Assay Kit (Thermo Fisher) used to the viability of cells according to the manufacturer's protocol. Absorbance of the converted dye was measured at a wavelength of 540 nm.

Hemostasis assay. The Lee White clotting assay was used. Fresh whole blood is collected into a test tube and the tube tilted repeatedly until clotting is observed.

Liver Laceration model: Sprague-Dawley Rats, age 6-8 weeks, were anesthetized with Isoflurane (1-3%). Animals were maintained at a surgical plane of anesthesia with 1.5-2.5% isoflurane in oxygen and positioned in ventral recumbency. Using sterilized instruments, a small incision was created and an underlying 2 cm midline laparotomy performed to expose the liver. An incision, 2 mm deep and 5 mm in length, was made on the ventral surface of the liver by placing a #11 scalpel blade in a Kelly clamp so that 2 mm of the blade was exposed. The wound was allowed to bleed for 3 seconds and then wiped clean with sterile gauze. Test articles were then placed on the defect site, and clotting times were recorded.

Macrophage activation: Murine, bone marrow was harvested from 6- to 8-week-old B6 mice. Harvested cells from the bone marrow were washed and plated at 2×106 cells/mL and were allowed to differentiate into macrophages for 7 days in the presence of macrophage colony-stimulating factor (MCSF) with complete medium changes every 48 h. Macrophages were then activated for 24 h with one of the following: 1) 20 ng/mL Interferon-γ (IFNγ) and 100 ng/mL lipopolysaccharide (LPS) (Affymetrix eBioscience, Santa Clara, CA; Sigma Aldrich) to promote an MIFNγ+LPS phenotype (M1-like); 2) 20 ng/mL interleukin (IL)-4 (Invitrogen) to promote an MIL-4 phenotype (M2-like); or 3) 2 mg/ml UBM acoustic gel. After the incubation period at 37° C., cells were washed with sterile PBS and cells fixed with 2% paraformaldehyde (PFA) for immunolabeling. To prevent nonspecific binding, the cells were incubated in a blocking solution composed of PBS, 0.1% Triton-X, 0.1% Tween-20, 4% goat serum, and 2% bovine serum albumin for 1 h at room temperature. The blocking buffer was then removed and cells were incubated in primary antibodies. The cells were incubated at 4° C. for 16 h, the primary antibody was removed, and the cells washed with PBS. A solution of fluorophore-conjugated secondary antibody was added to the wells for 1 h at room temperature. The antibody was then removed, the cells washed with PBS, and the nuclei were counterstained using DAPI. Cytokine-activated macrophages were used to establish standardized exposure times (positive control), which were held constant throughout groups thereafter.

Example 2

Results

Figure 4A:
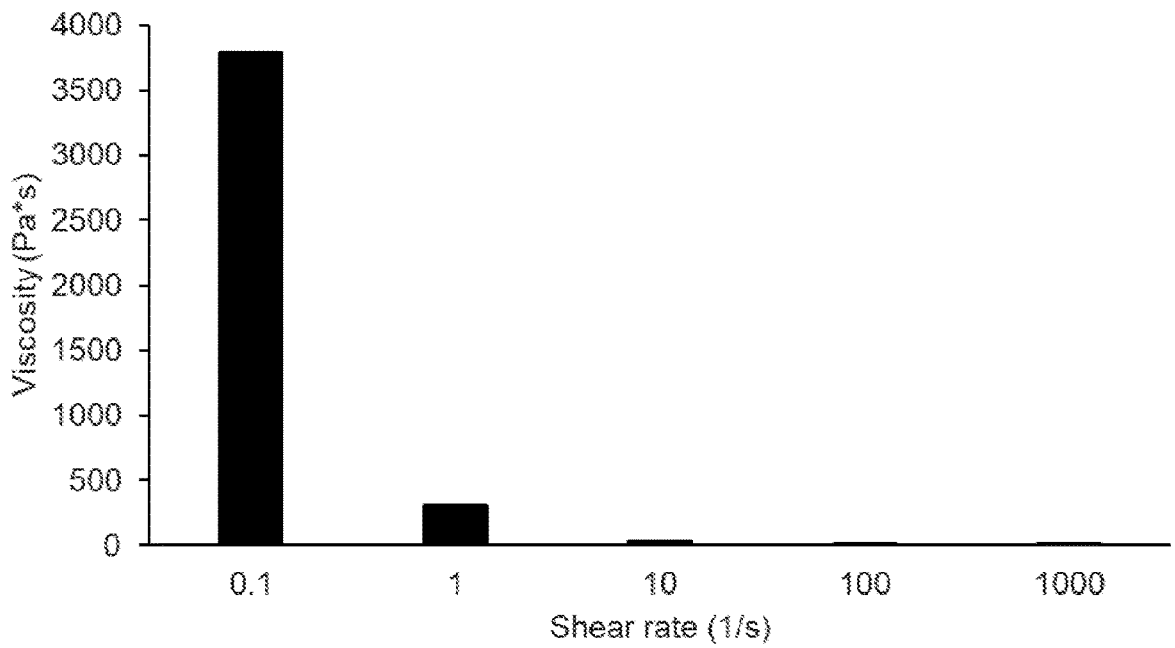
FIGS. 4A-4B: Flow sweep. A steady state flow sweep test was performed on the acoustic ECM gel at (A) 25° C., (B) 4 to 37° C. and 37 to 4° C. A constant stress is applied to the gel and the resulting deformation is measured. The data shows that the viscosity of the gel decreases with more stress, an implication of a shear thinning material.
Figure 4B:
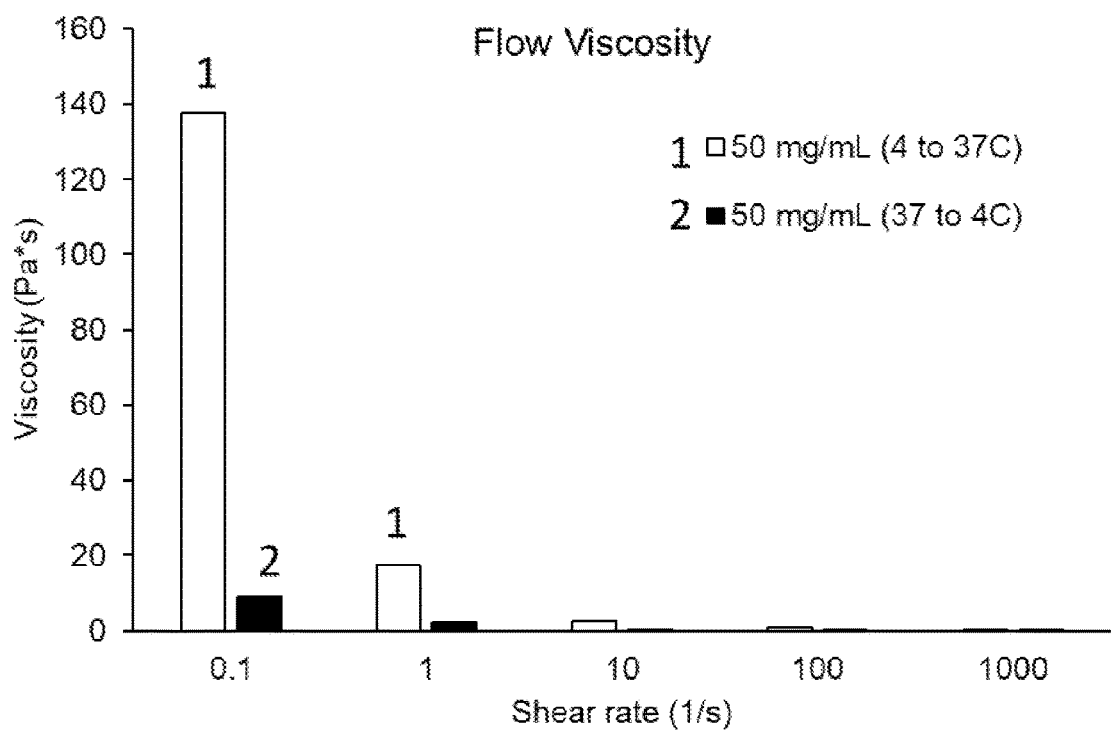
Figure 5A:
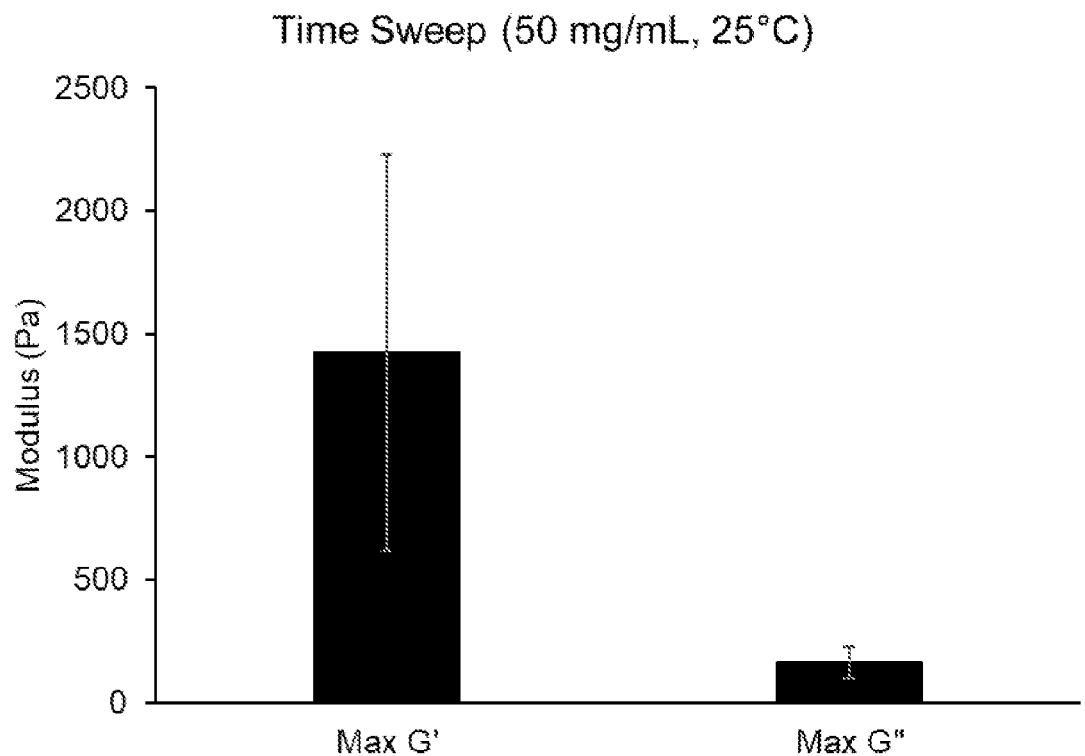
FIGS. 5A-5B: Time sweep test. A time sweep test was performed on a 50 mg/ml acoustic ECM gel at (A) 25° C., (B) 4 to 37° C., and 37 to 4° C., to determine the maximum G' (storage modulus) and G" (loss modulus) values. The data show that the storage>loss modulus at all temperatures; that is, it maintains the qualities of a hydrogel.
Figure 5B:
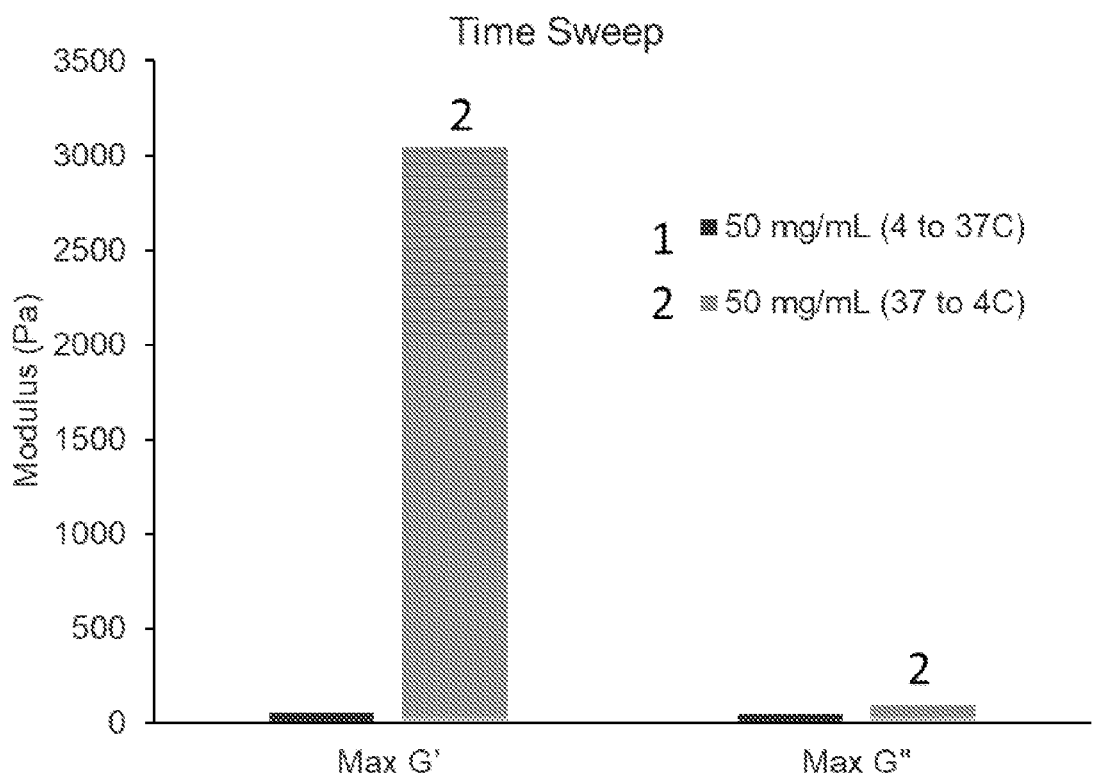
Figure 6A:
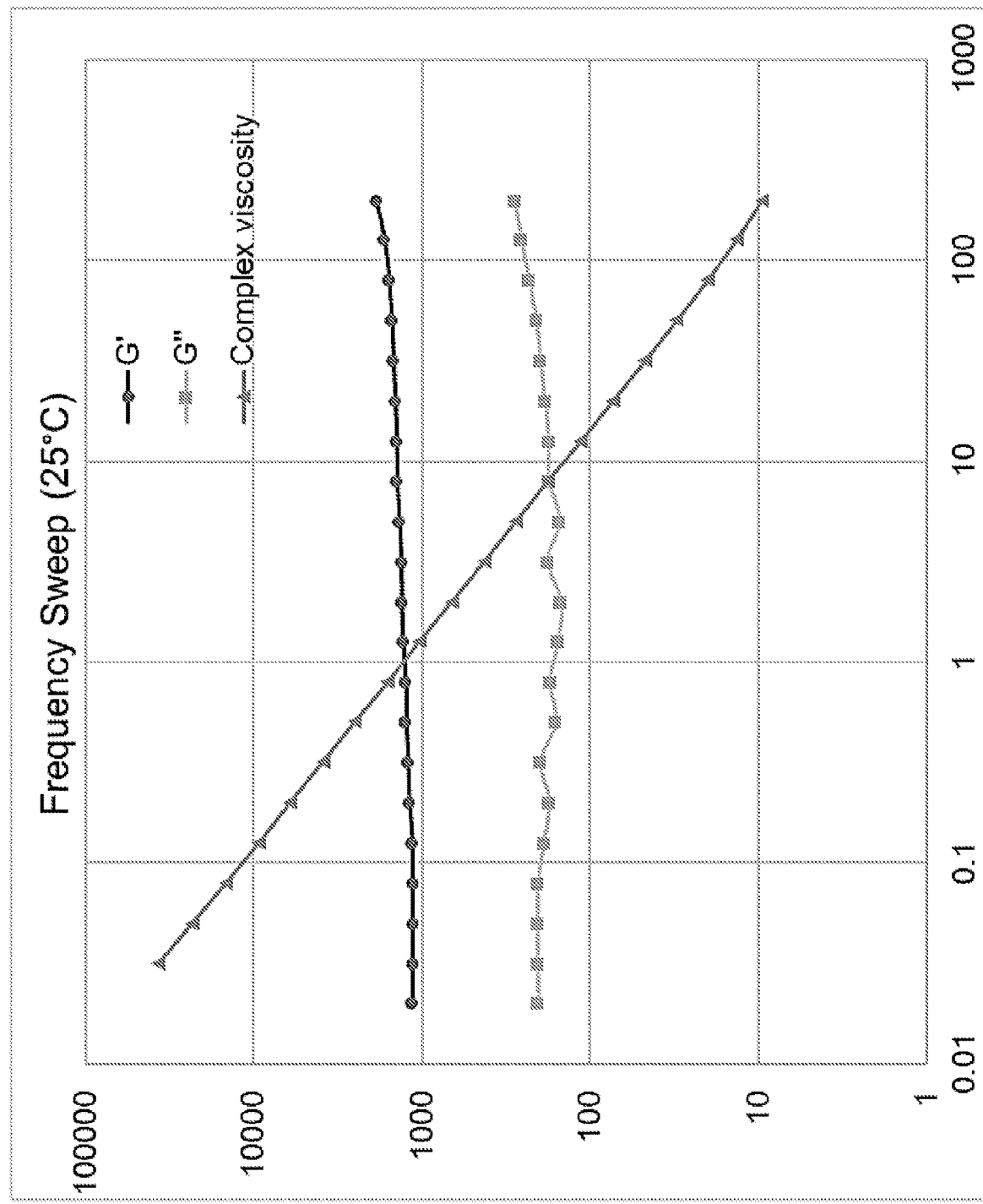
FIGS. 6A-6C: Representative graphs of the storage modulus, loss modulus, and complex viscosity of the 50 mg/ml acoustic ECM hydrogels. Data was plotted over angular frequencies on a log-log scale, measured at 25° C. (A), 4° C. (B), or temperature rapidly lowered from 37° C. to 4° C. (C) by applying a small 0.5% oscillatory strain. The data show that G'>G" by about an order of magnitude; which indicates that the material meets the criteria of a hydrogel.
Figure 6B:
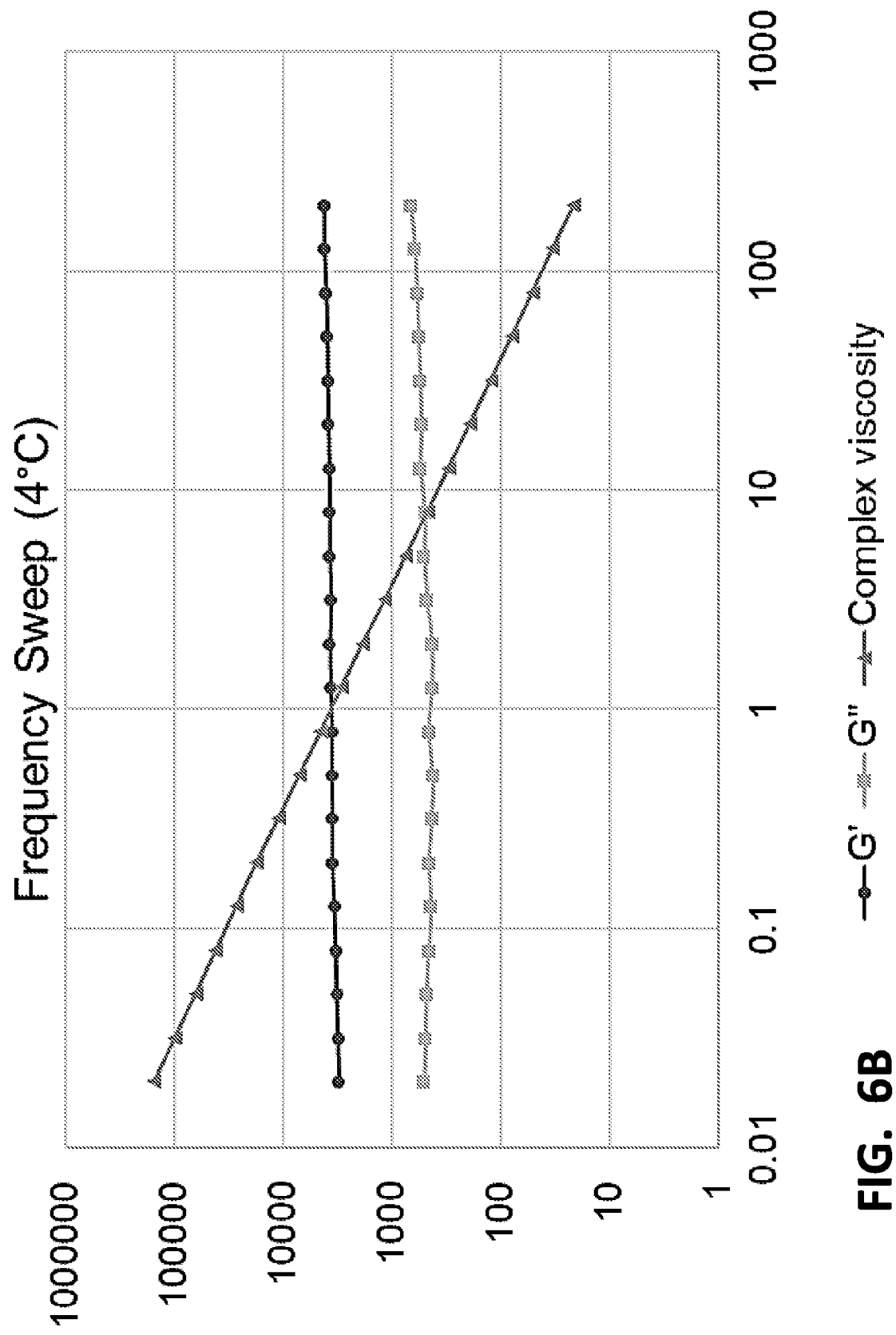
Figure 6C:
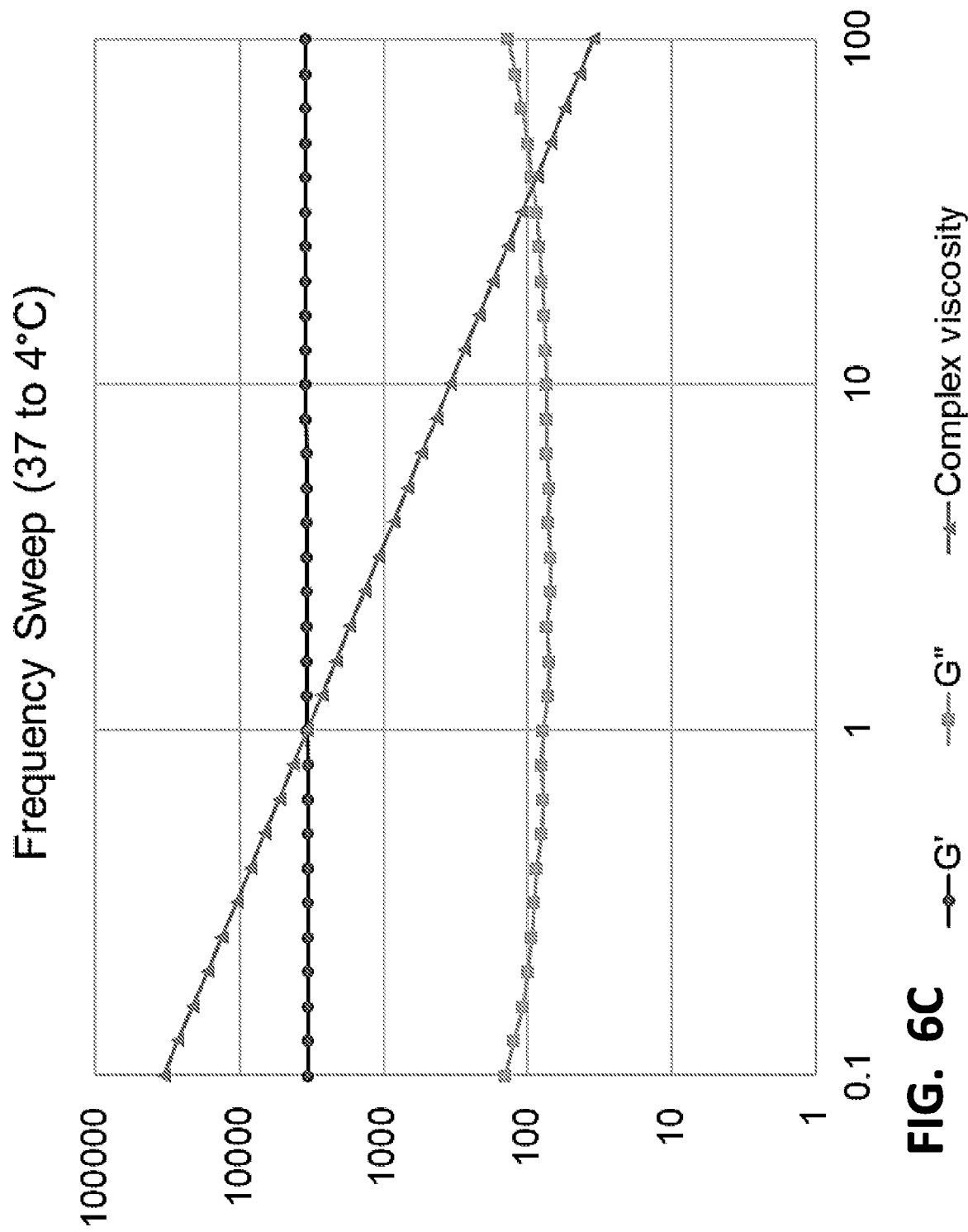
Figure 7:
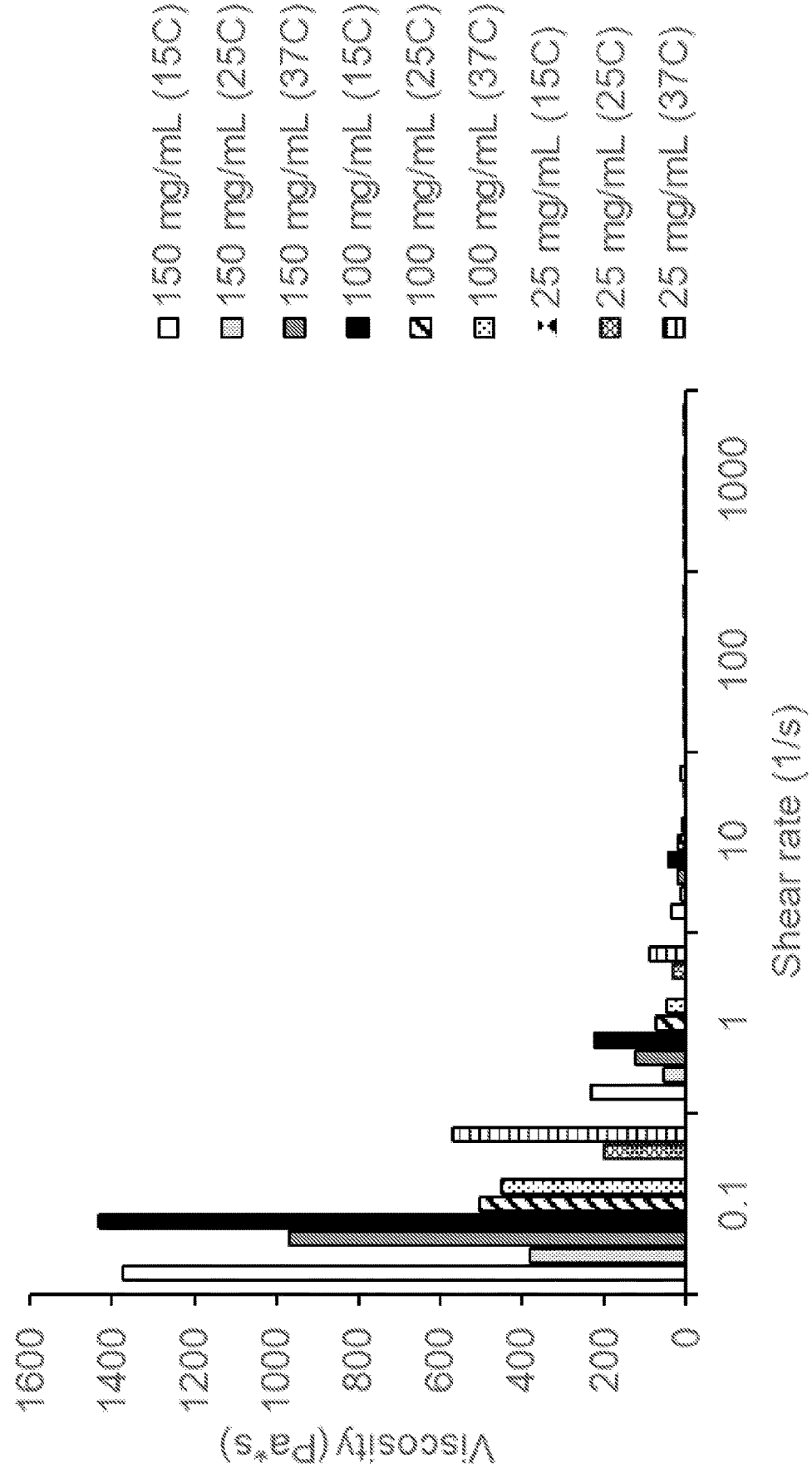
FIG. 7: Flow sweep. A steady state flow sweep test was performed on the acoustic ECM gel at 15° C., 25° C., or 37° C. for three different concentration: 25, 100, and 150 mg/ml. The data shows that at concentration ranges between 25 and 150 mg/ml and temperature ranges between 15-37° C. the viscosity of the gel decreases with more stress at 1, an implication of a shear thinning material. Shear thinning means that the viscosity decreases as the flow increases (e.g., the faster one "pushes" the material through an opening like the end of a needle or syringe, the "easier" it is to force the material through the opening which is advantageous for clinical applications)
Figure 8:
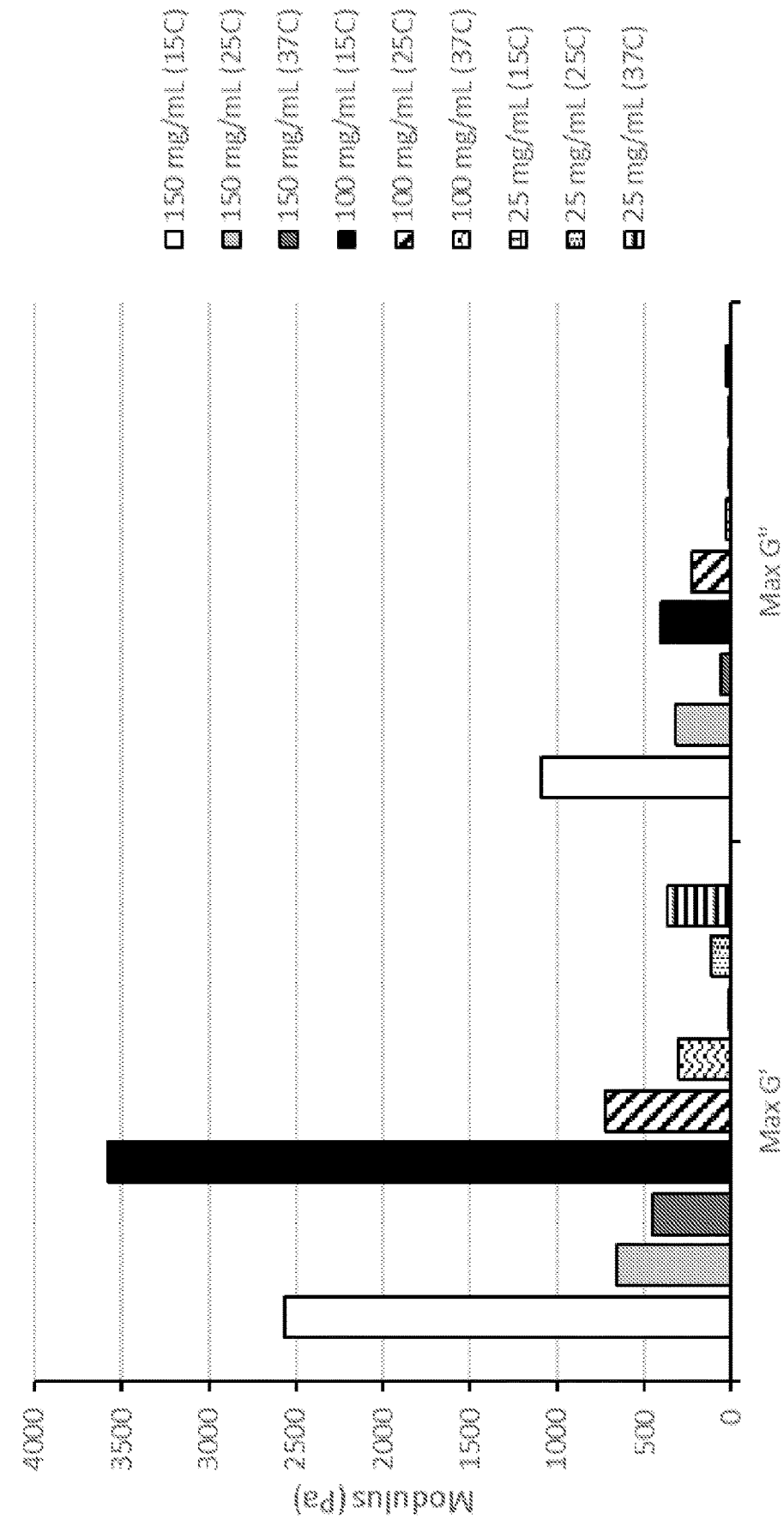
FIG. 8: Time sweep test. A time sweep test was performed to determine the maximum G' (storage modulus) and G" (loss modulus) values of acoustic hydrogels at 15° C., 25° C., or 37° C. and at three different concentration: 25, 100, and 150 mg/ml. The data show that the storage>loss modulus for all concentrations at all temperatures; that is, it maintains the qualities of a hydrogel.
Figure 9A:
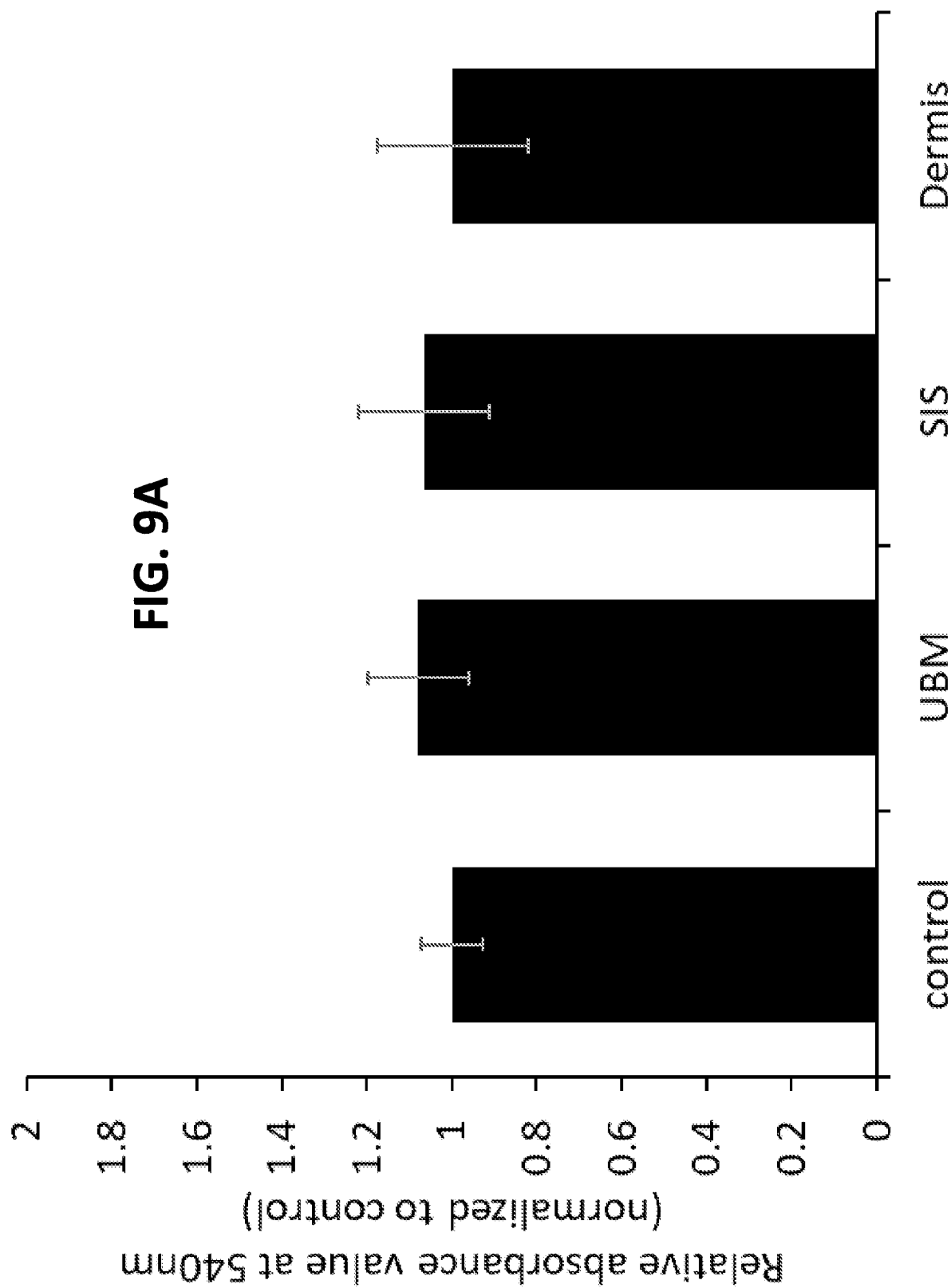
Figure 12A:
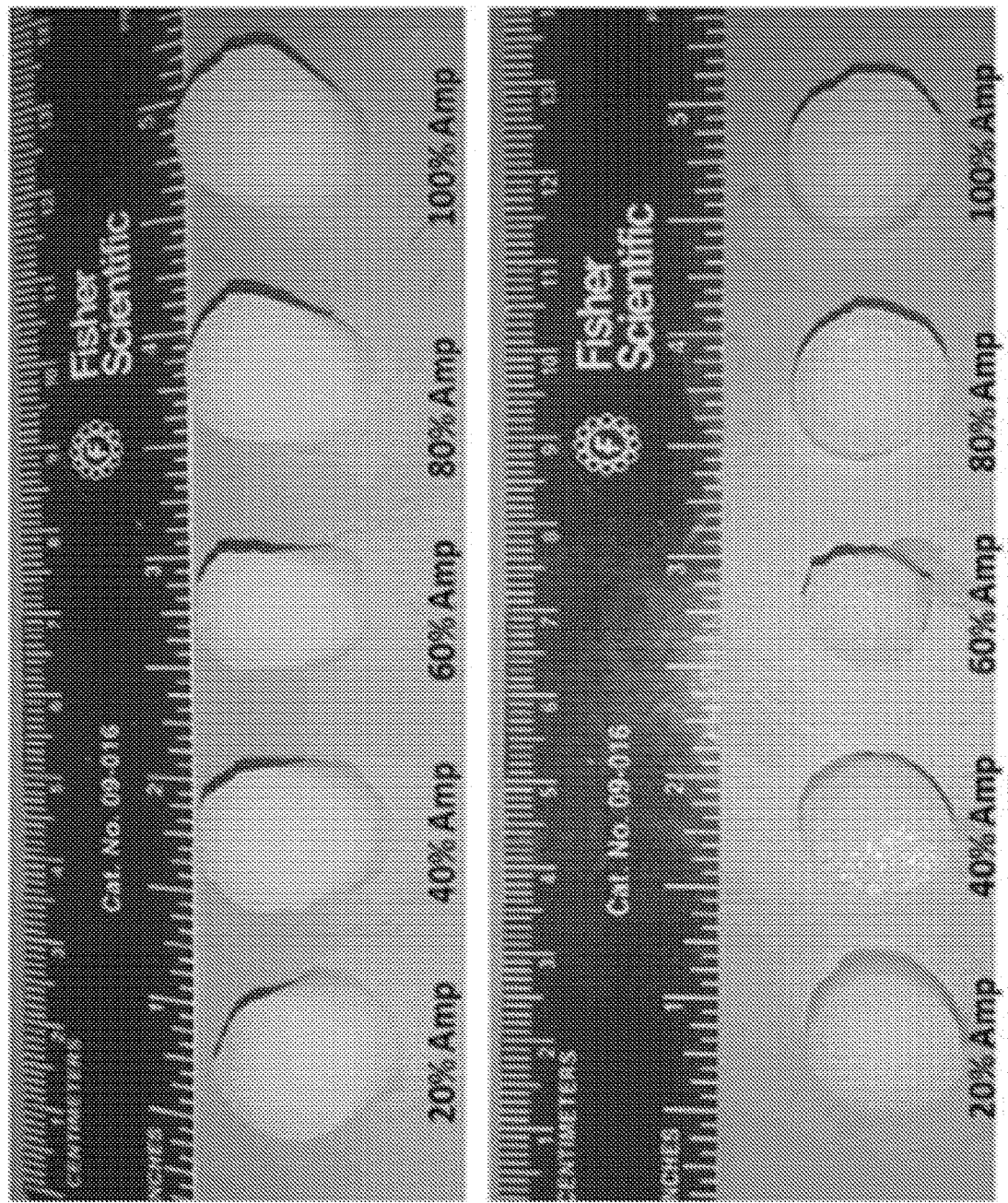
FIGS. 12A-12C: Acoustic hydrogels can be prepared by sonicating ECM at 20 kHz frequency using amplitudes ranging from 20-100%. Samples were all 50 mg/mL and sonicated for 10 minutes before running the experiment at 15° C. (A) Images of the hydrogels formed at the indicated amplitudes. (B) Flow Viscosity. Rheological data shows that at all amplitudes tested, the viscosity of the gel decreases with more stress, an implication of a shear thinning material. (C) Time Sweep. The rheological data shows that the storage>loss modulus for all concentrations at all amplitudes; that is, it maintains the qualities of a hydrogel.
Figure 12B:
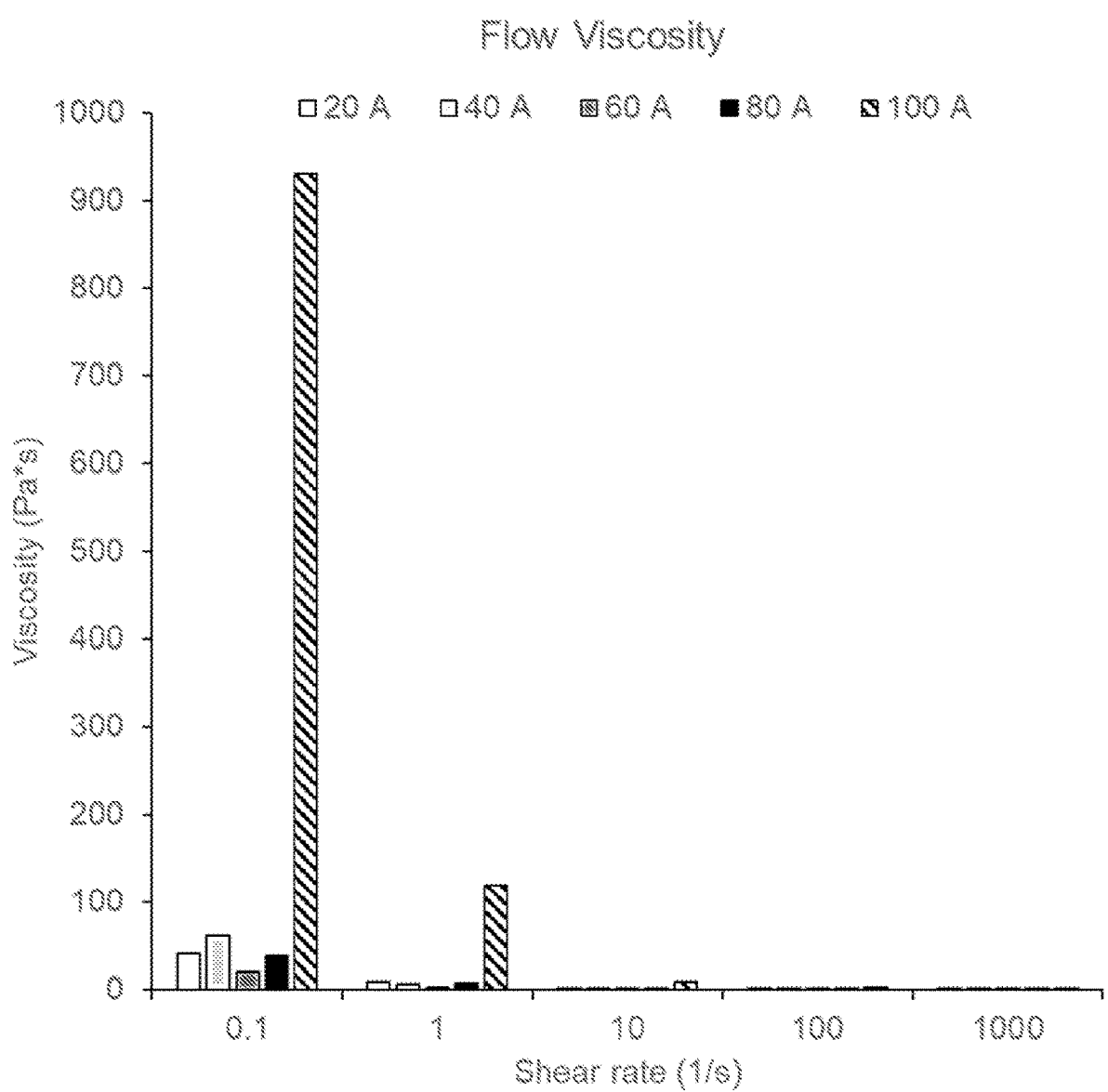
Figure 12C:
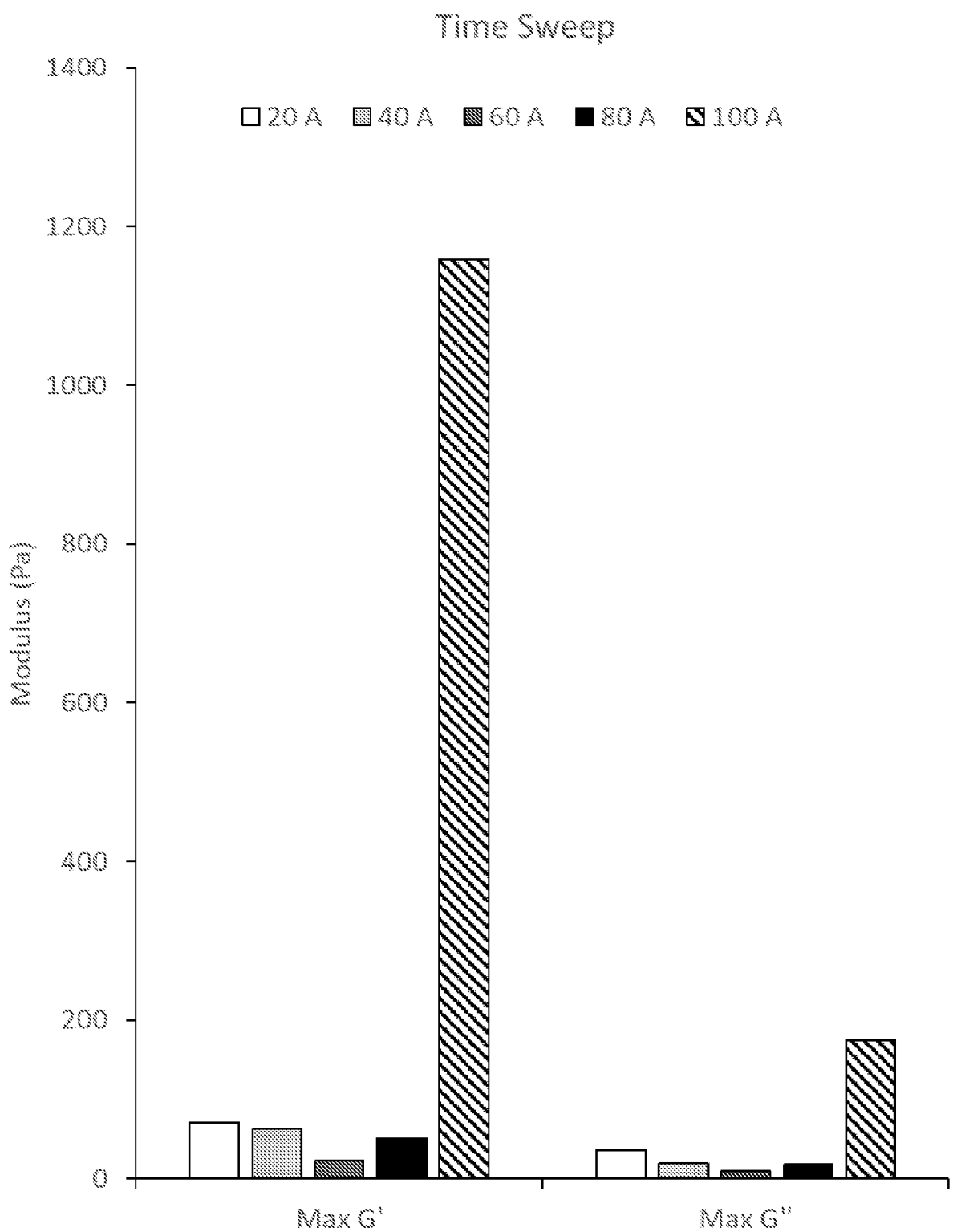
Figure 13:
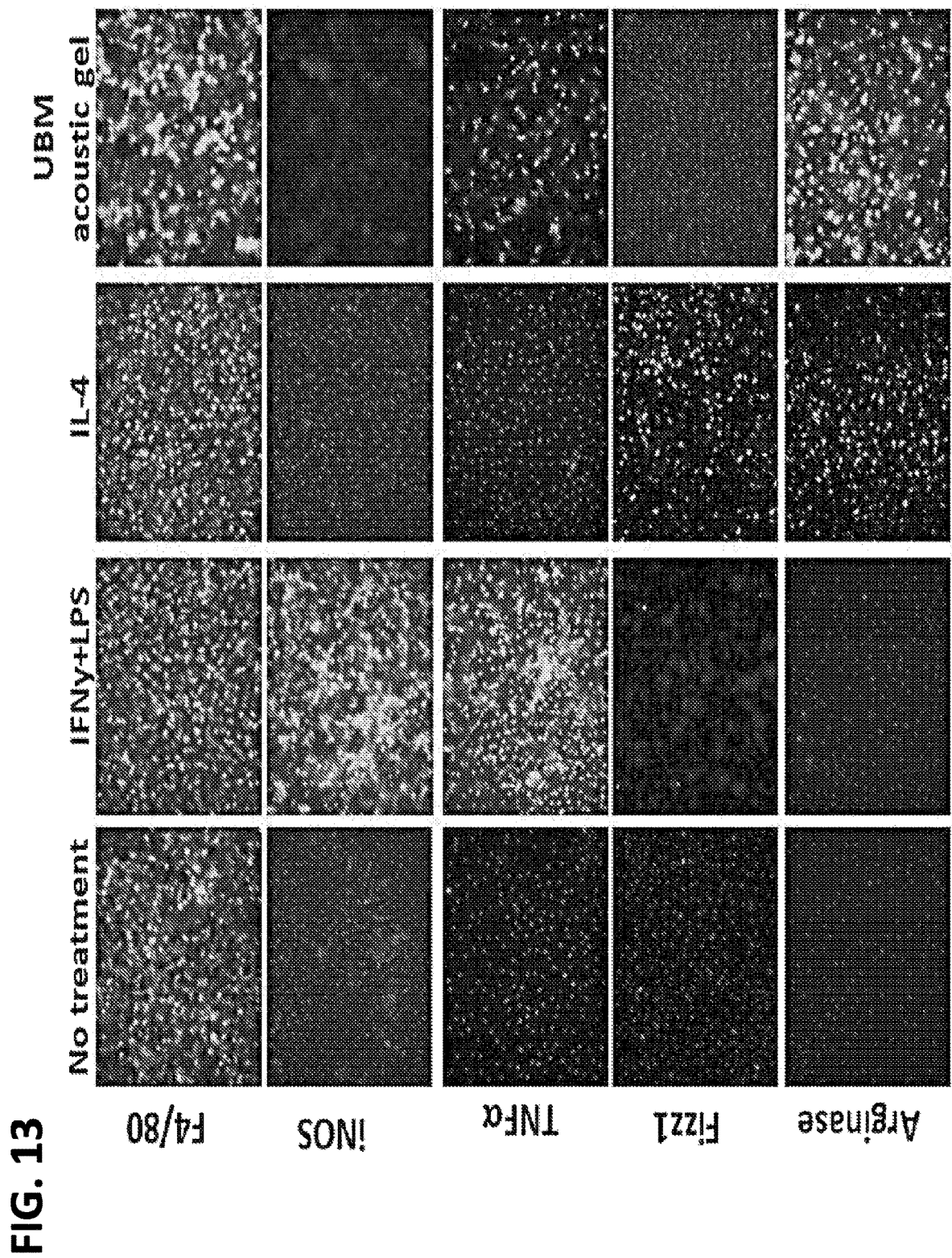
FIG. 13. UBM acoustic hydrogel promotes an M2-like macrophage phenotype. Mouse bone marrow derived macrophages were treated with 2 mg/ml UBM acoustic hydrogel for 24 hrs, fixed, and immunolabeled for strong indicators of the pro-inflammatory M1-like markers (iNos, TNFa) or pro-remodeling M2-like markers (izzi, Arginase), and counterstained with DAPI. Treatment of cells with IFNg and lipopolysaccharide (LPS) was used as a positive control for the M1-like phenotype, and IL-4 was used as a positive control for the M2-like phenotype. F4/80 staining was used as a positive control for macrophages. Cells were imaged at 200×. The data show that compared to controls, UBM acoustic hydrogel promoted a M2-like macrophage phenotype.

A method was developed for preparing a hydrogel from extracellular matrix (ECM). Using decellularized tissues as a starting material, the sonication technique can be applied to a broad array of tissue specific ECM including dermis, urinary bladder matrix (UBM), and small intestinal submucosa (SIS). The approach involves resuspension of comminuted ECM in a neutral buffered saline solution followed by ECM solubilization using, for example, a 20 kHz ultrasonic frequency using amplitudes ranging from 20-100% (FIG. 1). After 60 seconds of sonication, rapid gelation of the ECM solution is induced by decreasing the temperature of the ECM solution below 37° C. (FIG. 4, FIG. 5, FIG. 6). Results from the rheological evaluation show that using this method an ECM hydrogel can be prepared using ECM concentrations ranging from 25 mg/ml to 150 mg/ml (FIG. 7, FIG. 8). Once polymerized, the ECM gels are stable at room temperature and can conform to customizable 3D geometries (FIG. 2). ECM hydrogels prepared by sonication were shown to be cytocompatible when used as a substrate for culture cells in-vitro (FIG. 9, FIG. 13). Scanning electron micrographs of the gels show a dense fibrillary network (FIG. 3). In addition, the ECM hydrogel can be used as a hemostatic agent that may be applied to an anatomic site in patients to assist in hemostasis (FIG. 10, FIG. 11). Results are provided in the accompanying figures.

Example 3

Materials and Methods for Examples 4-7

Preparation of ECM bioscaffolds: Porcine dermal ECM (dECM) was prepared as previously described (Reing et al., Biomaterials 31(33) (2010) 8626-33). Briefly, full-thickness skin was harvested from market-weight (~110 kg) pigs, and the subcutaneous fat and epidermis were removed by mechanical delamination. This tissue was then treated with 0.25% trypsin (Thermo Fisher Scientific) for 6 hours, 70% ethanol for 10 hours, 3% $H_2O_2$ for 15 min, 1% Triton X-100 (Sigma-Aldrich) in 0.26% EDTA/0.69% tris for 6 hours with a solution change for an additional 16 hours, and 0.1% peracetic acid/4% ethanol (Rochester Midland) for 2 hours. Water washes were performed between each chemical change with alternating water and phosphate-buffered saline (PBS) washes following the final step. All chemical exposures were conducted under agitation on an orbital shaker at 300 rpm. Dermal ECM was then lyophilized and milled into particulate using a Wiley Mill with a #40 mesh screen.

Porcine urinary bladder matrix (UBM) was prepared as previously described (Mase et al., Orthopedics 33(7):511 (2010)). Briefly, the tunica serosa, tunica muscularis externa, tunica submucosa, and tunica muscularis mucosa were mechanically removed. The luminal urothelial cells of the tunica mucosa were dissociated from the basement membrane by washing with deionized water. The remaining tissue consisted of basement membrane and subjacent lamina propria of the tunica mucosa and was decellularized by agitation in 0.1% peracetic acid with 4% ethanol for 2 hours at 300 rpm. The tissue was then extensively rinsed with PBS and sterile water. The UBM was then lyophilized and milled into particulate using a Wiley Mill with a #40 mesh screen.

Porcine small intestinal submucosa (SIS) was prepared as previously described (Badylak et al., J Surg Res 47(1) (1989) 74-80). Briefly, jejunum was harvested from 6-month-old market-weight (~110 to ~120 kg) pigs and split longitudinally. The superficial layers of the tunica mucosa were mechanically removed. Likewise, the tunica serosa and tunica muscularis externa were mechanically removed, leaving the tunica submucosa and basilar portions of the tunica mucosa. Decellularization and disinfection of the tissue were completed by agitation in 0.1% peracetic acid with 4% ethanol for 2 hours at 300 rpm. The tissue was then extensively rinsed with PBS and sterile water. The SIS was then lyophilized and milled into particulate using a Wiley Mill with a #40 mesh screen.

Porcine esophageal ECM was prepared as previously described (Keane et al., Tissue Eng Part A 21(17-18) (2015) 2293-300). Briefly, esophageal ECM (eECM) was prepared by mechanically separating the mucosa and submucosa from the muscularis externa and subjecting the mucosal layers to 1% trypsin/0.05% EDTA (Invitrogen, Carlsbad, CA) for 1 h at 37° C. on a rocker plate, deionized water for 15 min, 1 M sucrose (Fisher Scientific, Pittsburgh, PA) for 30 min, deionized water for 30 min, 3.0% Triton X-100 (Sigma-Aldrich, St. Louis, MO) for 48 h, deionized water for 15 min, phosphate-buffered saline (PBS; Fisher Scientific) for 15 min, 10% deoxycholate (Sigma-Aldrich) for 4 h, deionized water for 30 min, 0.1% peracetic acid (Rochester Midland Corp., Rochester, NY) in 4.0% ethanol for 4 h, 100 U/mL DNAse (Invitrogen) for 2 h on a rocker plate, followed by 15-min washes with PBS, deionized water, PBS, and deionized water. All washes were agitated at 300 rpm on a shaker plate. eECM was then lyophilized and milled into particulate using a Wiley Mill with a #40 mesh screen.

Porcine tracheal ECM (tECM) was prepared as previously described (Lange et al., Journal of tissue engineering and regenerative medicine 11(3) (2017) 800-811) with minor modifications. Briefly, tracheas were incubated in a detergent solution containing 0.25% Triton X-100+0.25% sodium deoxycholate for 30 min of negative pressure vacuum cycling (15 cycles, −0.95 kPa max vacuum) then soaked overnight in fresh detergent solution. This process was repeated daily, replacing the detergent solution with sterile DI water on days two and three, a solution of 2000 KU/ml DNase in water on day four, and sterile DI water on day five. This cycle was repeated once for a total of 10 days of vacuum cycling, followed by overnight sterilization in 15% peracetic acid +4% ethanol, and washes and storage in sterile PBS. Trachea ECM was then lyophilized and milled into particulate using a Wiley Mill with a #40 mesh screen.

Porcine liver ECM (LECM) was prepared as previously described (Loneker et al., Journal of Biomedical Materials Research Part A 104(4) (2016) 957-965). Livers were harvested from market weight pigs (110-130 kg). The tissue was cut into 0.5 cm$^3$ pieces with a scalpel and subjected to three 15-minute washes in deionized water with mechanical agitation on an orbital shaker. The sections were then gently massaged to aid in cell lysis and soaked in 0.02% trypsin/ 0.05% EGTA at 37° C. for 2 h. The tissue was rinsed in type 1 water, and the massaging was repeated followed by mechanical agitation of the liver sections in 3% Triton X-100 for 18-24 hr. The rinsing was repeated until all visible remnants of cellular material were removed. After processing, the liver ECM was immersed in a solution of 0.1% peracetic acid followed by repeated rinses in type 1 water or PBS at pH 7.4. Liver ECM was then lyophilized and milled into particulate using a Wiley Mill with a #40 mesh screen.

Solubilization of ECM by ultrasonic cavitation: Comminuted ECM was resuspended in 10 ml of 1× phosphate buffered saline (PBS) in a 50 mL conical tube and sonicated with a FISHERBRAND™ Model 120 Sonic Dismembrator equipped with a ⅛" probe. The ECM concentration was varied from 25 to 100 mg/ml (w/v) and sonication time was varied from 30-500 seconds at amplitudes ranging from 20%-100%. An illustration of the experimental setup is shown in FIG. 14.

Collagen and sGAG quantification: Comminuted dECM (100 mg/ml) was sonicated, and the samples were centrifuged at 10,000×g for 30 minutes to compress the insoluble ECM components. The clear supernatant containing the solubilized ECM components was transferred to a new tube. Collagen concentration of the supernatant solution was determined with the Sircol Assay Kit (Biocolor Ltd., UK) following the manufacturer's recommended protocol. Sulfated glycosaminoglycan (sGAG) concentrations were determined using the Blyscan Sulfated Glycosaminoglycan Assay Kit (Biocolor Ltd., UK) following the manufacturer's recommended protocol.

Gelation assay: The test tube inversion method (Quin et al., Frontiers in chemistry 6 (2018); El-Fiqi et al., Acta biomaterialia 9(12) (2013) 9508-9521) was used to measure the gelation time. Immediately after sonication of the sample material (25, 50, or 100 mg/ml), 0.5 ml of sample was transferred to test tubes and incubated at constant temperatures of 4° C. or 25° C. The fluidity of the samples was observed every minute by inverting the tube. The time at which the sample stopped flowing was taken as the gelation time and the values were recorded.

Scanning electron microscopy: Scanning electron micrographs were taken to examine the surface topology of dECM hydrogels at 50 and 100 mg/ml. Samples were fixed in cold 2.5% (v/v) glutaraldehyde (Electron Microscopy Sciences, Hatfield, PA) in PBS for at least 24 hr, followed by three washes in PBS. Fixed samples were then dehydrated using a graded series of alcohol (30, 50, 70, 90, 100%) for 15 min each, followed by 15 min in hexamethylenediamine and subsequent air-drying. The dried samples were sputter coated with a 3.5 nm layer of gold/palladium alloy using a Sputter Coater 108 Auto (Cressington Scientific Instruments, Watford, UK) and imaged with a JEOL JSM6330f scanning electron microscope (JEOL, Peabody, MA).

Viscoelastic measurements: All rheological data was collected using a rheometer (AR2000ex, TA instruments, New Castle, DE) fitted with 40 mm parallel plate geometry, as previously described (Medberry et al., Biomaterials 34(4) (2013) 1033-40) and analyzed using the American Society for Testing and Materials (ASTM) standard F2900-11 (Guide for characterization of hydrogels used in regenerative medicine). Samples of each tissue type (dECM and eECM, 100 mg/ml) were brought to starting temperature (4, 25, or 37° C.), respective of the temperature profile being tested, for 1 hr before testing. Samples were loaded onto the AR-2000ex rheometer fitted with a 40 mm parallel plate geometry set to the starting temperature. Mineral oil was used to seal the edges of the sample-plate interface to minimize evaporation during the test. An oscillatory time sweep was performed for 1 hr to measure the sonicated hydrogel gelation kinetics by applying a small, 0.5% oscillatory strain at a frequency of 1 rad/s and rapidly changing the temperature (37 or 4° C.) depending upon the temperature profile tested. Data was exported using the Trios software (TA Instruments) and analyzed using Prism v8 software (GraphPad, San Diego, CA). "Average storage modulus" was the storage modulus G' averaged over the final 10 minutes of the 60 min test, representing the G' plateau. The time to 50% gelation was determined as the time to 50% of the average storage modulus.

In vitro metabolic assay: 3T3 fibroblasts were seeded on 96-well plates coated with 100 mg/ml ECM hydrogels prepared from UBM, SIS or dECM. Uncoated wells were used as a control. The cells were cultured in Dulbecco's modified minimal essential medium that was supplied with 10% fetal bovine serum, and 1% penicillin-streptomycin. Twenty-four hours after seeding cells, the Vybrant® MTT Cell Proliferation Assay Kit (Thermo Fisher) was used to evaluate the viability of cells according to the manufacturer's protocol. Absorbance of the converted dye was measured at a wavelength of 540 nm.

In vitro cytocompatibility: Primary equine mesenchymal stem cells were isolated as previously described (Adams et al., Equine veterinary journal 45(3) (2013) 372-375). Cells were seeded on 6-well plates coated with 100 mg/ml ECM hydrogels prepared from UBM or dECM. Uncoated wells were used as a control. Twenty-four hours after seeding, in-vitro cytocompatibility was determined using a LIVE/DEAD Viability/Cytotoxicity Kit (Invitrogen) following the manufacturer's directions. Images were taken of five 200× fields across 3 technical replicates. Percent live and dead cells were quantified using CellProfiler. Images were taken with a Zeiss Axiovert microscope capturing five random fields at 200× magnification. Quantification of percentage of live and dead cells was completed using a custom CellProfiler pipeline.

In vitro macrophage response: Murine bone marrow cells were harvested from 6- to 8-week-old B6 mice. Harvested cells from the bone marrow were washed and plated at $2 \times 10^6$ cells/mL and were allowed to differentiate into macrophages for 7 days in the presence of macrophage colony-stimulating factor (MCSF) with complete medium changes every 48 h. Macrophages were then activated for 24 h with one of the following: 1) 20 ng/mL Interferon-γ (IFNγ) and 100 ng/mL lipopolysaccharide (LPS) (Affymetrix eBioscience, Santa Clara, CA; Sigma Aldrich) to promote an $M_{IFN\gamma+LPS}$ phenotype (M1-like); 2) 20 ng/mL interleukin (IL)-4 (Invitrogen) to promote an $M_{IL-4}$ phenotype (M2-like); 3) 2 mg/ml dECM hydrogel, or 4) 2 mg/ml eECM hydrogel. After a 24 h incubation period at 37° C., cells were washed with sterile PBS and cells fixed with 2% paraformaldehyde (PFA) for immunolabeling. To prevent nonspecific binding, the cells were incubated in a blocking solution composed of PBS, 0.1% Triton-X, 0.1% Tween-20, 4% goat serum, and 2% bovine serum albumin for 1 h at room temperature. The blocking buffer was then removed, and cells were incubated with primary antibodies. The cells were incubated at 4° C. for 16 h, the primary antibody was removed, and the cells washed with PBS. A solution of fluorophore-conjugated secondary antibody was added to the wells for 1 h at room temperature. The antibody was then removed, the cells washed with PBS, and the nuclei were counterstained using DAPI. Cytokine-activated macrophages (positive controls) were used to establish standardized exposure times (positive control) to image the remaining treatment groups.

Statistical Methods: All analyses were performed using Prism software (GraphPad Software Inc) with significance defined as p<0.05. Solubilized collagen and sGAG results were analyzed using ANOVA and pairwise comparisons with a post hoc Tukey's multiple comparisons test. Gelation time results were analyzed using ANOVA with a post hoc Tukey's multiple comparisons test. For single comparisons, a student's unpaired t-test was performed. Rheologic data was analyzed by a two-way ANOVA for the independent variables temperature and ECM type and the dependent variable storage modulus, with a post hoc Tukey's multiple comparisons test for the main effect of temperature. Student's unpaired t-test was performed to compare the gelation time of dECM and eECM.

Example 4

Solubilization of Collagen and sGAG

Figure 15A:
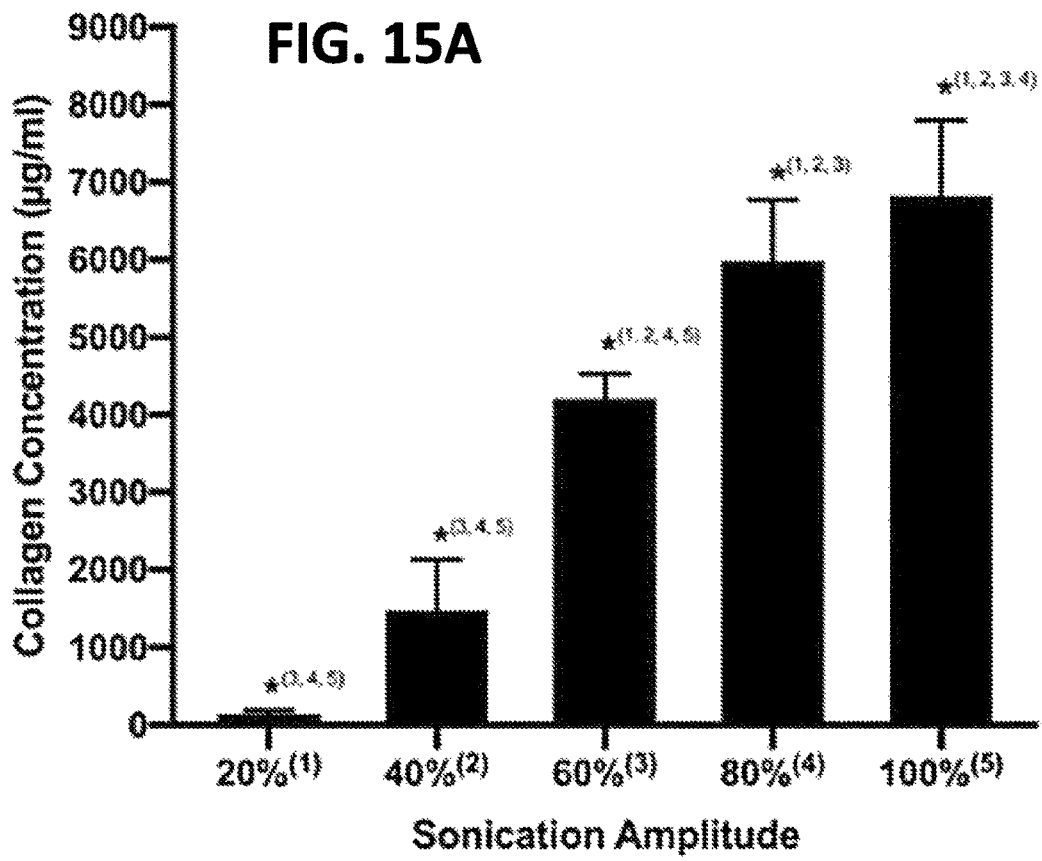
FIGS. 15A-15D. Solubilization of collagen and sulfated glycosaminogylcans (sGAG). (A) Concentration of solubilized collagen as a function of sonication amplitude. Comminuted dECM was sonicated for 300 seconds at the indicated amplitudes. The concentration of solubilized collagen measured using the SIRCOL™ assay. Data are presented as means±s.d. for n=3 samples per group. * represents p<0.05. Superscripts designate pairwise comparisons. (B) The concentration of sGAG as a function of sonication amplitude. Comminuted dECM was sonicated for 300 seconds at the indicated amplitudes. The concentration of solubilized sGAG measured using the BLYSCAN™ assay. Data are presented as means±s.d. for n=3 samples per group. (C) The concentration of solubilized collagen as a function of sonication time. Comminuted dECM was sonicated at 100% amplitude for the indicated times. The concentration of solubilized collagen measured using the SIRCOL™ assay. Data are presented as mean±s.d. for n=3 samples per group. * represents p<0.05. Superscripts designate pairwise comparisons. (D) The concentration of solubilized sGAG as a function of sonication time. Comminuted dECM was sonicated at 100% amplitude for the indicated times. The concentration of solubilized sGAG was measured using the BLYSCAN™ assay. Data are presented as mean±s.d. for n=3 samples per group.
Figure 15B:
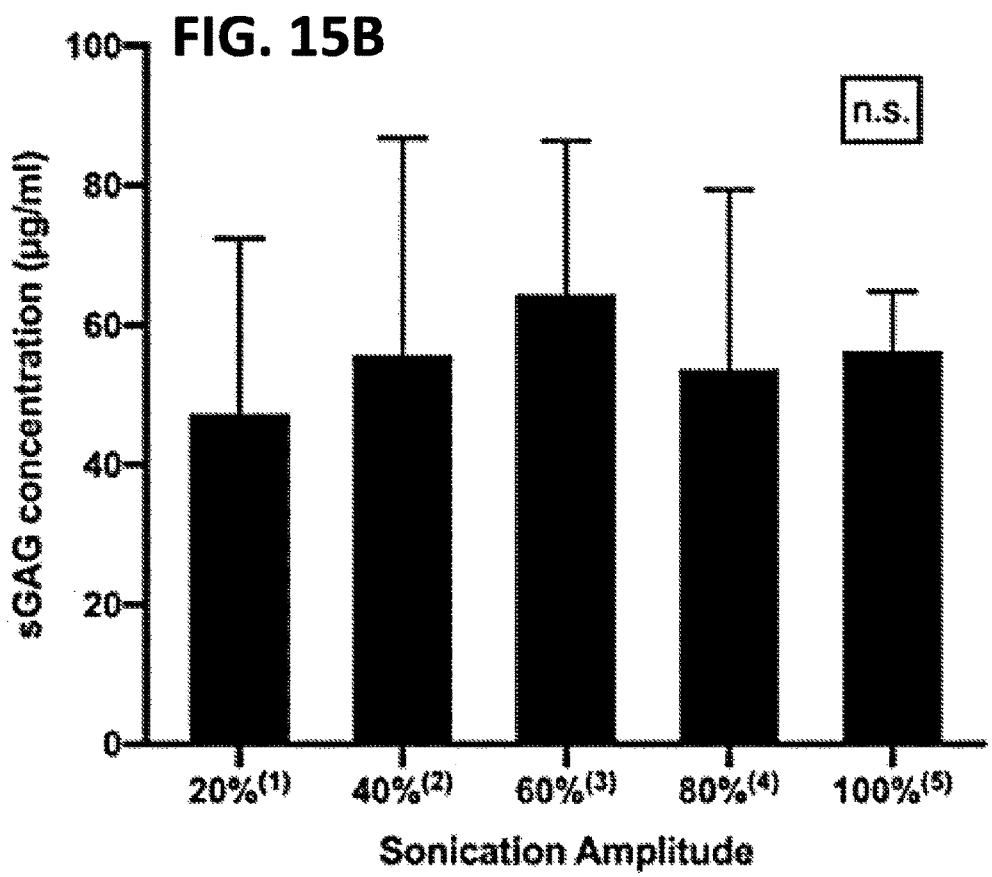
Figure 15C:
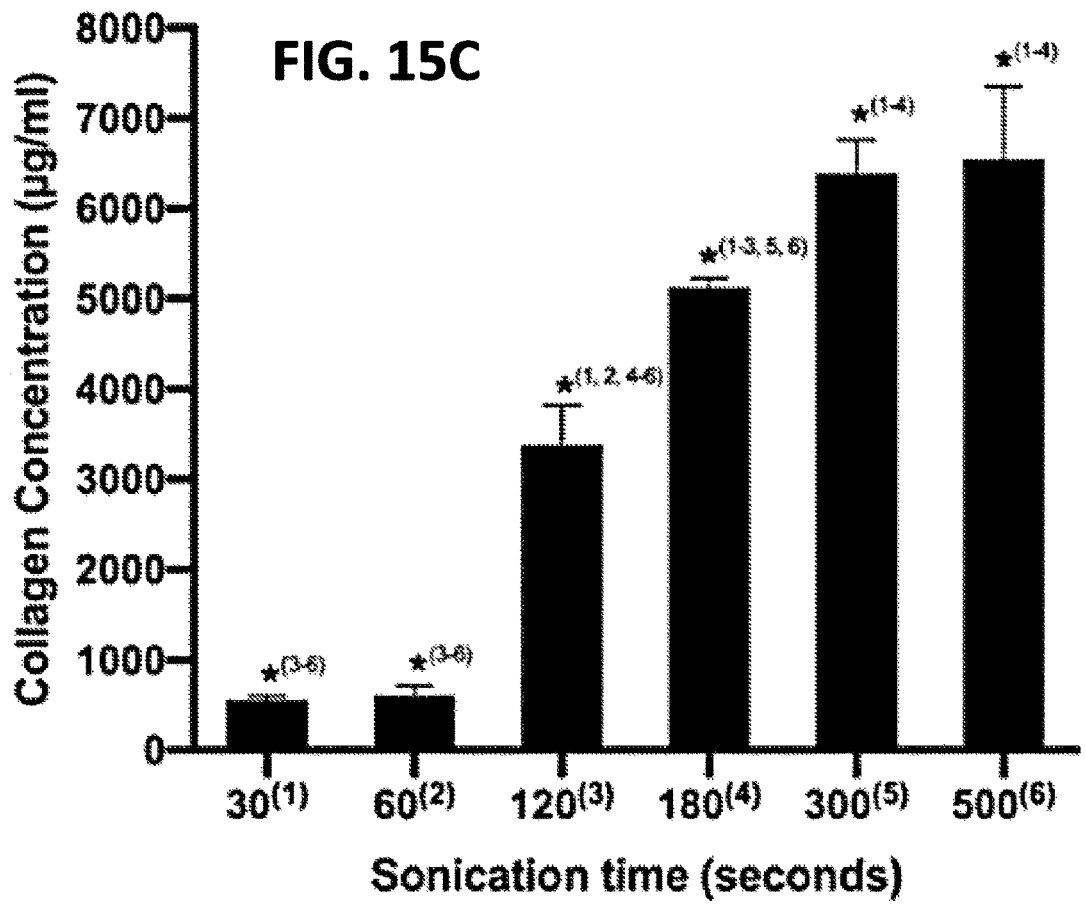
Figure 15D:
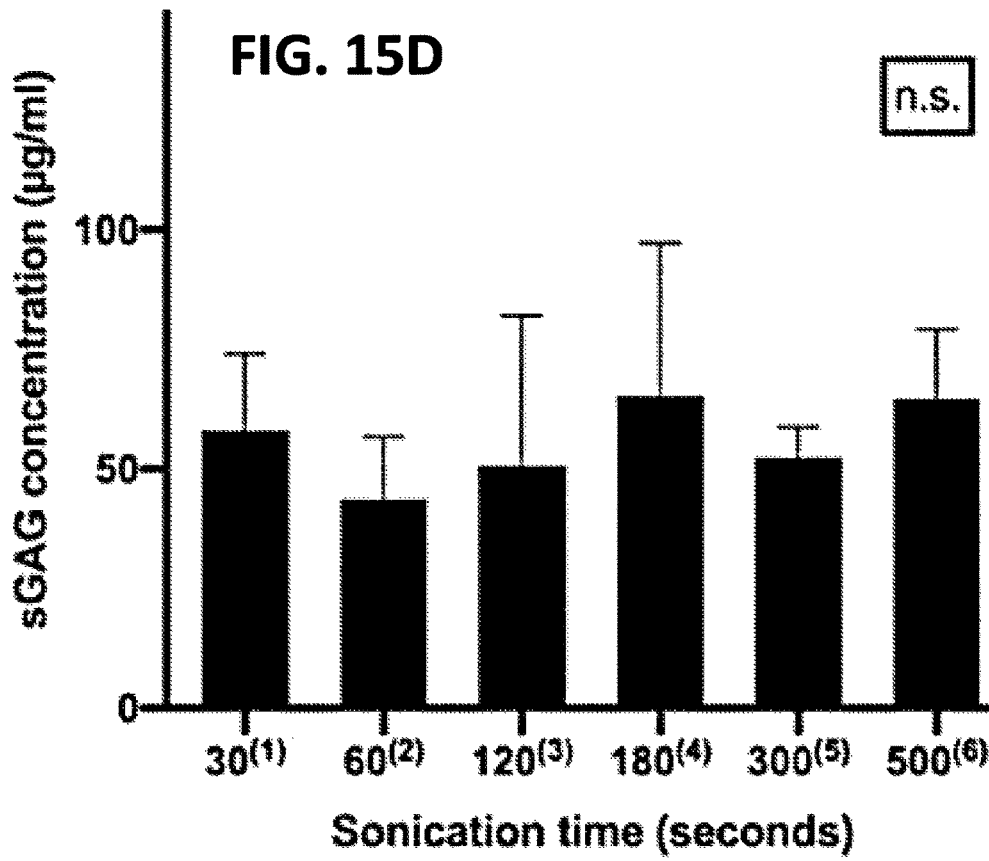

To evaluate the effect of sonication amplitude on the solubilization of collagen and sulfated glycosaminogylcans (sGAG), comminuted dECM was sonicated for 300 seconds at 20%, 40%, 60%, 80% and 100% amplitude. Results showed a significant increase in solubilized collagen with increasing sonication amplitude (FIG. 15A). In contrast, sonication amplitude did not have a significant effect on the solubilization of sGAG (FIG. 15B). To evaluate the effect of sonication time on the solubilization of collagen sGAG, comminuted dECM was sonicated at 100% amplitude for times ranging from 30 to 500 seconds. Results showed a significant increase in solubilized collagen with increasing sonication time (FIG. 15C). In contrast, sonication time did not have a significant effect on the solubilization of sGAG (FIG. 15D).

Example 5

Gelation Kinetics and Qualitative Assessment

Figure 16A:
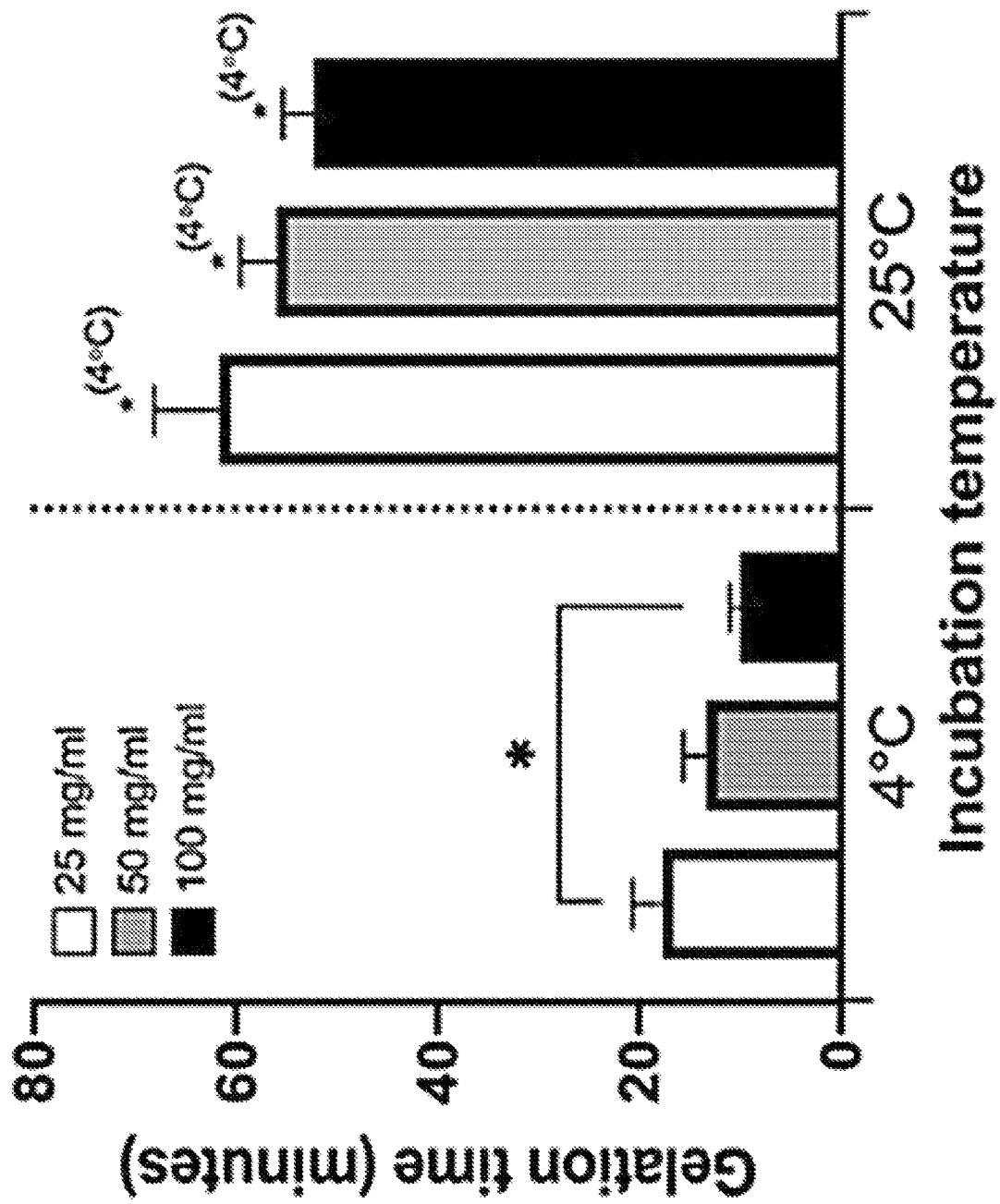
FIGS. 16A-16C. Effect of temperature and sonication amplitude on the gelation time of ECM hydrogels prepared using ultrasonic cavitation. (A) Effect of temperature on gelation time. 25, 50 and 100 mg/ml dECM were sonicated for 300 s at 100% amplitude, and then incubated at the indicated temperatures to induce gelation. Data are presented as means±s.d. for n=3 samples per group. *represents p<0.05. Superscripts designate pairwise comparisons. (B) Effect of sonication amplitude on gelation time. 25, 50 and 100 d ECM were sonicated for 300 s at the indicated amplitudes, and then incubated at 4° C. to induce gelation. Data are presented as means±s.d. for n=3 samples per group. *represents p<0.05. Superscripts designate pairwise comparisons. (C) Gelation assay evaluating the effect of temperature on gelation time of UBM, SIS, eECM, tECM or LECM. 100 mg/ml concentration of the indicated tissue ECM was sonicated for 300 s at 100% amplitude and then incubated at 4° C. or 25° C. to induce gelation. Data are presented as means±s.d. for n=3 samples per group. * represents p<0.05. Superscripts designate pairwise comparisons.
Figure 16B:
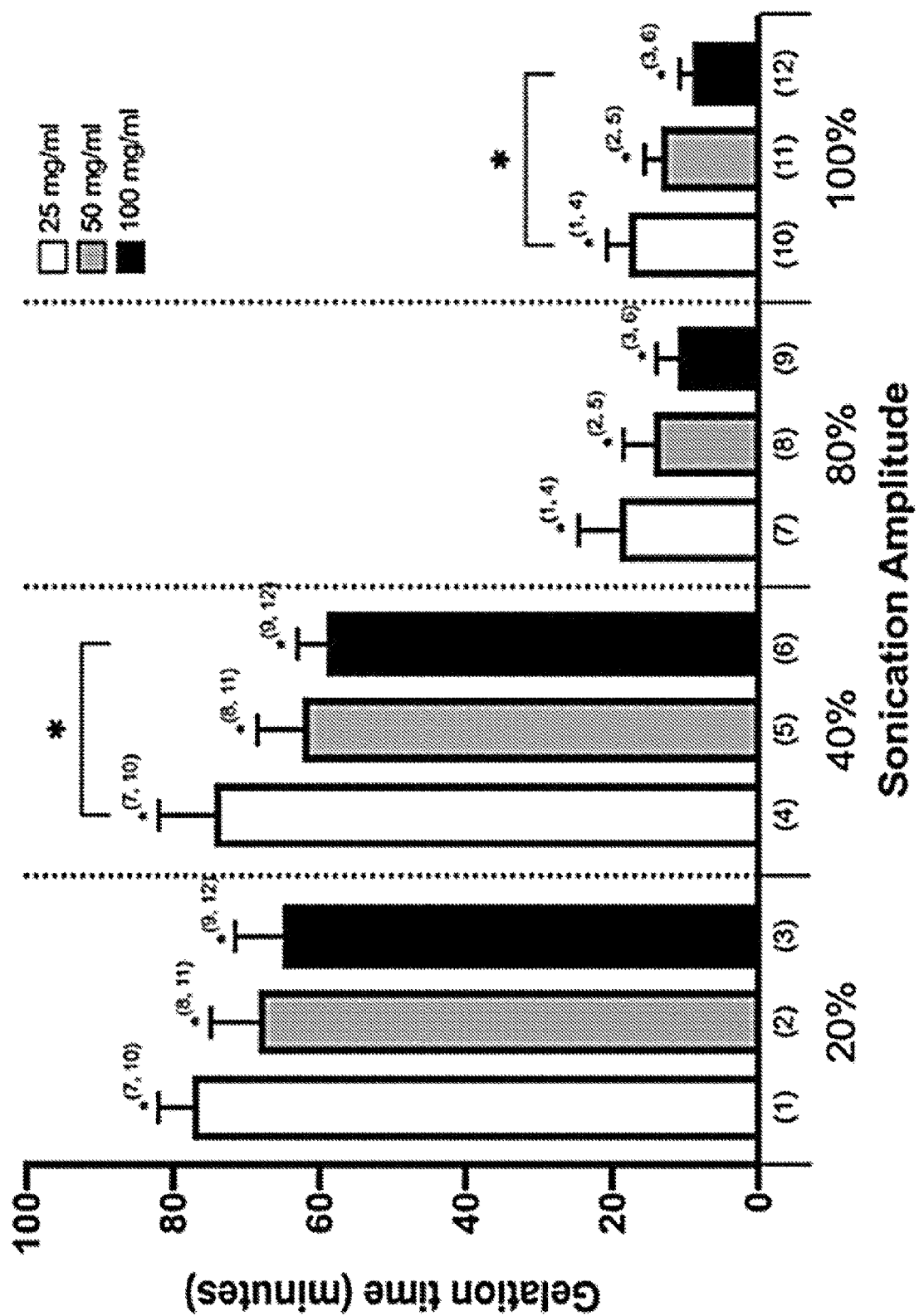
Figure 16C:
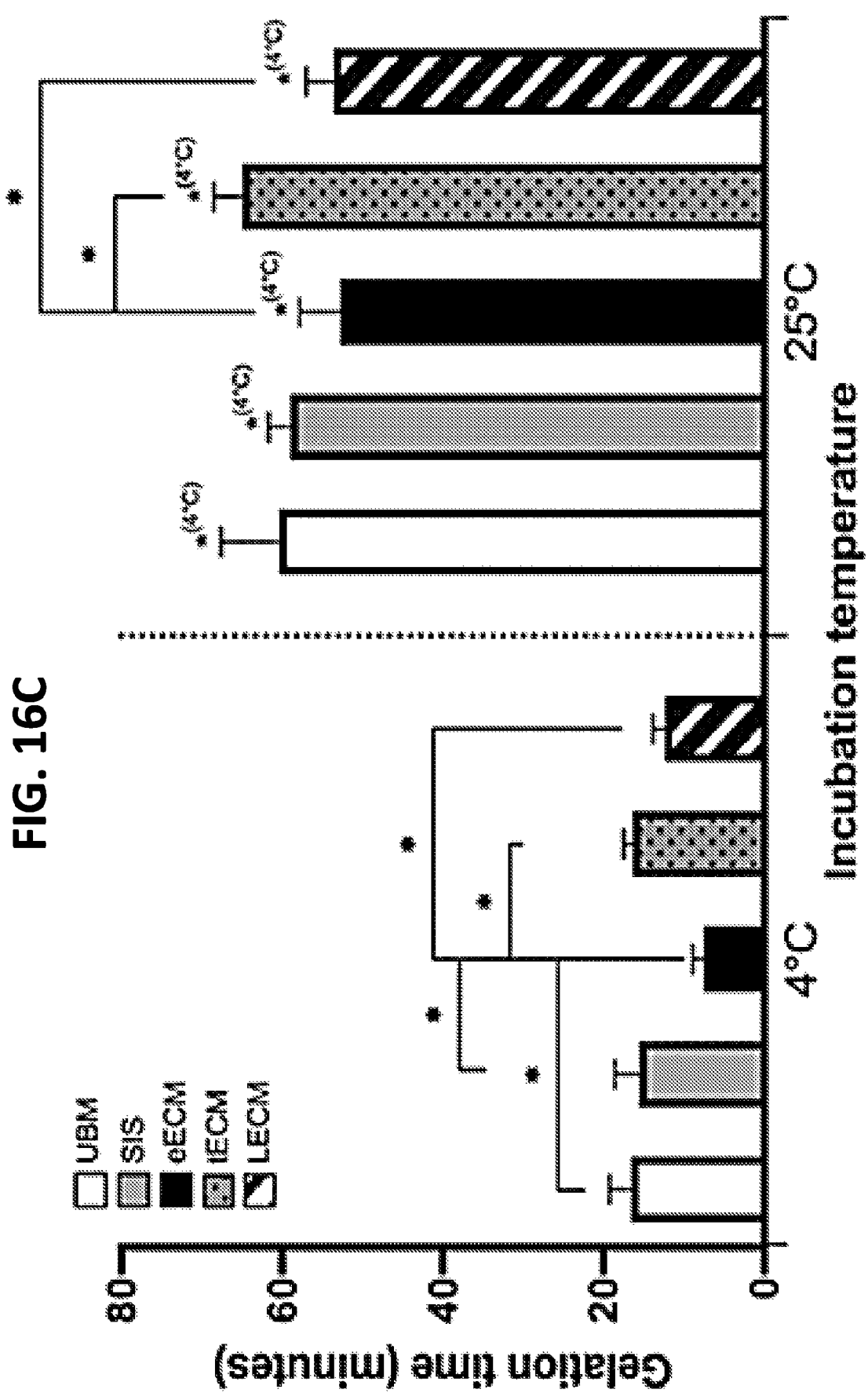

The effect of sonication time and amplitude on the gelation kinetics of dECM hydrogels prepared at 25, 50 or 100 mg/ml concentrations was calculated. Results showed that for all concentrations tested, incubation of the pre-gel solutions at 4° C. compared to 25° C. significantly reduced the time required to form a gel (FIG. 16A). Furthermore, the 100 mg/ml concentration showed a significant decrease in gelation time compared to the 25 mg/ml concentration when incubated at 4° C. (FIG. 16A). At all concentrations tested, increasing the sonication amplitude from 20 or 40% to 80 or 100% amplitude resulted in a significant decrease in gelation time (FIG. 16B). Significant differences in gelation time were observed between 25 and 100 mg/ml concentrations that were sonicated at 40 or 100% amplitude (FIG. 16B). Gelation kinetics were determined for UBM, SIS, eECM, tECM, and LECM prepared at 100 mg/ml concentration (FIG. 16C). Results showed that for all ECM tissue types tested, incubation of the pre-gel solutions at 4° C. significantly reduced the time required to form a gel compared to incubation at 25° C. Furthermore, eECM hydrogel showed significantly reduced gelation time at 4° C. compared to all other ECM tissue types. When incubated at 25° C., eECM showed a significantly reduced gelation time compared to tECM and LECM. Scanning electron micrographs of a 50 mg/ml and 100 mg/ml dECM hydrogel showed a dense fibril network with organized collagen fibrils (FIG. 3).

Example 6

Rheological Measurements

Figure 17A:
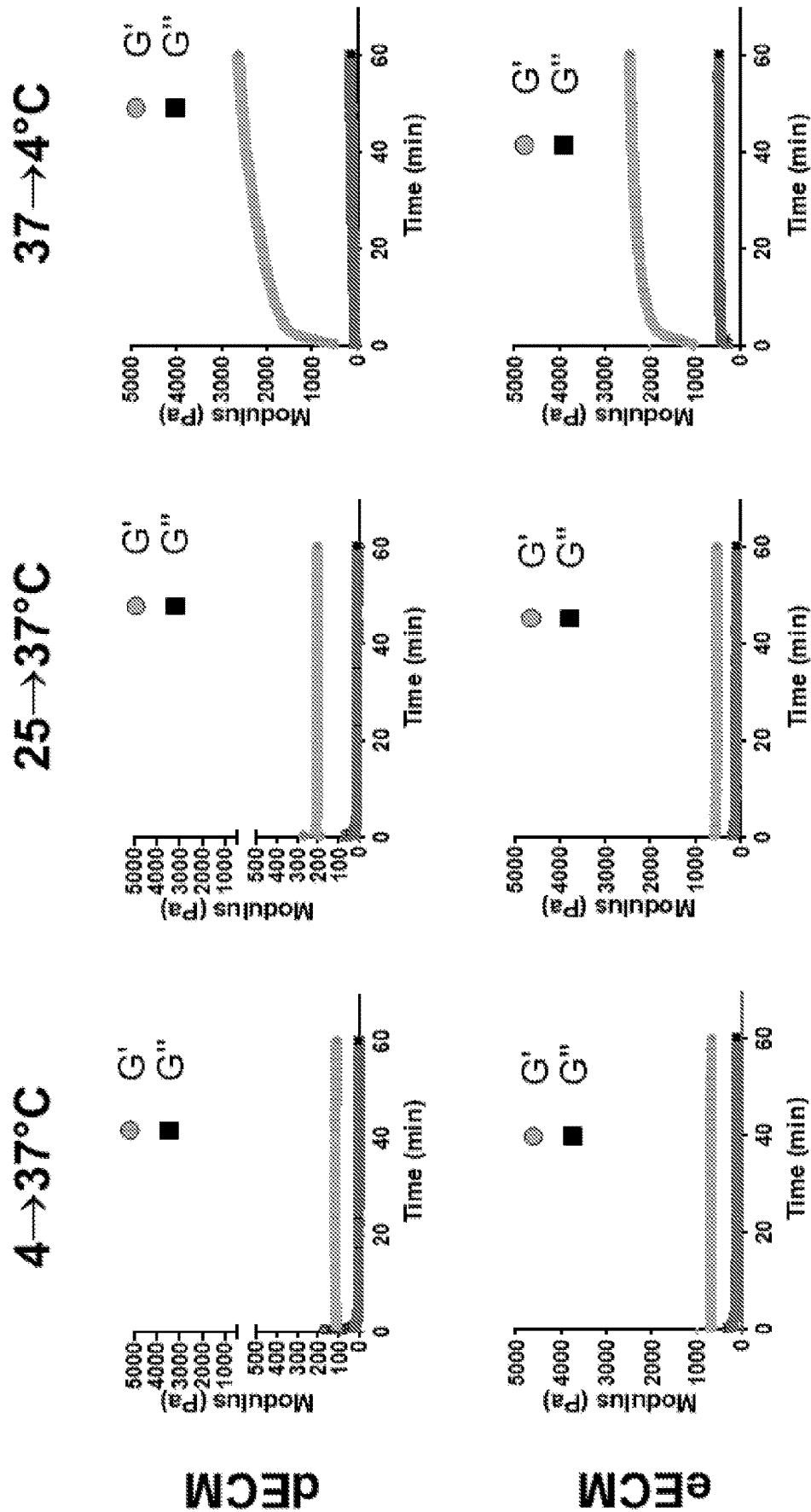
FIGS. 17A-17C. Viscoelastic characterization of ECM hydrogels prepared using ultrasonic cavitation. (A) Representative graphs of the ECM hydrogel gelation kinetics at 3 temperature profiles for dECM and eECM. The storage modulus (G') sigmoidally increased when temperature was rapidly decreased (37→4° C.). Hydrogel stiffness (G') was maintained when temperature was rapidly increased (4→37° C. and 25-37° C.). (B) Average storage modulus at the 3 temperature profiles (n=3, means±SD). (C) Average time to 50% gelation for the sigmoidal temperature profile 37→4° C. (n=3, means±SD). *p 0.05, **p 0.01.
Figure 17B:
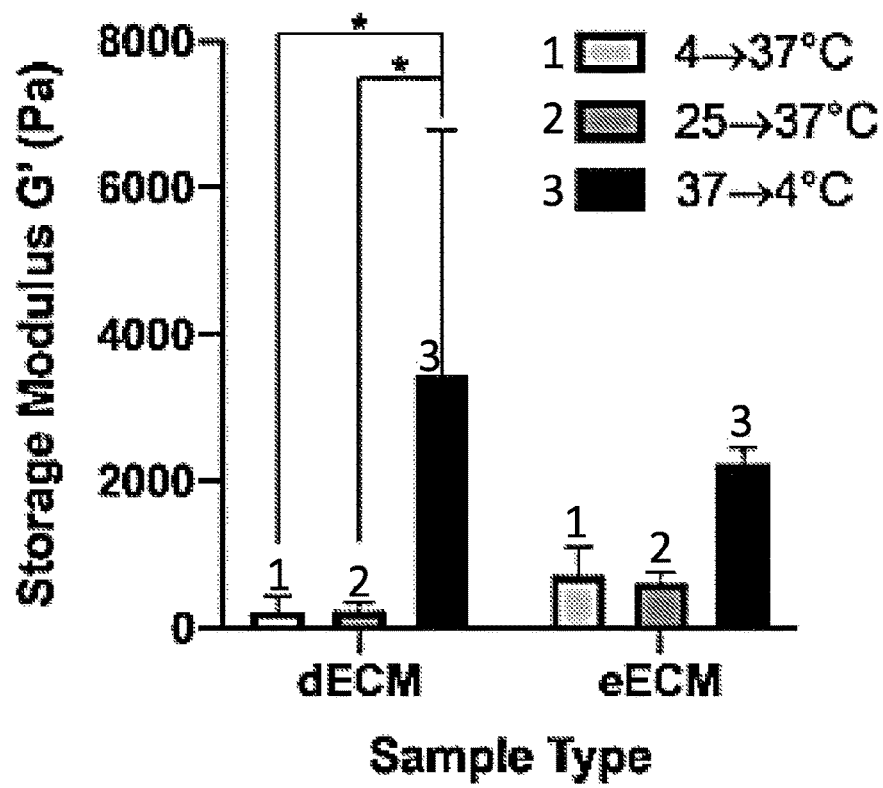
Figure 17C:
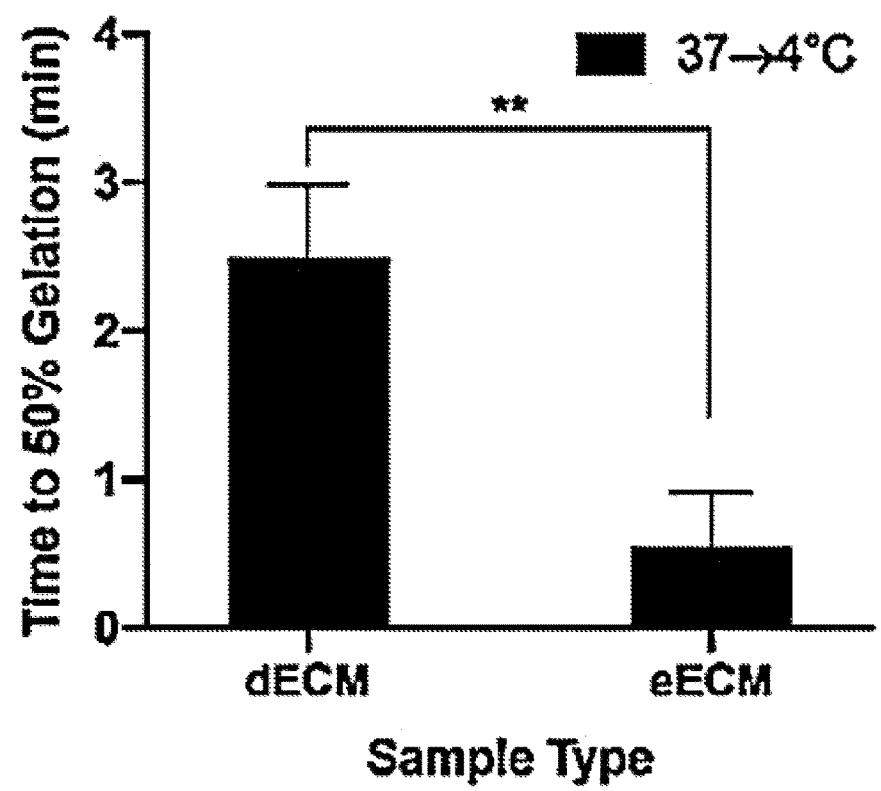
Figure 18B:
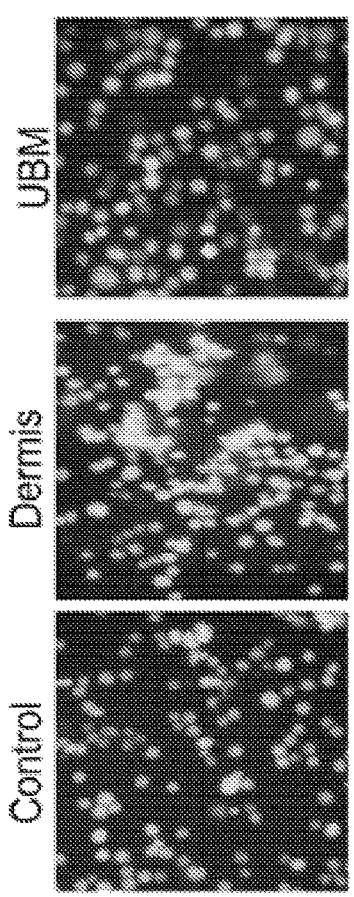
FIGS. 18A-18E. In vitro cell response. (A) 3T3 Fibroblasts were seeded on control (uncoated), or on dishes coated with ECM hydrogel prepared from UBM, SIS or Dermis, and cultured for 24 h. Cell metabolic activity was evaluated using the VYBRANT® MTT Cell Proliferation Assay Kit. Data are presented as means±s.d. for n=3 samples per group. (B, C) Live/Dead assay. Primary equine mesenchymal stem cells were seeded on control (uncoated), or on dishes coated with ECM hydrogel prepared from dECM or UBM. Viability was evaluated using the Live/Dead assay kit. Cells were imaged at 200× (B), and percent live and dead cells were quantified using Cell Profiler (C) Data are presented as means±s.d. for n=3 samples per group. (D) Murine bone marrow-derived macrophages were untreated (control) or treated with the following test articles for 24 hours: IFNγ+LPS, IL-4, dECM hydrogel, or eECM hydrogel. Cells were immunolabeled with F4/80 (macrophage marker), iNOS (M1-like marker), or Fizz1 (M2-like marker). Cells were imaged at 200×. (E) Quantification of F4/80, iNOS and Fizz1 immunolabeling. Data are presented as means±s.d. for n=3 per group.
Figure 18C:
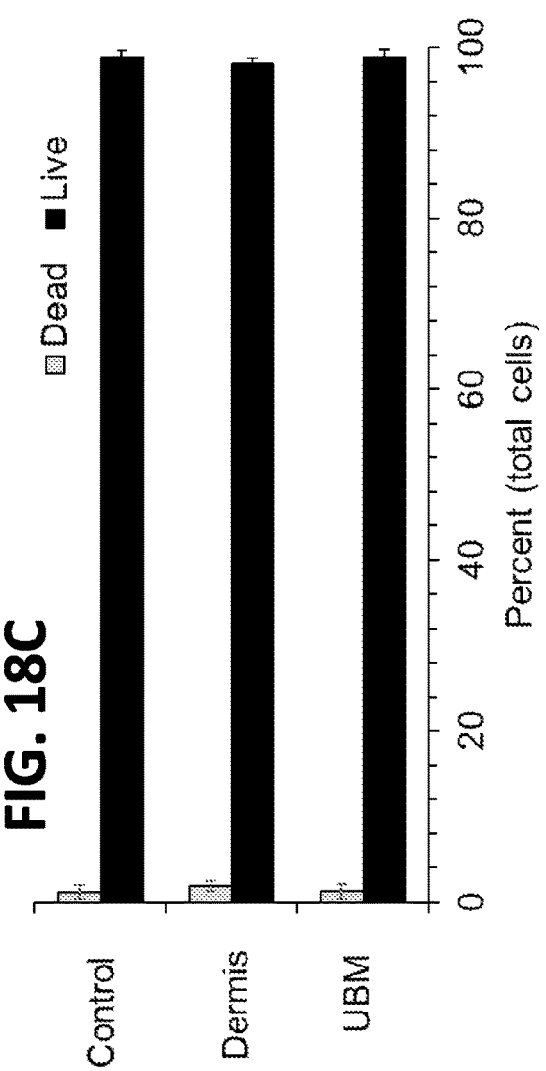

Two tissue types of ECM hydrogels (dECM and eECM, 100 mg/ml)) were tested at 3 temperature profiles: 1) 4→37° C., 2) 25→37° C., and 3) 37→4° C. (FIG. 17A). ECM hydrogels showed a sigmoidal increase in gelation (storage modulus, G') when temperature was decreased (37→4° C.). The hydrogels exhibited a storage modulus G'>loss modulus G" at the plateau of the sigmoidal gelation curve. When temperature was increased (4→37° C. or 25→37° C.), the stiffness of the hydrogel was maintained (G'>>G") over time (FIG. 17A). The storage modulus G' was increased in the dECM hydrogels when the end temperature was rapidly decreased 37→4° C. (3447.3±3340.1 Pa) compared to when the end temperature was increased 4→37° C. (234.4±215.7 Pa) ($p=0.04$) or 25→37° C. (245.8±94.5 Pa) ($p=0.04$) (FIG. 17B). The stiffness for eECM also trended toward an increase when the end temperature was rapidly decreased 37→4° C. (2237.4±227.1 Pa) compared to 4→37° C. (733.0±363.7 Pa) or 25→37° C. (624.1±133.5 Pa) but was not significant ($p=0.4$) (FIG. 17B). Gelation time (time to 50% gelation) was determined for the sigmoidal gelation profile of 37→4° C. for dECM and eECM (FIG. 18C). Gelation time was shorter for eECM (0.5±0.4 min), compared to dECM (2.5±0.5 min) by student's unpaired t-test ($p=0.006$). Gelation time was not determined for the temperature profiles raised to 37° C. because gelation was maintained.

Example 7

In Vitro Cell Response

Figure 18A:
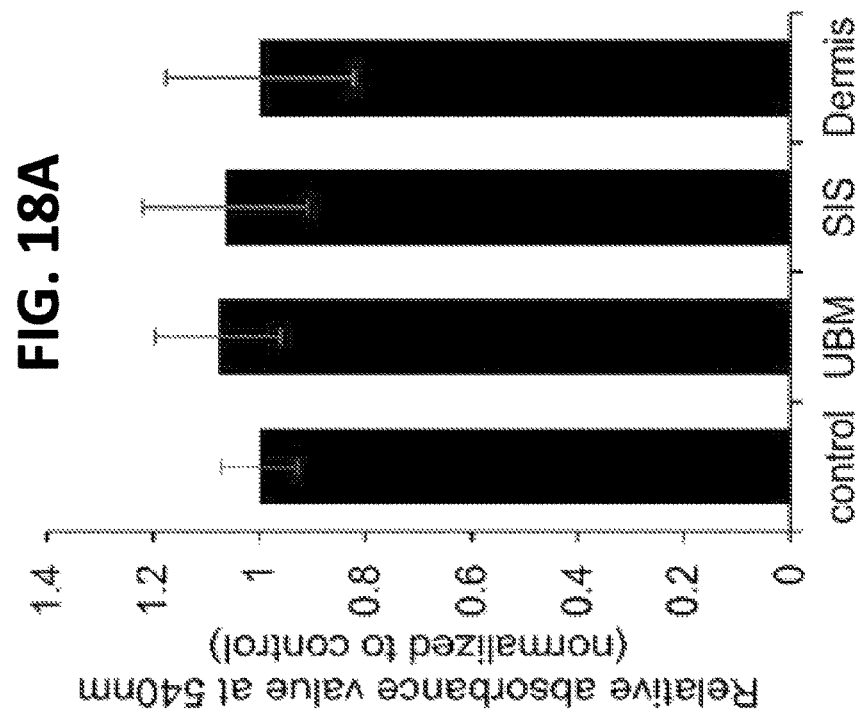
Figure 18D:
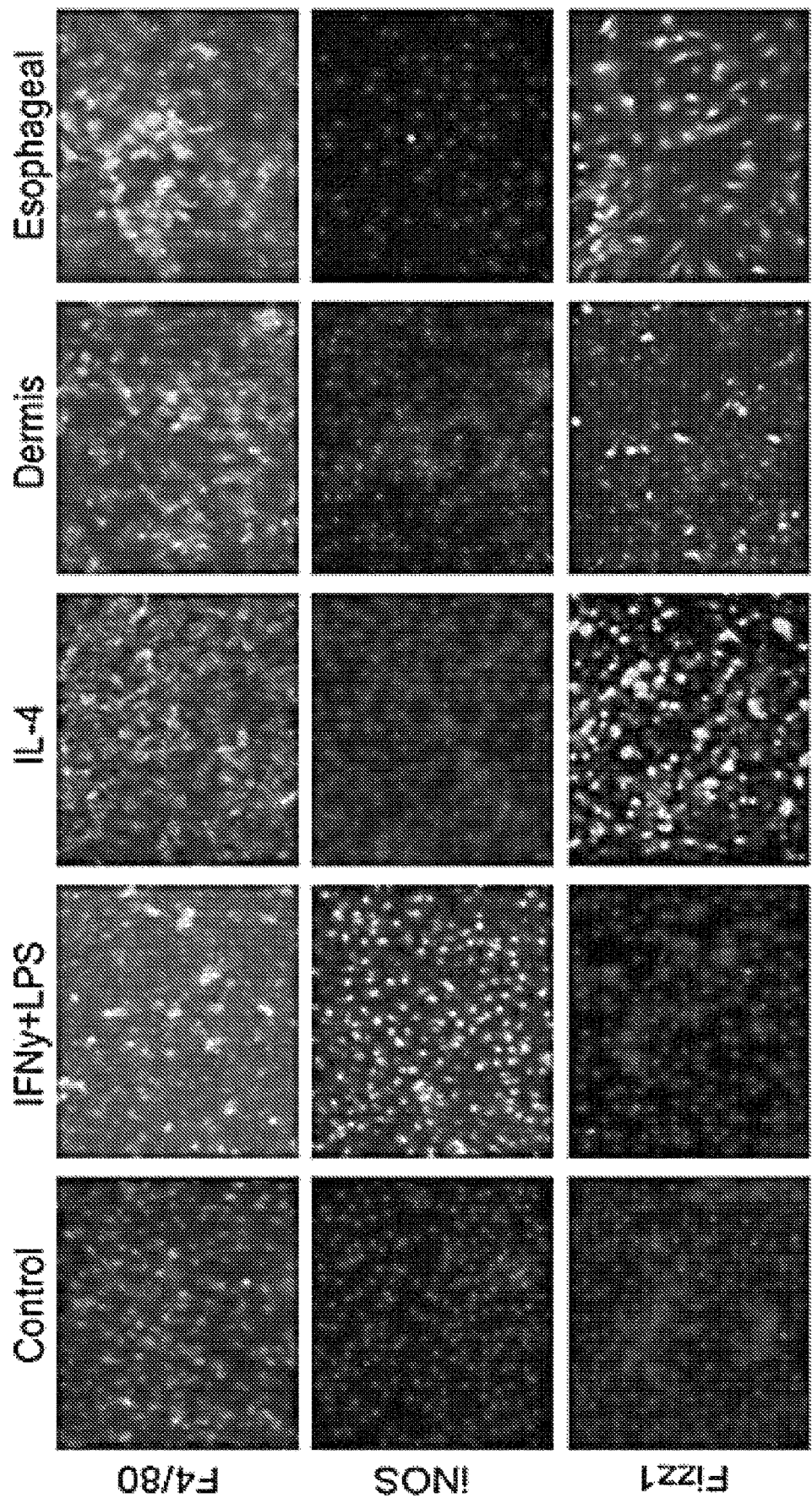
Figure 18E:
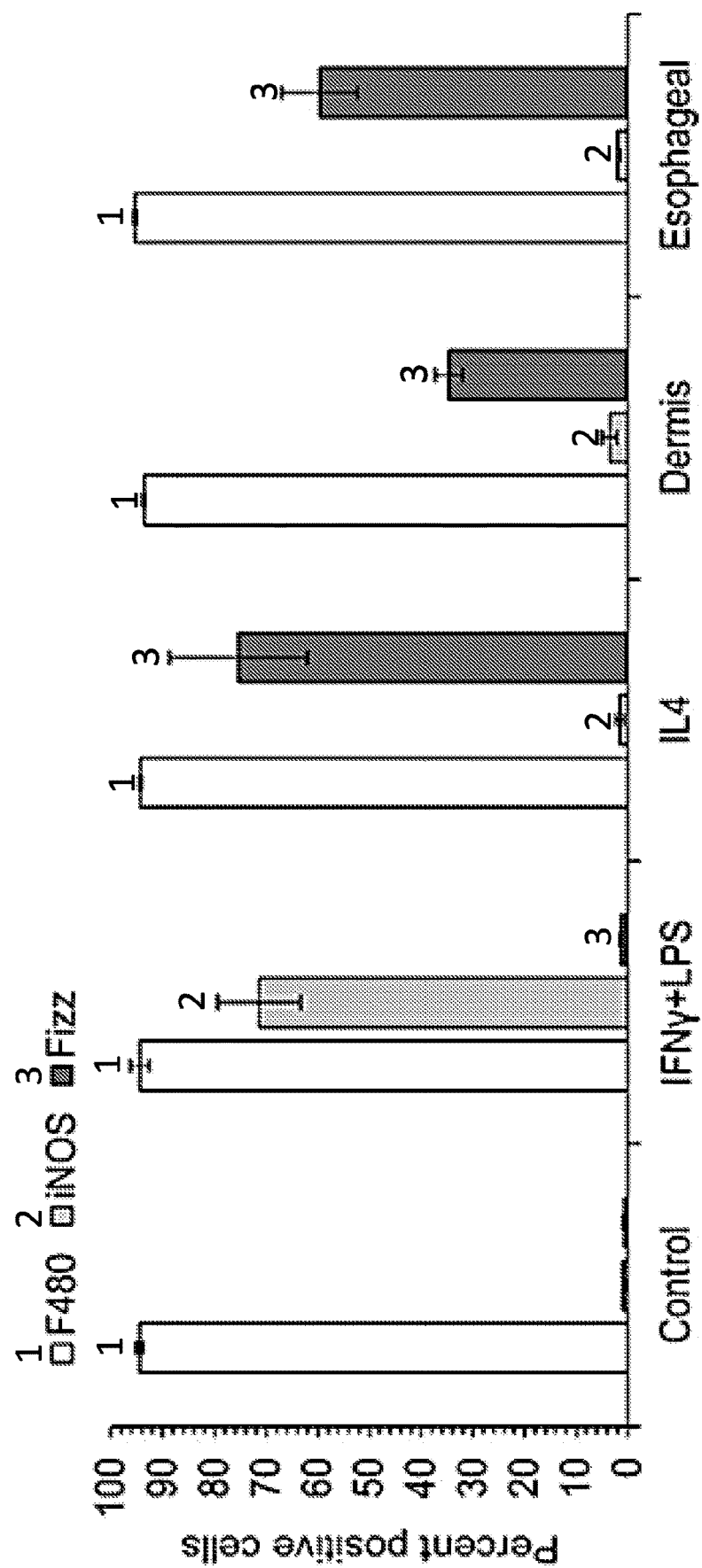

MTT Cell Proliferation Assay showed ECM hydrogels prepared from dECM, UBM or SIS to be non-cytotoxic for NIH 3T3 fibroblasts (FIG. 18A). Similarly, results from a live/dead assay showed that primary equine mesenchymal stem cells retained nearly 100% viability when seeded on ECM hydrogels prepared from dECM or UBM (FIGS. 18B, C). There were no differences in proliferation and viability between these treatments and when compared with cells cultured on tissue culture plastic (control) for 24 hr (FIGS. 18B, C). ECM hydrogels prepared using the pepsin digestion method have previously been shown to promote an M2-like macrophage phenotype (Huleihel et al., "Macrophage phenotype in response to ECM bioscaffolds," Seminars in immunology, Elsevier, 2017, pp. 2-13; Sicari et al., Biomaterials 35(30) (2014) 8605-8612; Dziki et al., Journal of biomedical materials research Part A 105(1) (2017) 138-147). To evaluate if ECM hydrogels prepared using the ultrasonic cavitation method exhibit similar effects on macrophages primary murine bone marrow-derived macrophages were stimulated with interferon-γ (IFN-γ) and lipopolysaccharide (LPS) to induce an M1-like macrophage phenotype, interleukin-4 (IL-4) to induce an M2-like phenotype, dECM hydrogel or eECM hydrogel. All experimental groups showed uniform F4/80 staining. The controls showed an expected increase in iNOS when macrophages were treated with IFNγ/LPS and an increase in Fizz1 when treated with IL-4 (FIGS. 18B, D, E). Both dECM and eECM hydrogel treatment were found to promote an M2-like macrophage activation, similar to IL-4-treated macrophages as shown by Fizz1 expression accompanied by little iNOS expression (FIGS. 18B D, E).

Thus, the gelation kinetics, rheological properties, and the cytocompatibility and bioactivity of ECM hydrogels prepared using ultrasonic cavitation were evaluated. Although the present study focused primarily on the use of dECM to develop and evaluate the ultrasonic cavitation method, ECM from five additional source tissues were used in selective assays to show that the ultrasonic cavitation method can be applied to ECM derived from a wide range of decellularized tissues as summarized in Table 1.

TABLE 1

Summary of the ECM source tissues, and the selective assays used to evaluate the ultrasonic cavitation method for producing ECM hydrogels.

| ECM tissue type | Assays utilized |
|---|---|
| dECM | Solubilization Assay |
|  | Gelation Assay |
|  | Scanning Electron Microscopy |
|  | Rheological assessment |
|  | In-vitro metabolic |
|  | In-vitro cytocompatibility |
|  | In-vitro macrophage response |
| eECM | Gelation Assay |
|  | Rheological assessment |
|  | In-vitro macrophage response |
| UBM | Gelation Assay |
|  | In-vitro metabolic assay |
|  | In-vitro cytocompatibility |
| SIS | Gelation Assay |
|  | In-vitro metabolic assay |
| tECM | Gelation Assay |
| LECM | Gelation Assay |

The ECM tissue sources that were evaluated were dermal ECM (dECM), esophageal ECM (eECM), urinary bladder matrix (UBM), small intestinal submucosa (SIS), trachea ECM (tECM), and liver ECM (LECM).

In the present studies, ECM scaffolds were solubilized without the need for digestion with an acid protease in an acidic solution; or the use of chaotropic extraction buffers and dialysis procedures which can adversely affect the molecular composition of the ECM. The sonicated ECM self-assembled into a gel when incubated at temperatures at or below 25° C. Without being bound by theory, gelation may be due to the presence of self-assembling molecules such as collagen. Indeed, sonication of the ECM scaffold material resulted in a substantial increase in solubilized collagen with increasing sonication time and amplitude. Unlike ECM hydrogels prepared using pepsin digestion and which maintain a liquid-state at 25° C. and gel at 37° C., hydrogels prepared using the ultrasonic cavitation method formed a stable gel when the temperature was lowered to 25° C. or below. This thermomechanical property of sonicated ECM is similar to that reported for hydrolyzed collagen, which is capable of forming a gel upon cooling to temperatures below 30° C. (Tosh et al., Applied Physics Letters 84(21) (2004) 4242-4244). However, a recent study which utilized circular dichroism analysis, atomic force microscopy and FTIR on collagen extracted from bovine tendons showed that the triple helix structure of the collagen is not affected by sonication and remains intact (Li et al., Sonochemistry 16(5) (2009) 605-609). Similarly, extraction of collagen from the skins of sea bass *Lateolabrax japonicus* showed that sonication at 80% amplitude for 3 hr did not induce detectable changes in the structural integrity of the collagen molecule (Kim et al., Fisheries science 79(5) (2013) 849-856). In the present study, scanning electron micrographs of sonicated ECM showed a dense fibrillary network with organized collagen fibrils. In addition, despite the inverse relationship between gelation and temperature of ECM hydrogels produced using ultrasonic cavitation, when temperature was increased (4→37° C. or 25→37° C.), the stiffness of the hydrogel was maintained (G'>>G") over time. These findings suggest that the gelation process of sonicated ECM is not simply a product of collagen chemistry, but rather a result of the interplay between the various components within the solubilized ECM, which include other self-assembling molecules such as laminins and proteoglycans.

NIH 3T3 fibroblasts and primary equine mesenchymal stem cells were able to adhere to and proliferate upon the ECM hydrogels produced using ultrasonic cavitation. Furthermore, although the mechanism(s) of action of ECM-mediated tissue remodeling are only partially understood, the activation state of infiltrating macrophages at the remodeling site from a proinflammatory, M1-like phenotype to a constructive and pro-remodeling M2-like macrophage phenotype has been shown to be a predictor of favorable down-stream remodeling outcomes (Brown et al., Acta Biomater 8(3) (2012) 978-87). The results presented herein demonstrate that ECM hydrogels produced using ultrasonic cavitation maintain the ability to promote an M2-like macrophage phenotype.

Example 8

Gamma Irradiation of Acoustic Hydrogels

Figure 20A:
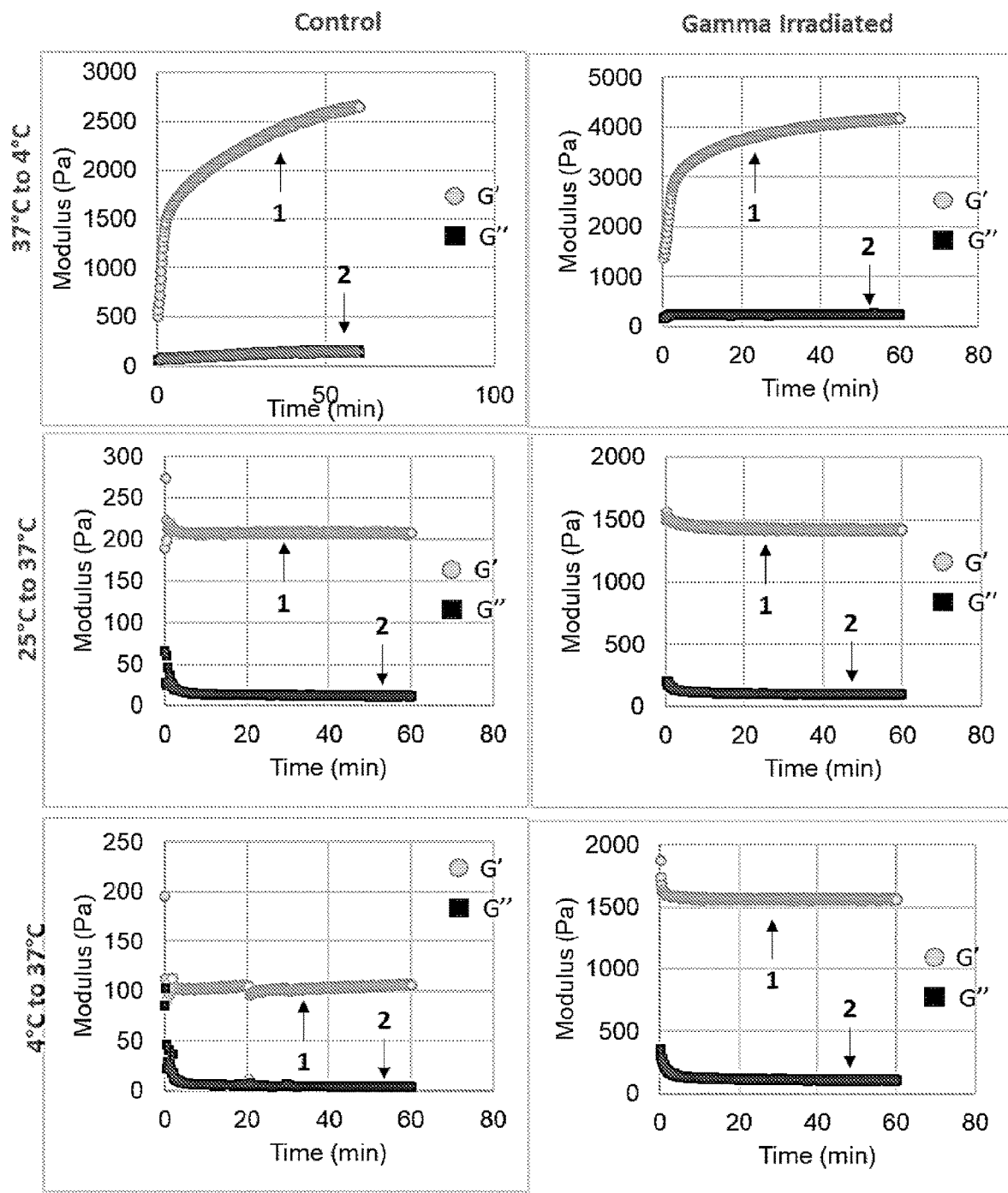

Acoustic hydrogels (100 mg/mL) were sterilized with 20 kGy gamma irradiation at room temperature. Hydrogel "stiffness" over time was measured for gamma irradiated (20 kGy) and non-sterilized control acoustic hydrogel (dermal ECM 100 mg/mL). The storage modulus ("stiffness") (G') and loss modulus (G") were measured by applying a small, 0.5% oscillatory strain to the sample. Three temperature profiles were tested: temperature was rapidly raised from the initial storage temperature to final temperature: 4 to 37° C., 25 to 37° C., or 37 to 4° C. (FIG. 20A) Representative graphs of the time sweep are shown (FIG. 20B) The average storage and loss modulus, averaged over the final 5 minutes of the test, are shown.

After formation of the acoustic hydrogel, the gels were placed in a Cesium-137 irradiator and subjected to 2065 rads/min of ionizing radiation at room temperature for 16 hours, resulting in a final radiation dose of 20 kGy.

Surprisingly and unexpectedly, gamma irradiation did not affect the acoustic hydrogel's ability to remain in gel form. In contrast, enzymatically produced ECM hydrogels are unable to remain as a gel when gamma irradiated and gamma irradiated pre-gels of ECM hydrogels are unable to form a gel when gamma irradiated prior to gelation.

Example 9

Acoustic Hydrogel as a Submucosal Fluid Cushion

The acoustic hydrogels that were evaluated for use as a submucosal cushion were prepared by resuspending 1 gram of dermal ECM (dECM) powder or esophageal ECM (eECM) powder (prepared as described in Example 3) in 10 ml of phosphate buffered saline (PBS) in a 50 mL conical tube. The samples were sonicated for 3 minutes at 100% amplitude using a FISHERBRAND™ Model 120 Sonic Dismembrator equipped with a ⅛" probe. Following sonication, the samples were transferred to 5 ml syringe and incubated at 4° C. to induce gel formation.

Anesthesia was induced with Acepromazine (0.01 mg/kg, SC) and ketamine (5-11 mg/kg), and surgical plane anesthesia maintained with 1-5% Isofluorane via endotracheal tube. Throughout the procedure and immediate post-operative period, pigs were administered 2 ml/kg/h of lactated Ringer's solution I.V. Temperature was controlled through warm water recirculating heating pads placed under the animal. Physiologic parameters such as heart, respiration rate, body temperature, and responsiveness are monitored during the procedure. Antibiotic prophylaxis with 25 mg/kg of Cefazolin is administered before starting the procedure.

The pig was placed in supine position with and a Pentax EG3430K endoscope was used to evaluate the mucosa of the tubular organ. After identifying reference points in the organ, the mucosa and submucosa are separated from the underlying layers at the site of excision by injection of the acoustic ECM hydrogel in gel form which was dyed blue to provide visual contrast, at 8 mg/ml into the submucosal space using a Olympus Injectorforce 4 mm 23G needle. Approximately 2-5 ml of blue gel is injected per site. The full circumference of the mucosa (100%) for a length of 5 cm was removed using band-ligation EMR technique. For EMR, a Cook Duette Kit with a ligation band was used. The mucosa was then excised with the use of a snare. Results are shown in FIGS. 19A-19C.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method of producing an extracellular matrix (ECM) hydrogel, comprising:
solubilizing mammalian ECM in a liquid using ultrasound frequency to produce an acoustic ECM hydrogel in a liquid phase, wherein the mammalian ECM is present at a concentration of about 25 mg/ml to about 600 mg/ml.

2. The method of claim 1, wherein the ultrasound frequency is applied to the ECM in the liquid at a temperature between 30° C. to 43° C.

3. The method of claim 1, wherein the ultrasound frequency is about 20 kHz to about 100 kHz.

4. The method of claim 3, wherein the ultrasound frequency is applied to the ECM in the liquid for at least 30 seconds.

5. A method of producing an extracellular matrix (ECM) hydrogel, comprising:
solubilizing mammalian ECM in a liquid at a concentration of about 25 mg/ml to about 600 mg/ml with ultrasound at a frequency of about 20 kHz to about 100 kHz at for at least about 60 seconds at a temperature of greater than about 37° C. to produce an acoustic ECM hydrogel in a liquid phase.

6. The method of claim 5, wherein the ultrasound frequency is applied to the mammalian ECM in the liquid for about 1 minute to about 5 minutes.

7. The method of claim 1, wherein the mammalian ECM is lyophilized mammalian ECM.

8. The method of claim 1, wherein the mammalian ECM is provided as pieces in the range of about 10 μm to about 2000 μm.

9. The method of claim 5, further comprising cooling the acoustic ECM hydrogel in the liquid phase to a temperature of about 37° C. or less, thereby producing the acoustic ECM hydrogel in a gel phase.

10. The method of claim 5, wherein the ultrasound is at a frequency of about 20 kHz.

11. The method of claim 1, wherein the ultrasound has an amplitude of about 20 µm to about 320 µm.

12. The method of claim 1, wherein the mammalian ECM is present at a concentration of about 25 mg/ml to about 150 mg/ml.

13. The method of claim 1, wherein the liquid is phosphate buffered saline.

14. The method of claim 1, wherein the ECM is a urinary bladder ECM, a small intestinal submucosal ECM, an esophageal ECM, a trachea ECM, a liver ECM or a dermal ECM.

15. The method of claim 14, wherein the ECM is porcine ECM or bovine ECM.

16. The method of claim 1, wherein the acoustic ECM hydrogel is gamma irradiated.

17. A method of producing an extracellular matrix (ECM) hydrogel comprising:
solubilizing mammalian ECM in a liquid using ultrasound frequency to produce an acoustic ECM hydrogel, wherein the ultrasound frequency is about 20 kHz to about 100 kHz.

18. The method of claim 17, wherein the mammalian ECM is present at a concentration of about 25 mg/ml to about 150 mg/ml and is provided as pieces in the range of about 10 µm to about 2000 µm.

19. The method of claim 18, wherein the ultrasound frequency is applied to the ECM in the liquid at a temperature of 30° C. to 43° C.

20. The method of claim 19, wherein the ultrasound has an amplitude of about 20 µm to about 320 µm.

21. The method of claim 20, wherein the ultrasound frequency is applied to the ECM in the liquid for about 30 seconds to about 5 minutes.

22. The method of claim 17, wherein the ECM hydrogel undergoes a gel to sol transition at about 37° C.

23. The method of claim 17, wherein the mammalian ECM is urinary bladder ECM, small intestinal submucosal ECM, esophageal ECM, tracheal ECM, liver ECM, or dermal ECM.

24. The method of claim 17, wherein the ECM is porcine ECM or bovine ECM.

* * * * *